United States Patent
Okada et al.

[11] Patent Number: 5,868,666
[45] Date of Patent: Feb. 9, 1999

[54] ENDOSCOPE APPARATUS USING PROGRAMMABLE INTEGRATED CIRCUIT TO CONSTITUTE INTERNAL STRUCTURE THEREOF

[75] Inventors: Yoshihiro Okada, Otsuki; Toshiaki Noguchi, Tachikawa; Mitsuhiro Ito, Itsukaichi-machi; Akira Taniguchi, Hachioji; Sumihiro Uchimura, Sagamihara, all of Japan

[73] Assignee: Olympus Optical Co., Ltd., Tokyo, Japan

[21] Appl. No.: 643,562

[22] Filed: May 6, 1996

Related U.S. Application Data

[63] Continuation of Ser. No. 281,699, Jul. 28, 1994, abandoned.

[30] Foreign Application Priority Data

| Nov. 26, 1993 | [JP] | Japan | 5-297063 |
| Nov. 29, 1993 | [JP] | Japan | 5-298516 |
| Nov. 29, 1993 | [JP] | Japan | 5-298517 |
| Nov. 29, 1993 | [JP] | Japan | 5-298518 |
| Dec. 22, 1993 | [JP] | Japan | 5-325314 |

[51] Int. Cl.⁶ .................................................. A61B 1/045
[52] U.S. Cl. ............................. 600/118; 600/178; 348/76
[58] Field of Search ..................................... 600/118, 178, 600/180; 348/68, 69, 72, 74, 76; 606/142; 369/17

[56] References Cited

U.S. PATENT DOCUMENTS

| 4,768,241 | 9/1988 | Beney . | |
| 5,184,159 | 2/1993 | Furuya et al. | 354/62 |
| 5,217,003 | 6/1993 | Wilk . | |
| 5,255,681 | 10/1993 | Ishimura | 128/660.09 |
| 5,269,307 | 12/1993 | Fife et al. | 128/661.01 |
| 5,383,880 | 1/1995 | Hooven | 606/142 |
| 5,408,263 | 4/1995 | Kikuchi et al. | 348/68 |

FOREIGN PATENT DOCUMENTS 5277065  10/1993  Japan .

OTHER PUBLICATIONS

Reference Data; XC4000, Logic Cell Array Family, 1990.

*Primary Examiner*—John P. Leubecker
*Attorney, Agent, or Firm*—Armstrong, Westerman, Hattori, McLeland & Naughton

[57] ABSTRACT

An endoscope apparatus including an endoscope, a supply portion for supplying a required signal or energy to a peripheral unit relating to the endoscope; and a control portion for controlling the supply portion, wherein the control portion is constituted to have at least one field programmable gate array and a function required by at least either of the endoscope or the peripheral unit relating to the endoscope is realized by receiving circuit information for constituting a control circuit for controlling the supply portion to selectively write the circuit information on the field programmable gate array so that the control circuit is constituted.

6 Claims, 31 Drawing Sheets

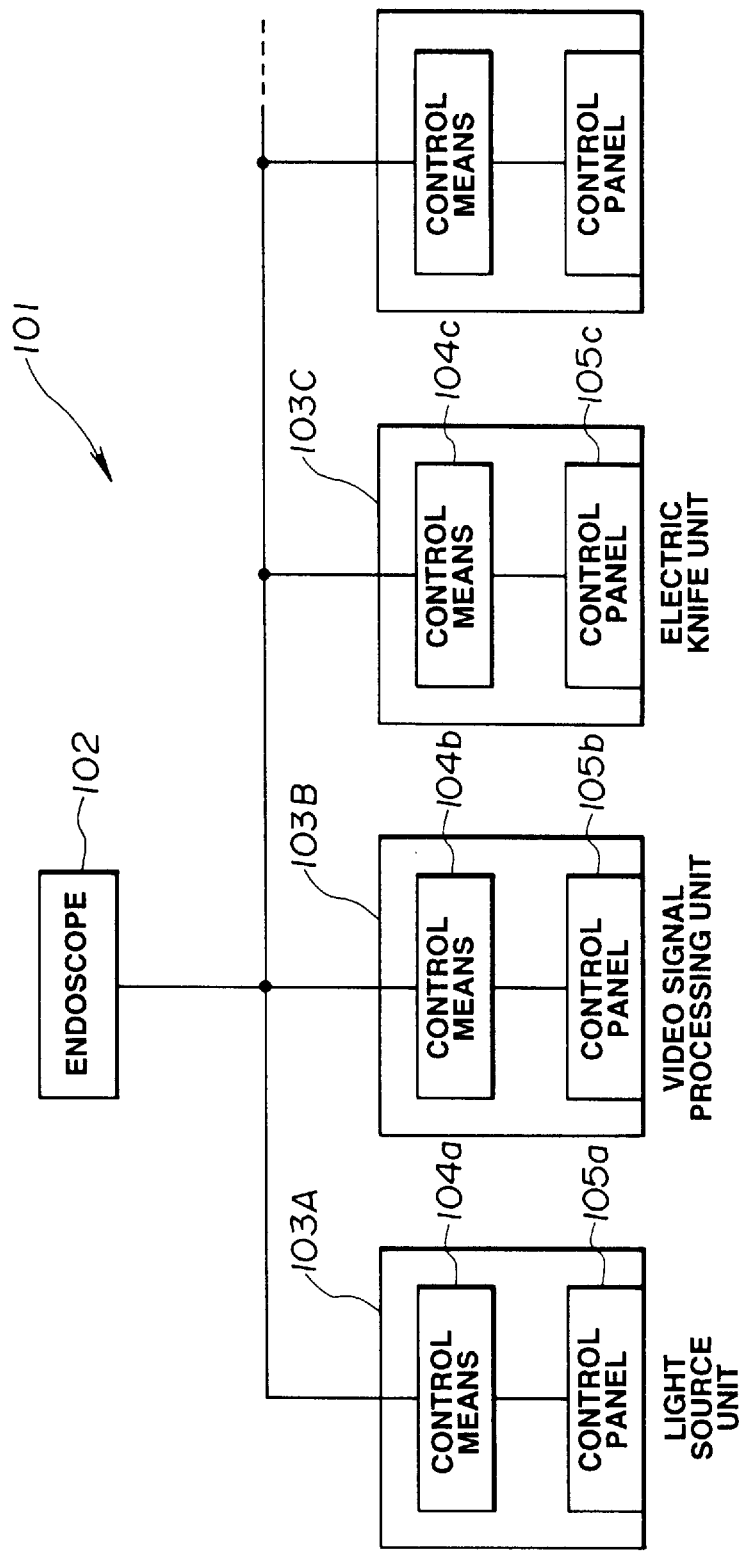

ENDOSCOPE APPARATUS USING PROGRAMMABLE INTEGRATED CIRCUIT TO CONSTITUTE INTERNAL STRUCTURE THEREOF

This application is a continuation of application Ser. No. 08/281,699 filed Jul. 28, 1994, now abandoned.

BACKGROUND OF THE INVENTION

1. Field of the Invention

The present invention relates to an endoscope apparatus comprising a control portion constructed using programmable integrated circuits, the circuit function of each which can be changed.

2. Description of the Related Art

Recently, endoscopes have been widely used in the medical and industrial fields. The endoscope is used in a case where a biopsy or a curing treatment is performed by using a treatment tool as well as to observe or inspect the inside portion of an organism.

Therefore, the endoscope is combined with peripheral units for use in performing observation and treatment, such as a light source unit for supplying irradiation light for observing a subject which is substantially a necessary peripheral unit, an external camera unit for picking up an image, and an electric knife for performing excision.

The foregoing peripheral unit usually consists of the body of the peripheral unit and a control unit to which the body of the peripheral unit is connected, which drives and controls the body of the peripheral unit and which processes signals.

The products of the foregoing peripheral units to be used while being combined with the endoscope are usually in a state where their bodies have different structures and different functions. Therefore, they are usually designed by different designers, and usually different elements are employed. Furthermore, the control units for use together with the bodies of the peripheral units are usually designed by different designers or comprise different elements.

Therefore, if the control units control similar operations, the fact that the control units are designed individually (independently) increases the number of processes for designing the control unit. Thus, there arises a problem in that the cost of the product cannot be reduced. Furthermore, the necessity of disposing similar control circuits for respective peripheral units raises a problem that the size of the apparatus cannot be reduced. When a plurality of peripheral units are used in a combined manner, circuits having functions that are not always required are sometimes undesirably disposed.

Many types of endoscopes and peripheral units, such as light source units and video processors, may form the endoscope apparatus. A consideration will be made about a combination of, for example, an endoscope, a video processor and a light source unit. Endoscopes are arranged to have different outer diameters to be adaptable to the portion for use, such as the upper digestive tube or the lower digestive tube. Also the available video processors have different characteristics. In a case where the different types of endoscopes are used, the characteristics, such as the response speed of the automatic light adjustment function realized when the endoscope and the peripheral units are combined, are changed. Therefore, there is a need for preparing a multiplicity of light source units having different characteristics to be adaptable to the several types of endoscopes and video processors in order to obtain adequate operational characteristics. In this case, a problem of cost reduction arises. In a case where a common light source unit is used when several types of endoscopes and video processors are used, desired characteristics for the endoscope apparatus sometimes cannot be obtained. For example, a desired response speed cannot be realized because the response speed of the automatic light adjustment means is lowered depending upon the combination.

The peripheral unit to be used in combination with the endoscope is designed and adjusted before it is supplied as a product in such a manner that the characteristics of the unit, for example, the characteristics of a light quantity adjustment means of a light source unit, are set to realize the optimum conditions in a state of normal use.

As an example, in an automatic light adjustment means of an endoscope apparatus the light quantity adjustment for observation is performed by a light adjustment means for adjusting the aperture ratio of a diaphragm disposed in an optical path of the light source unit in accordance with the brightness of a subject image obtained through an image pickup means. The loop gain, the response speed and the adjustable range of the automatic light adjustment means are set to be adaptable to a state of normal use. Although portion for controlling each function of the light source unit is formed by using a digital circuit, the circuit function, and the operational characteristics of the control portion have been determined by a fixed circuit structure corresponding to the set value of the operation of each function.

Since the operational characteristics of the unit cannot easily always be set to the optimum state, the optimum setting for a user is not always realized. In this case, the user must adjust the unit to be adaptable to the state of use or to satisfy the desire of the user.

Since the conventional apparatus has been arranged such that the operational characteristics of the apparatus are fixedly set to be adaptable to the state of normal use and they cannot freely be set to be adaptable to other states of use, a problem sometimes arises in that the characteristics, the functions, values of the operational state, the operational characteristics, the adjustable range of each function, and the adjustment steps that are not suitable for the user are set. In addition, there arises a need to perform adjustment or resetting to be adaptable to the state of use or to satisfy the desire of a user. That is, the operational characteristics of the apparatus cannot freely be set to satisfy the desire of a user, to be adaptable to the state of use and the combination of units. Thus, a problem rises in that the apparatus cannot always be used in an optimum state.

SUMMARY OF THE INVENTION

An object of the present invention is to provide an endoscope apparatus utilizing FPGAs, to form a unit for controlling functions of peripheral units for use and required functions, decreasing the number of design processes, reducing the cost of the product, reducing the size of the circuit in the control portion and therefore reducing the size thereof.

Another object of the present invention is to provide an endoscope apparatus having an arrangement where a control portion for only the function of a peripheral unit for use or a required function is selectively constituted by an FPGA or a common control portion is formed by using a common circuit for common contents to be controlled for a plurality of functions so that the control circuit is efficiently formed for only the required function and therefore the size of the apparatus is reduced.

Another object of the present invention is to provide an endoscope apparatus having an arrangement where the structure of a control unit is changed by changing a program of an FPGA to be adaptable to the state of use or combination of units so as to be capable of freely setting the function of the unit, the operational state and the operational characteristics so that the apparatus can always be used in an optimum state.

Another object of the present invention is to provide an endoscope apparatus capable of changing the function of a programmable integrated circuit when necessary even if the apparatus is being operated and reducing the size of a circuit having a desired function by sequentially rewriting the function of the programmable integrated circuit in accordance with a time-sequential process.

An endoscope apparatus according to a preferred exemplary embodiment of the present invention comprises: an endoscope; supply means for supplying a required signal or energy to a peripheral unit relating to the endoscope; and control means for controlling the supply means, wherein the control means includes at least a field programmable gate array, and a function required by at least either the endoscope or the peripheral unit relating to the endoscope is realized by receiving circuit information to selectively write the circuit information on the field programmable gate array so that a control circuit is formed for controlling the supply means.

Other and further objects, features and advantages of the invention will appear more fully from the following description.

BRIEF DESCRIPTION OF THE DRAWINGS

FIGS. 1 to 3 illustrate a first embodiment of the present invention, in which

FIG. 1 is a block diagram which illustrates the structure of an essential portion of an endoscope apparatus;

FIG. 2 is a block diagram which illustrates a first structural example of an output control portion and an input/output connector portion formed in an apparatus body;

FIG. 3 is a block diagram which illustrates a second structural example of an output control portion and an input/output connector portion formed in the apparatus body;

FIGS. 7(a) and 7(b) illustrate a fourth embodiment of the present invention, in which FIG. 7(a) is a block diagram which illustrates a circuit portion of a light adjustment means of an endoscope apparatus which is capable of switching between automatic light adjustment and manual light adjustment;

FIG. 7(b) is an explanatory view which illustrates the configuration of storage areas in a ROM shown in FIG. 7(a);

FIG. 8 is a block diagram which illustrates a structural example of an endoscope apparatus capable of controlling each peripheral unit from the peripheral unit;

FIGS. 10 to 16 illustrate a fifth embodiment of the present invention, in which

FIG. 10 is a block diagram which illustrates the schematic structure of a light source unit disposed in an endoscope apparatus;

FIG. 11 is a block diagram which illustrates the functional structure of a control portion constituting a digital circuit in a control circuit or the like in the light source unit;

FIG. 12 is a block diagram which illustrates the functional structure of a function adjustment means for adjusting each function of the light source unit by a panel operation;

FIG. 13 is an explanatory view which illustrates a structural example of the operation panel of a conventional light source unit;

FIGS. 14, 15 and 16 are explanatory views which illustrate an example of a state of setting made by the operation panel of a light source unit according to a fifth embodiment of the present invention;

FIGS. 23 to 26 illustrate a sixth embodiment of the present invention, in which

FIG. 23 is a block diagram which illustrates the structure of an endoscope apparatus;

FIG. 24 is a block diagram which illustrates the structure of an automatic light adjustment unit according to the sixth embodiment;

FIG. 25 is a structural diagram which illustrates a loop gain calculating circuit formed by a programmable gate array;

FIG. 26 is a structural view which illustrates an automatic light adjustment circuit formed by a programmable gate array;

FIGS. 37 and 38 illustrate a seventh embodiment of the present invention, in which FIG. 37 is a block diagram which illustrates the structure of an endoscope apparatus;

FIG. 38 is a block diagram which illustrates the functional structure of a digital circuit constituted by a programmable gate array in the endoscope apparatus shown in FIG. 37;

DETAILED DESCRIPTION OF THE PREFERRED EMBODIMENTS

Figure 1:
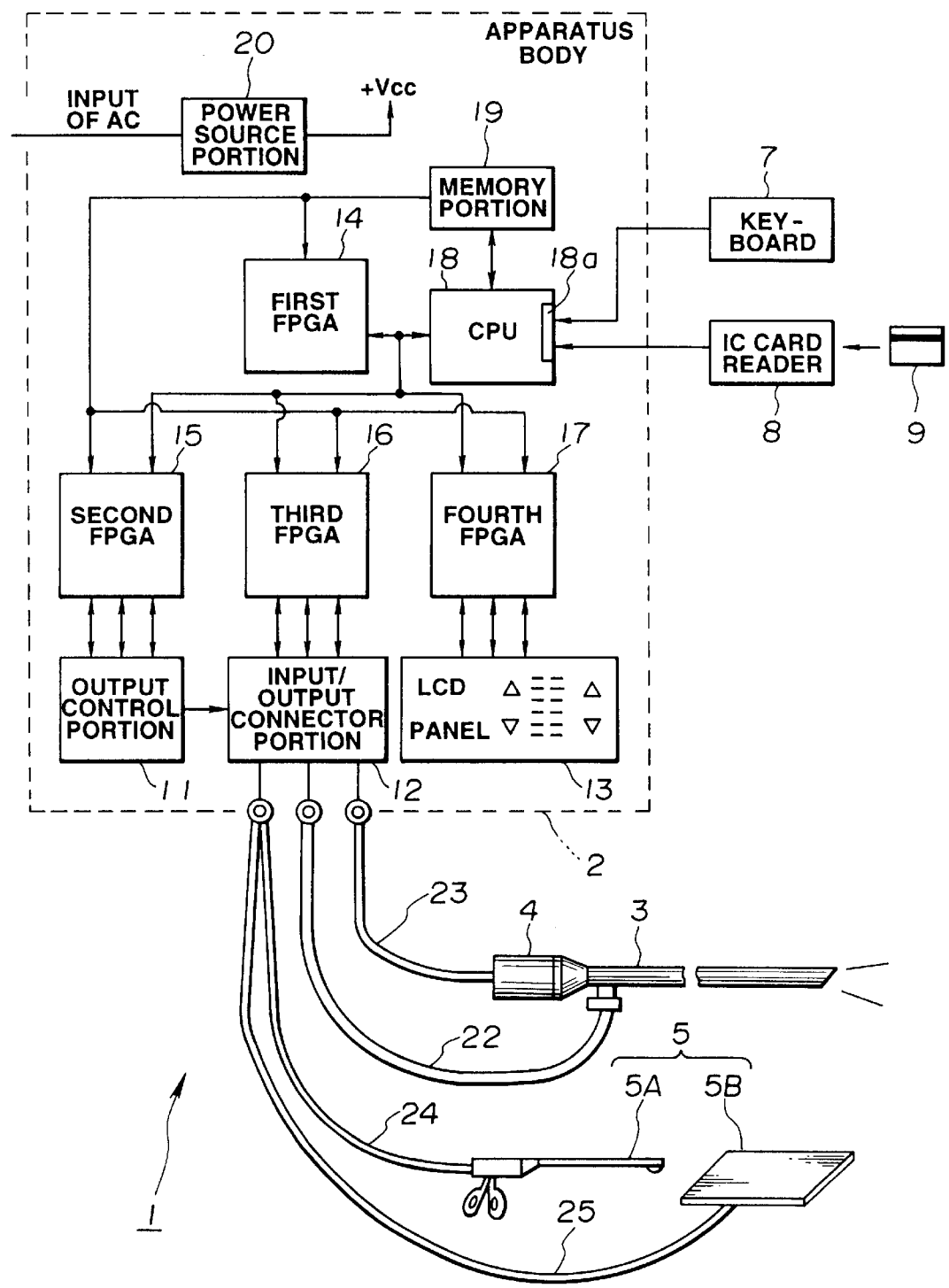
Figure 2:
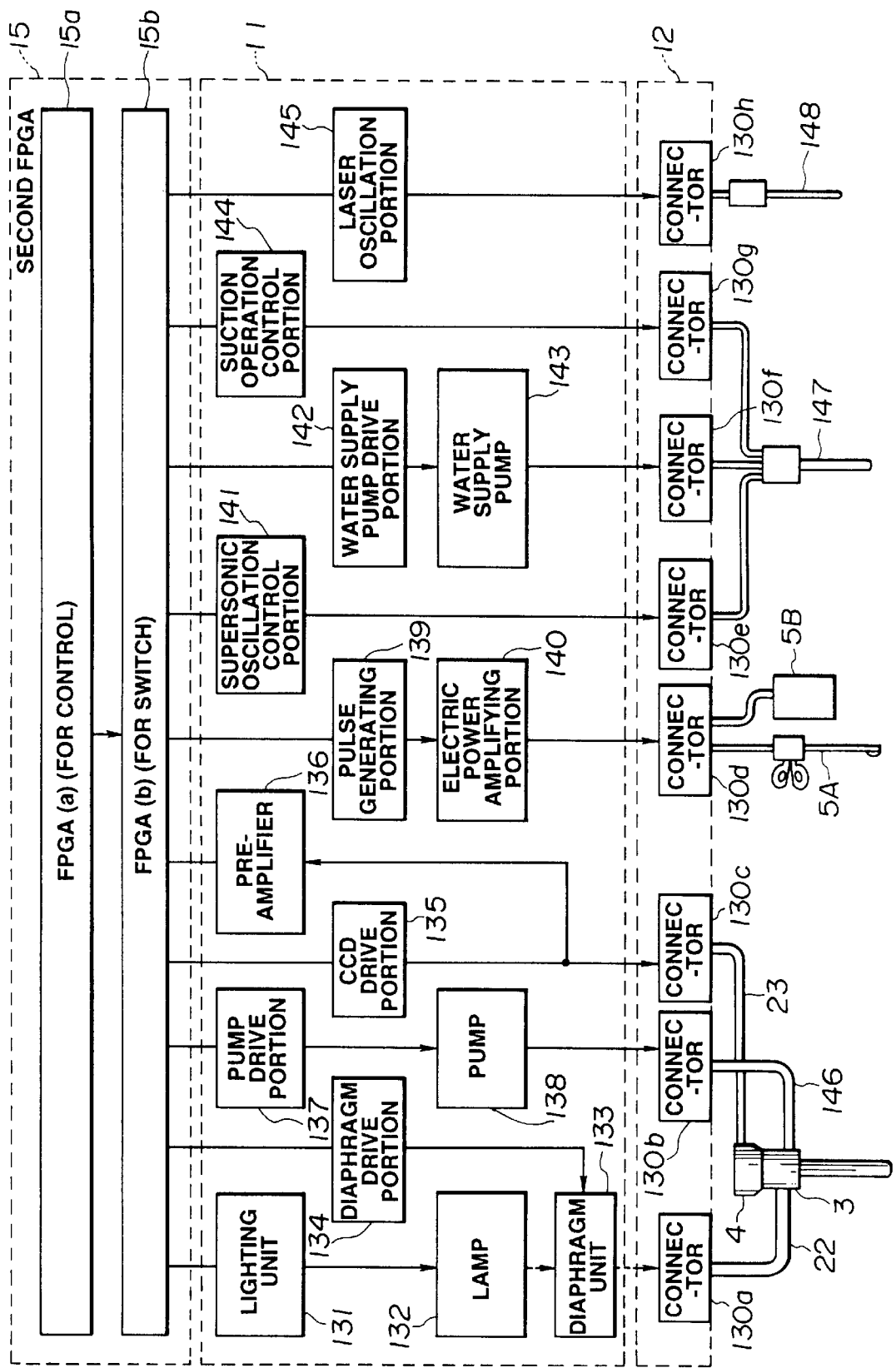
Figure 3:
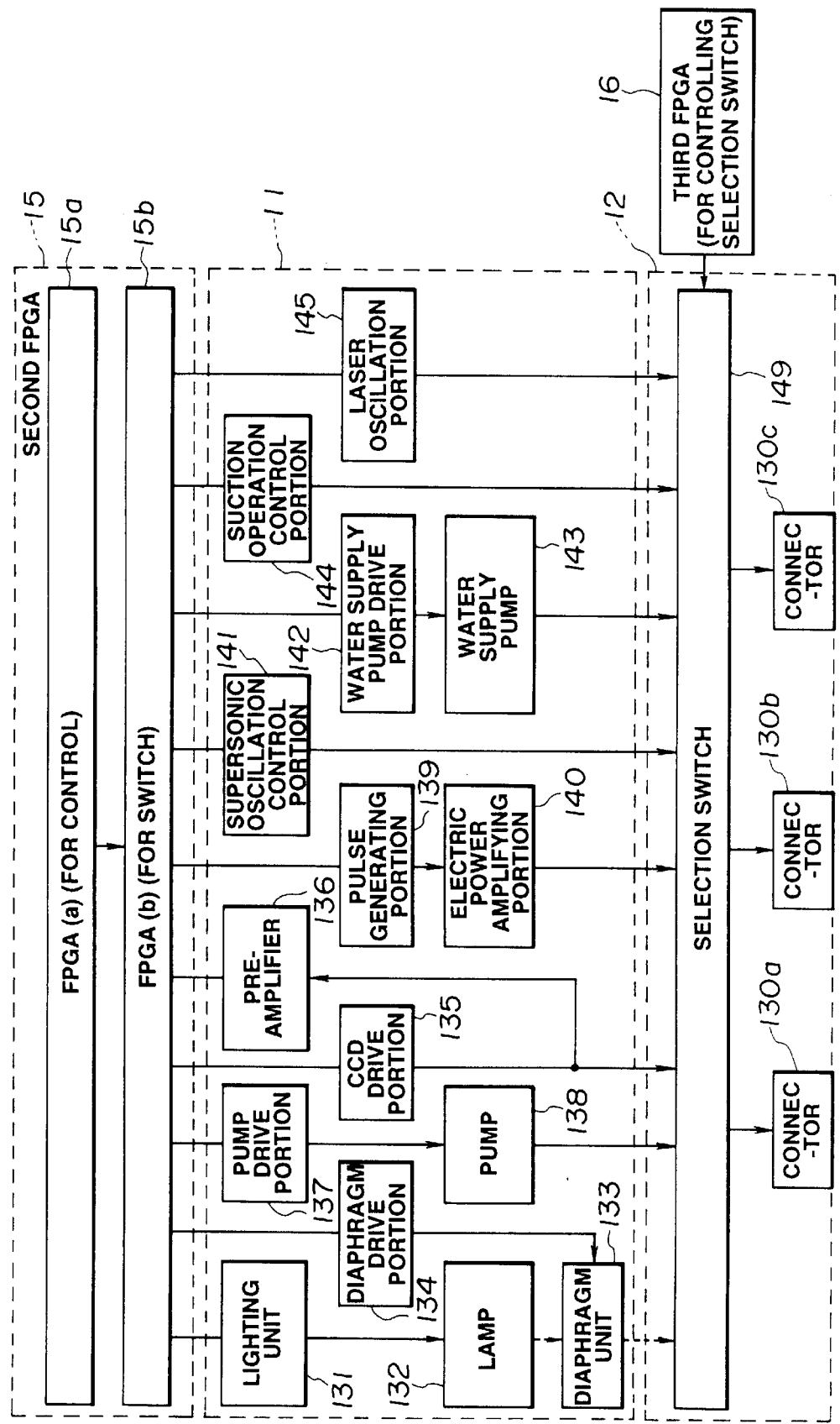

FIGS. 1 to 3 illustrate a first preferred exemplary embodiment of the present invention.

FIG. 1 illustrates the structure of an endoscope apparatus 1 according to a first preferred exemplary embodiment of the present invention. The first embodiment is arranged in such a manner that a field programmable gate array (hereinafter abbreviated to an "FPGA") is used as a programmable integrated circuit, the circuit function of which can be changed, so as to realize functions of a control unit, such as driving, controlling or signal processing that corresponds to a peripheral unit connected to be operated.

The endoscope apparatus 1 comprises an apparatus body 2, an endoscope 3 such as a hard endoscope to be connected to the apparatus body 2, and peripheral units for the endoscope to be used together with the endoscope 3, for example, an external TV camera 4 and curing tools such as an electric knife 5. The electric knife 5 consists of an electric knife body 5A and a P-plate (a patient plate) 5B.

External input means, such as a keyboard 7 and an IC card reader 8, for setting the structure of the apparatus body 2 can be connected to the apparatus body 2. By inputting data through the keyboard 7 or by reading data of setting recorded in an IC card 9 including an IC, such as a RAM in which data has been recorded, with an IC card reader 8 to input the data, structure of the apparatus body 2 can be selected. Although FIG. 1 shows a setting in which the external TV camera 4 and the electric knife unit 5 attached to the endoscope 3 can be used, another structure may be employed in which, for example, only the external camera 4 is connected to the endoscope 3.

The apparatus body 2 according to this embodiment is a universal body, the apparatus body 2 comprising: an output control portion 11 serving as a supply means that has an output portion for transmitting energy for irradiating light to be supplied to the endoscope 3 or a high-frequency electric current to be supplied to the electric knife 5 or an output signal, such as a drive signal to be supplied to the external TV camera 4; an input/output connector portion 12 for establishing connections with the peripheral units; LCD (Liquid Crystal Display) panel portion 13; a first FPGA 14; a second FPGA 15; a third FPGA 16; fourth FPGA 17; a CPU 18; a memory portion 19; and a power source portion 20. At least a portion of the foregoing first FPGA 14, the second FPGA 15, the third FPGA 16 and the fourth FPGA 17 forms a control unit for realizing the required functions of each peripheral unit.

The FPGA, such as the first FPGA 14, is a large-size PLD (Programmable Logic Device) that establishes, with program devices, the connections among logical blocks and lines arranged on a chip to constitute a logic circuit. For example, logical blocks are, in a matrix configuration, disposed in the central portion of the PLD and I/O (Input/Output) blocks are disposed in the peripheral portion. In addition, the internal connection elements are disposed among lines and columns of the logical blocks and among the logical blocks and the I/O blocks.

The functions of the logical blocks and the I/O blocks can be changed in accordance with a program. Also, the state of the internal connection established by the internal connection element can be changed in accordance with the program.

In accordance with a configuration program including circuit information stored in a memory means, such as an included memory, a logical circuit is formed. The configuration program can automatically be loaded from the memory when electric power is supplied or in accordance with a command. It can also be programmed by a microprocessor when, for example, the system is initialized.

The programmable integrated circuit, in which circuit data for defining the connection information and the circuit function, such as the logical function, is preferably stored in a memory cell to be capable of programming required circuit functions, and is able to change the circuit function by rewriting the circuit data. In particular, a satisfactory advantage can be realized when a digital circuit, such as a logical circuit, is designed because the circuit can easily be changed without the need for repeating trials.

Since the digital circuit requires dense integration and size reduction as important factors, a gate array, a standard cell, and a custom IC are usually employed to realize the dense integration. In place of the foregoing gate array, use of the programmable integrated circuit enables a densely-integrated electronic circuit, the circuit function of which can be changed, to be constituted.

Although a PLD (Programmable Logic Device) and a PGA (Programmable Gate Array) have been known as the programmable integrated circuits, this embodiment uses a FPGA (Field Programmable Gate Array (which is a kind of a PGA to constitute the apparatus. The foregoing structure facilitates rewriting of the circuit at the time of design of the circuit as well as the function can easily be changed by only changing the configuration program without the need for changing the structure of the hardware.

The power source portion 20 is formed such that, for example, an AC input is converted into a DC and then a unit, such as a DC-DC converter, is used to provide a standard electric power supply (+5 V, +12 V or −12 V).

The memory of the memory portion 19 stores a program for rewriting each FPGA in order to realize a function selected by the external input means (the keyboard 7 or the IC card 9 through the IC card reader 8).

In place of the input of the instruction of the internal memory portion 19 by using the keyboard 7, another method may be employed in which data of circuit information serving as a configuration program for each FPGA is recorded in the IC card 9 and the program is loaded into each FPGA from the IC card 9.

The CPU 18 includes an interface 18a for receiving data from the foregoing external input means, where the CPU 18 is capable of reading data for setting the control unit from the IC card reader 8.

The input of data for setting the function of the control unit from outside can be performed by means of an external ROM, a floppy disk, an interface GP-IB or an interface RS232C as well as the IC card, which is the external memory.

The first FPGA 14 constitutes a digital signal circuit portion in, for example, a video signal processing circuit and has a function for transmitting a video signal to a color monitor through a D/A converter (omitted from illustration).

The second FPGA 15 constitutes a control portion for controlling the output control portion 11, the second FPGA 15 controlling, for example, a lamp lighting unit of a light source unit disposed in the output control portion 11. The second FPGA is controls a high-frequency amplifying portion disposed in the output control portion 11 and arranged to supply a high-frequency electric current to the electric knife body 5A. In accordance with a program adapted to the second FPGA 15, an output mode setting circuit, and an output waveform selection circuit which are adapted to the electric knife body 5A can freely be constituted.

The third FPGA 16 constitutes a control portion for the input/output connector portion 12 (composed of a relay or the like for switching the signal transmission to plurality of connectors). Referring to FIG. 1, the endoscope 3 is connected to one of the connectors of the input/output connector portion 12 through a light guide cable 22 so that irradiation light is supplied to the light guide of the endoscope 3.

Further, the external TV camera 4 is connected to one of the connectors of the input/output connector portion 12 through a signal cable 23 so that a drive signal is supplied to an image pickup device (omitted from illustration) included in the external TV camera 4. In addition, a video signal read by the image pickup device is transferred to the first FPGA 14 through the third FPGA 16, the video signal being processed in the first FPGA 14 so as to be transmitted to the color monitor through a D/A converter (omitted from illustration).

A pair of connectors of the input/output connector portion 12 are respectively connected to the electric knife body 5A and the P-plate 5B through a high-frequency cable 24 and a P-cord 25, thus enabling an unnecessary texture, such as a polyp, to be excised with the high frequency electric current.

The fourth FPGA 17 serves as a control unit for determining the hardware structure of a display portion and a switch portion of the LCD panel 13.

The LCD panel 13 serves as a key input portion and the display portion such that the LCD panel display can freely be formed to be adaptable to a unit to be used. For example, the key display permits free selection of alphabets, Japanese characters and symbols.

The operation of this embodiment will now be described.

In an initial state, no FPGA forms any functional circuit. The output control portion 11 and the input/output connector portion 12 adapted to a unit intended to be set are connected previously.

Then, key input for instructing reading of a program through the keyboard 7 or use of the IC card 9 having similar information recorded thereto causes the program for constituting, with the FPGA, a circuit of a control unit adaptable to the unit to be connected to be supplied from the ROM of the memory portion 19. In this case, the program for constituting the circuit with the FPGA may be supplied by the external input means in place of the ROM of the memory portion 19.

The CPU 18 decrypts the program to rewrite each FPGA to circuits adaptable to the control units intended to be set. As a result of the foregoing operation, the apparatus body 2 is set to a desired control unit so as to drive and control the connected unit and perform the signal processing.

According to the foregoing structure, all hardware units except the output control portion 11 and the input/output connector portion 12 can be commonly used. Therefore, the need for designing a control unit for each peripheral unit having each function can be eliminated, thus enabling the number of design processes to be decreased. Since the display on the LCD panel 13 can freely be set to the Japanese characters, Alphabets or symbol characters in accordance with the program, common use of elements can be realized.

Moreover, the necessity lies in that only the control unit corresponding to the peripheral unit intended to be used is constituted with the FPGA. Therefore, rewriting of the FPGA at the time of using another peripheral unit enables the structure of the control unit to be changed. Thus, the size of the apparatus can be reduced.

If the functional change of the apparatus body 2 is required, change relating to the hardware structure can be performed only by changing the program constituting the FPGA. Therefore, the necessity of changing the elements can be eliminated when the design is changed and the common use of the elements can be realized, thus providing a cost-reducing effect. Therefore, the apparatus can be provided with a low cost. If the specifications of the apparatus are changed such that the characteristics and the functions are varied and the characteristics of the control unit are changed to correspond to several types of peripheral units each having different characteristics, the foregoing structure is adaptable by only changing the program while using the same common hardware.

As described above, according to the structure of this embodiment, the control function adaptable to the connected peripheral unit can be constituted by the FPGA. Therefore, the required functions can be realized by the common unit and, accordingly, the size of the apparatus can be reduced while decreasing the number of design processes. Hence, a plurality of required functions can be realized by a single common hardware structure without a necessity of enlarging the size of the apparatus. As a result, the size and the cost of the apparatus can be reduced.

An example of the internal structure of the output control portion 11 and the input/output connector portion 12 of the apparatus body 2 will now be described as well as making a detailed description of the state of the connections established among the output control portion 11, the input/output connector portion 12 and the FPGA. FIG. 2 illustrates a first structural example of the output control portion and the input/output connector portion.

The first structural example has an arrangement in which the third FPGA 16 is not used. The second FPGA 15 consists of a FPGA (a) 15a for constituting a control circuit and a FPGA (b) 15b for constituting a switching circuit. The output control portion 11 has, when viewed from the left portion of FIG. 2, a function possessed by the light source unit, a function possessed by a camera control unit (hereinafter called a "CCU"), a function possessed by the electric knife unit, a function possessed by an ultrasonic operation unit (hereinafter called a "USU"), and a function possessed by a laser beam unit so as to generate energy (light beams, supersonic waves and high-frequency electric currents) or a signal for each function.

The input/output connector portion 12 has connectors 130a to 130h adaptable to the connectors of the respective peripheral units (the endoscope, the TV camera, the curing probe, and the curing tool), thus enabling the peripheral units to be connected to the foregoing connectors.

As the function of the light source unit, the output control portion 11 has, as the light source portion, a lighting unit 131, a lamp 132, a diaphragm unit 133 and a diaphragm drive portion 134. Furthermore, the light guide cable 22 of the endoscope 3 can be connected to the connector 130a. When the lamp 132 is switched on by the lighting unit 131, irradiation light is emitted, and as well as the diaphragm drive portion 134 opens/closes the diaphragm unit 133 disposed in the light passage for the irradiation light so that the quantity of light emitted into the light guide is controlled.

As the functions of the CCU, the output control portion 11 is provided with a CCD drive portion 135 for transmitting/receiving a drive signal and an image signal to and from the image pickup device of the external TV camera 4 and a pre-amplifier 136. In addition, the output control portion 11 is provided with a pump drive portion 137 and a pump 138 of a fluid control unit. The signal cable 23 of the external TV camera 4 is connected to the connector 130c, while a fluid passage 146 for supplying air, water or the like and extending from the endoscope 3 is connected to the connector 130b. Thus, the air supply operation, the water supply operation and the external TV camera 4 can be controlled while operating the endoscope 3.

As the function of the electric knife unit, the output control portion 11 has a pulse generating portion 139 and an electric power amplifying portion 140 serving as a high-frequency amplifying portion for generating a high frequency electric current. The electric knife body 5A and the P-plate 5B can be connected to the connector 130d, thus enabling the electric knife body 5A to be supplied with high-frequency electric current energy to perform a treatment of excising an organic texture.

As the function of the USU, the output control portion 11 is provided with a supersonic wave oscillation control portion 141, a water supply pump drive portion 142, a water supply pump 143 and a suction operation control portion 144. Furthermore, a supersonic wave operation probe 147 is connected through the connectors 130e, 130f and 130g so as to enable cauterization using supersonic waves, water supply and suction of organic texture to be performed by using the supersonic wave operation probe 147.

As the function of the laser beam unit, the output control portion 11 is provided with a laser beam oscillation portion 145. Furthermore, a laser probe 148 can be connected to the connector 130h so that the laser beams are supplied to the laser probe 148 to perform cauterization by using laser beams.

In the FPGA (a) 15(a), a control circuit for, under control of the CPU 18 in accordance with the configuration program supplied from the memory portion 19, controlling each supply means of a selected function among the function blocks of the output control portion 11, for example, the function of the light source unit, the function of the CCU, the function of the electric knife unit and the function of the USU.

In the FPGA (b) 15b, a line is formed for establishing the connection between an output from the control FPGA (a) 15a and input portion of the supply means of the selected function in the output control portion 11 so as to switch selection of a control signal between the FPGA (a) 15a and the supply means of each function in the output control portion 11.

As a result of the structure above, the supply means of the selected function in the output control portion 11 is controlled by the second FPGA so that the peripheral unit connected to the supply means is driven and controlled to realize the function of the connected peripheral unit.

FIG. 3 illustrates a second structural example of the output control portion and the input/output connector portion.

The second structural example has an arrangement such that the same connector is used as connectors among connectors for connecting each peripheral unit of a type capable of having a common shape, for example, connectors for transmitting the same energy (light, electric power or gas) so as to use the common connector. Furthermore, the structure is formed such that the input/output connector portion 12 is controlled by using the third FPGA 16.

The input/output connector portion 12 is provided with a switch 149 that establishes the selective connection between the output from the supply means for each function provided in the output control portion 11 and the connectors 130a to 130c, the switch 149 being formed by relays and switches. The control portion constituted in the third FPGA 16 controls switching. The residual structures are the same as those of the first structural example shown in FIG. 2.

The foregoing structure has an arrangement in which the control performed by the third FPGA 16 changes over the switch 149 so as to cause the output from the supply means of the selected function in the output control portion 11 to be transmitted to the connectors 130a to 130c so that each function of the peripheral units connected to the connectors 130a to 130c is realized.

The required functions of each peripheral unit for use in relation to the endoscope of the endoscope apparatus are limited depending upon the inspection or the treatment to be performed. For example, the functions of the light source unit are exemplified by an irradiation function, a light adjustment function, a function for controlling a rotary filter thereof, a function for controlling exposure at the time of photography, and an air-supply function. However, all of the foregoing functions are not required depending upon combination of units and upon the state of use.

For example, inspection of the upper alimentary canal using the endoscope requires the irradiation function, the light adjustment function and the air-supply function to be selected and executed as the functions of the light source unit. In a case where a photographing unit is connected for use as a recording unit, the exposure control function is further required as the function of the light source unit. In addition, a CCU serving as an observing unit is required as the further peripheral unit. As a treatment unit, an electric knife is used.

When the trachea is inspected by using the endoscope, the light source unit must have the irradiation function and the light adjustment function. Further, a CCU is required to serve as an observing unit, and a laser beam unit is used as the treatment unit.

In a case where a surgical operation is performed in a state where a laparoscope is used, the light source unit must have the irradiation function and the light adjustment function while requiring a CCU as the observing unit. In this case, an electric knife or a USU is used as the treatment unit.

As described above, different functions are required depending upon the inspection and the treatment. If the control units are provided to correspond to the respective functions and the peripheral units, the design process becomes increased excessively and the size of the apparatus cannot be reduced. However, the structure of this embodiment enables the control units for only the functions of the employed peripheral units or required functions to be selectively constituted with the FPGA. The control units for the functions that are not required depending upon the state of use are not constituted. Therefore, the size of the circuit in the control portion can be reduced. In an example case where a plurality of peripheral units have the common contents to be controlled, the common contents to be controlled for the several functions can be realized by a common circuit so that a common circuit unit is constituted. Therefore, the control circuits can efficiently be constituted for only the required functions, thus reducing the size of the apparatus. If the program of the FPGA is changed to change the structure of the control unit, a variety of connections with a variety of peripheral units can be established.

In the first embodiment, instruction or selection must be performed through the keyboard 7 in order to constitute a control unit adaptable to a unit connected to the apparatus body 2 to be used. As an alternative to this, an arrangement may be employed in which a peripheral unit to be connected is detected, and the control unit corresponding to the connected unit is constituted.

Although the first embodiment has an arrangement in which the apparatus body 2 has the functions of the control units corresponding to the plurality of the connected peripheral units, the arrangement is not limited to that in which the functions of the control units are realized for all of the plurality of the connected peripheral units. A structure may be employed in which a portion of peripheral units each having the function of the control unit is connected to the apparatus body 2.

As contrasted with the structure shown in FIG. 1 in which the external TV camera 4 is connected to the apparatus body 2 and the apparatus body 2 has the function of the control unit for the external TV camera 4, the external TV camera 4 may be connected to the apparatus body 2 through a CCU serving as the control unit for the external TV camera 4.

The endoscope apparatus sometimes encounters a fact such that peripheral units connected to the apparatus body and the apparatus body 2 act in a combined manner. For example, since the automatic light adjustment function of the light source unit is activated in response to an output signal from a TV camera or an output signal from a CCU, the automatic light adjustment function is affected by the characteristics of another connected unit or the control unit.

Even if the same type units (for example, TV cameras) or units (for example, CCUs) of the same type are connected as is done with the automatic light adjustment function, the characteristics are sometimes different from each other. If the functions, which are suitable for the connected units or the apparatuses, can be realized in the foregoing case, lowering of the response speed can be prevented. However, an endoscope apparatus having the functions, the characteristics of which are different from one another, are realized by combining the foregoing units raises a risk that a circuit which cannot satisfactorily exhibit the performance thereof is constituted. What is worse, performance is limited if the units that can be used are extended.

Accordingly, a second embodiment will now be described in which the endoscope apparatus has a structure such that the automatic light adjustment function thereof is able to extremely exhibit the performance regardless of the combination.

Figure 4:
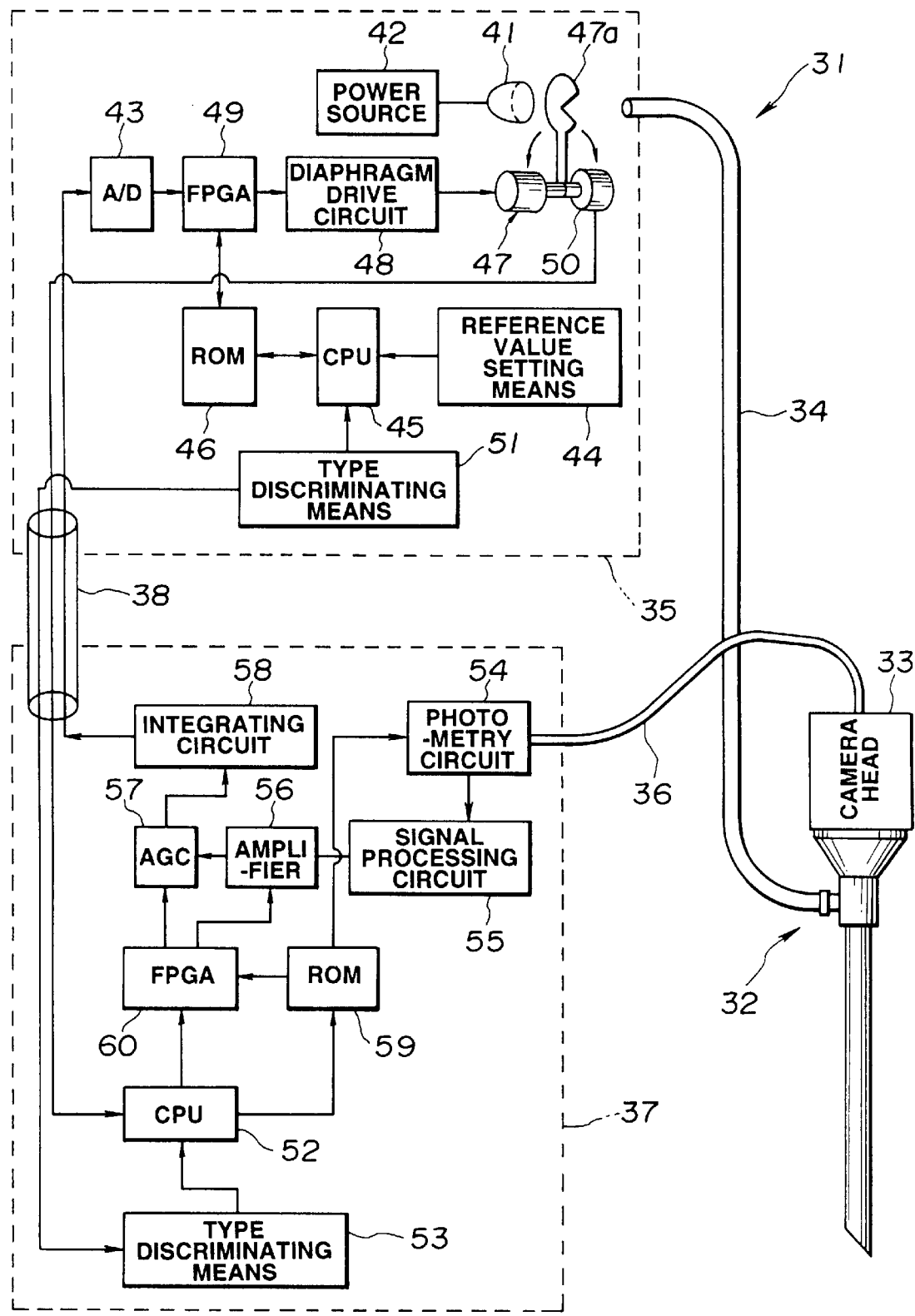
FIG. 4 is a block diagram which illustrates the structure of an essential portion of an endoscope apparatus according to a second embodiment of the present invention.

An endoscope apparatus 31 according to the second embodiment shown in FIG. 4 comprises a hard endoscope 32, a (external) camera head 33 to be attached to the hard endoscope 32, a light source unit 35 to which a light guide cable 34 to be connected to the hard endoscope 32 is attached, and an (external camera) CCU 37 to which a signal cable 36 of the camera head 33 is connected and which performs a signal processing of the image pickup device in the camera head 33. The light source unit 35 and the CCU 37 are detachably connected to each other through a signal transmission line 38.

The light source unit 35 shown in FIG. 4 corresponds to the light source unit portion of the apparatus body 2 according to the first embodiment shown in FIG. 1. The residual portions of the functions for connecting the electric knife and for performing the drive and control of the same are omitted here.

The light source unit 35 comprises: a lamp 41 for supplying irradiation light to the light guide cable 34; a power supply circuit 42 for lighting the lamp 41; an A/D converter 43 for converting a brightness signal representing the brightness of a subject transmitted from the CCU 37 from an analog signal to a digital signal in response to an output signal from the camera head 33; a ROM 46 for transmitting a reference value under control of a CPU 45 in accordance with a reference value of an automatic light adjustment level of the light source unit 35 previously set by a reference-value setting means 44; and an FPGA 49 having a digital circuit constituted by a servo circuit that supplies a control signal to a diaphragm drive circuit 48 that subjects the reference value transmitted from the ROM 46 and the brightness signal supplied from the CCU 37 to a comparison to drive a diaphragming blade 47a of a diaphragm unit 47.

The diaphragm unit 47 comprises: the diaphragming blade 47a; a motor for rotating the diaphragming blade 47a;

and so forth. The position of rotation of the diaphragming blade 47a is converted into position signal POT by a potentiometer 50 before it is transmitted. The output from the potentiometer 50 is connected to a CPU 52 in the CCU 37 for controlling the camera head 33 so that the position signal POT is received by the CPU 52. Light emitted from the lamp 41 is allowed to pass through the diaphragming blade 47a and is transmitted to the light guide cable 34 for supplying light to the hard endoscope 32.

The light source unit 35 has a type discriminating means 51 for recognizing the characteristics (the serve characteristics) of the CCU 37 and the camera head 33 connected to the light source unit 35. Also the CCU 37 has a type discriminating means having a similar function. The type discriminating means respectively are connected to the CPUs of the corresponding units.

The structure of the CCU 37 will now be described. The CCU 37 comprises: a photometry circuit 54 for converting a signal obtained from the camera head 33 including an image pickup device for picking up an image obtained by the hard endoscope 32; a signal processing circuit 55 for processing a photometry signal and a video signal which are outputs from the photometry circuit 54; an amplifier 56 for amplifying an output signal from the signal processing circuit 55; and an AGC (Automatic Gain Control circuit) 57 for automatically amplifying the video signal when the level of the brightness signal is low.

The brightness signal allowed to pass through the AGC 57 is integrated by an integrating circuit 58 so as to be converted into a DC signal, the output signal from the integrating circuit 58 being received by an A/D converter 43 of the light source unit 35.

The CCU 37 comprises the CPU 52 that controls the photometry method (the average photometry, the peak photometry and the partial photometry) and the servo characteristics of the photometry circuit. The CCU 37 has a structure in which some types of the servo characteristics are stored in a ROM 59 and the constants are switched by an FPGA 60.

The operation of the second embodiment will now be described.

When the light source unit 35 and the CCU 37 are connected to each other, the mutual type discriminating means recognize the servo characteristics of the types to read the adequate response speed and the light adjustment accuracy for the automatic light adjustment from the ROMs 46 and 59 in order to again constitute the circuit structures in the FPGAs 49 and 60. As a result, a light adjustment circuit can automatically be constituted from which the optimum servo characteristics are attained by the combination of the light source unit and the CCU.

The conventional apparatus must be designed to cause the units or the apparatuses to be combined to be adaptable to the fixed light adjustment circuit whenever the design is performed. What is worse, the number of the design processes are too large and the realized light adjustment performance is limited by a certain unit. Therefore, it has been impossible to attain ideal characteristics. On the other hand, this embodiment provides an effect of overcoming the foregoing problems and automatically realizing a light adjustment system exhibiting satisfactory performance.

Although the range in which the FPGA can be utilized is limited to a portion of the light adjustment circuit, all circuits except the CPU and the ROM, may, of course, be replaced by the FPGA.

Figure 5:
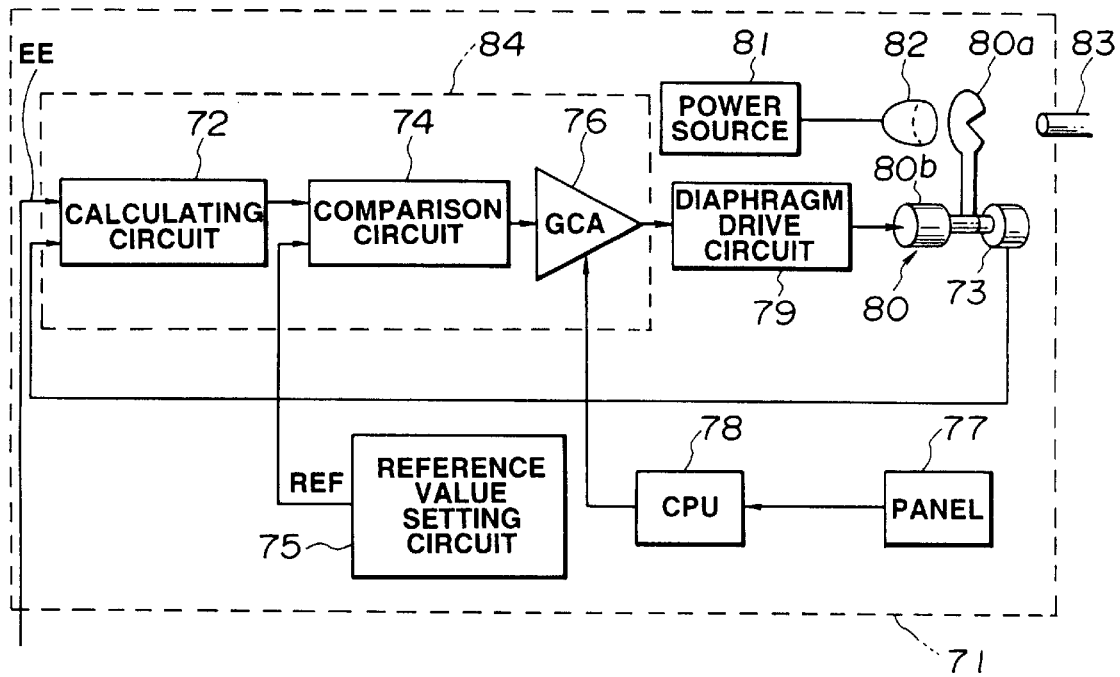
FIG. 5 is a block diagram which illustrates the structure of a light source unit of an endoscope apparatus according to a third embodiment of the present invention.

FIG. 5 illustrates a third embodiment of the present invention while showing the structure of a light source unit of an endoscope apparatus. This embodiment is arranged such that the light adjustment speed can freely be set by a user. The same elements as those of the second embodiment are given the same reference numerals.

The light source unit 71 according to the third embodiment receives a light adjusting brightness signal EE representing the brightness of the subject transmitted from the CCU or a video processor, the brightness signal EE being received by a calculating circuit 72. In the calculating circuit 72, a calculation is performed such that the brightness signal EE is converted into a brightness signal suitable for the quantity of diaphragm by a calculation using a diaphragm positional signal POT supplied from the potentiometer 73. Then, the brightness signal is received by a comparison circuit 74.

The comparison circuit 74 also receives reference value REF supplied from a reference value setting circuit 75 as well as receiving the output from the calculating circuit 72. Thus, a difference signal is obtained in the comparison circuit 74 so as to be supplied to a GCA (Gain Control Amplifier) 76. The gain control terminal of the GCA 76, through a CPU 78, receives an instruction signal transmitted due to the operation of a panel 77. In response to the instruction signal, the gain of the GCA 76 is controlled.

The output signal from the GCA 76 is, through a diaphragm drive circuit 79, supplied to a diaphragming motor 80b that forms a diaphragm 80 so as to operate the motor 80b for rotating the diaphragming blade 80a.

The diaphragming blade 80a changes the quantity of shielding the light from the lamp 82 (which emits light when electric power is supplied from a light source circuit 81) in accordance with the angle of rotation so as to vary the quantity of light for use to irradiate a light guide connector 83 attached to the front portion of the light passage. That is, an automatic light adjustment circuit for automatically controlling the irradiation light quantity in response to the brightness signal EE is formed.

This embodiment is characterized in that the gain of the GCA 76 can be varied by the operation of the panel 77 and a loop gain varying means is provided with which a user is able to vary the loop gain of the automatic light adjustment.

The loop gain varying means is formed such that a gain control amplifier (GCA) is disposed in the automatic light adjustment circuit at a position during a line for transmitting a diaphragm drive signal to switch the gain of the GCA 76 in accordance with the operation performed through the panel 77. The GCA 76 is set such that a loop gain, which does not generate hunting, is realized when the GCA 76 is switched to have the maximum gain, the GCA 76 being acted by the operation through the panel 77 in a direction in which the loop gain is lowered, that is, the response speed is lowered.

Namely, when a user operates the key of the panel 77 in a direction in which the light adjustment response speed is lowered, a pulse signal transmitted from the panel 77 causes the CPU 78 to transmit a gain switch signal to the GCA 76 so as to lower the gain. The user is required to observe the light adjustment response speed displayed on the screen and stop the key operation when adequate speed has been realized.

Thus, the adequate response speed can arbitrarily be lowered and the light adjustment response speed that can easily be observed by the user having respective skill can be realized.

The structure shown in FIG. 5 may be arranged in such a manner that the calculating circuit 72, the comparison circuit 74 and the GCA 76 are constituted by the FPGA 84. Also this embodiment enables a structure to be realized in which a portion of the apparatus body except the portion of the light source unit 71 has an input/output connector portion for connecting an electric knife or a control function corresponding to it.

Figure 6:
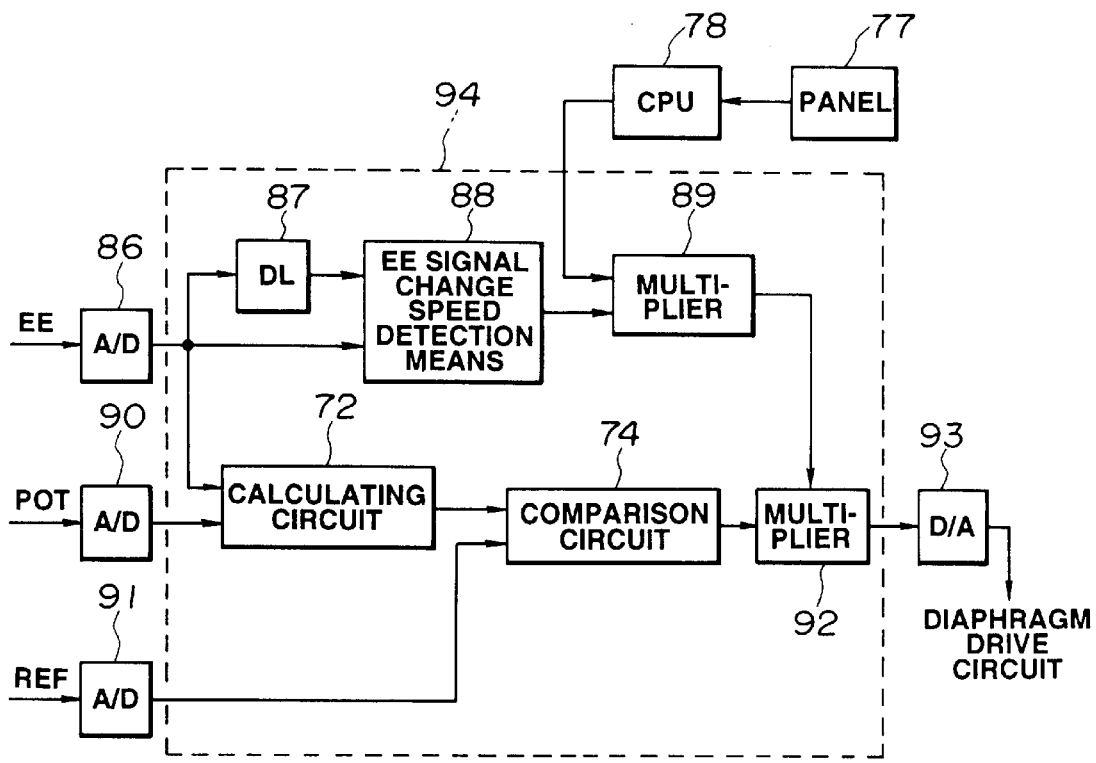
FIG. 6 is a block diagram which illustrates a modification of a light source unit according to the third embodiment.

FIG. 6 illustrates a modification of the light source unit according to the third embodiment. This modification has an arrangement in which the analog brightness signal EE is converted into a digital signal by an A/D converter 86, and then the digital signal is directly supplied to an EE signal change speed detection means 88 through a delay line 87. Thus, the change speed of the brightness signal EE can be detected. The output signal from the EE signal change speed detection means 88 is supplied to a multiplier 89 for changing the gain in accordance with the change speed so as to be multiplied by multiplication data transmitted from the CPU 78 in response to an instruction signal transmitted from the panel 77 before it is transmitted.

The diaphragm position signal POT is converted into a digital signal by an A/D converter 90, and then it is supplied by the calculating circuit 72 so as to be subjected to a calculation in which it is converted into a brightness signal suitable for the quantity of diaphragm on the basis of the brightness signal EE and the diaphragm position signal POT, the brightness signal being supplied to the comparison circuit 74. The reference signal REF is converted into a digital signal by an A/D converter 91 so as to be supplied to the foregoing comparison circuit 74 so that a difference signal between the output from the calculating circuit 72 and the reference signal REF is generated so as to be supplied to a multiplier 92.

The multiplier 92 also receives an output signal from the multiplier 89 to multiply the foregoing difference signal and an output signal from the multiplier 89 with each other, the result of the multiplication being allowed to pass through a D/A converter 93 so as to be converted into an analog signal before it is transmitted to the diaphragm drive circuit 79 shown in FIG. 5. In this structural example, a portion surrounded by a dashed line as shown in FIG. 6 is formed by, for example, a FPGA 94. The CPU 78 and the operating portion for the panel 77 may collectively be formed by the FPGA.

This modification is provided with a function of setting an adequate response speed in a normal state in addition to the functions of the third embodiment. The difference between the present value of the EE signal and the past value through the delay line 87 is used to detect the change speed of the EE signal. The multiplier factor for use in the multiplier 92 is so changed that the gain can be changed in accordance with the change speed. If the change speed is too high, the gain is restricted and the gain is raised if the change speed is too low so that an adequate operation speed is always realized.

When an instruction of limiting the response speed to lower the response speed is made by a user through the panel 77, the CPU 78 transmits multiplier data corresponding to the foregoing instruction to multiply this and the output signal from the EE signal change speed detection means 88. Thus, a light adjustment speed desired by a user can be set.

This modification provides an effect similar to that obtainable from the third embodiment and an adequate response speed can be maintained in a usual state.

Figure 7A:
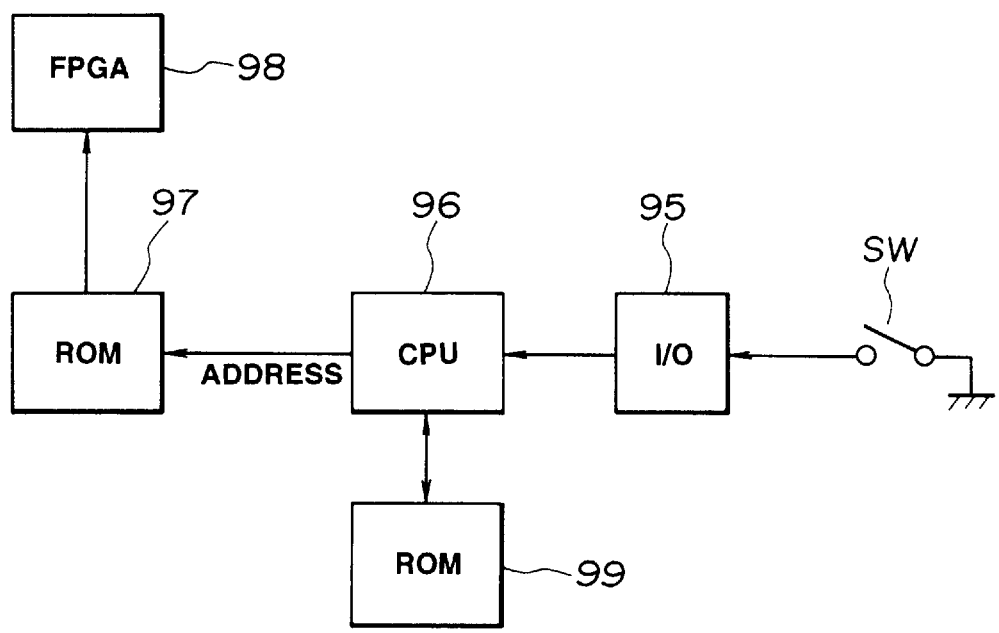
Figure 7B:
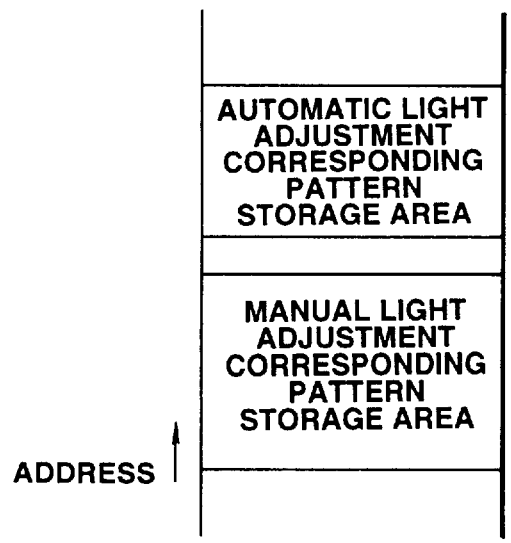

With reference to FIGS. 7(a) and 7(b), a fourth embodiment will now be described. This embodiment has a function capable of switching automatic light adjustment and manual light adjustment.

The endoscope apparatus according to the fourth embodiment is characterized by comprising: a storage device including function defining data for realizing the automatic light adjustment and function defining data for realizing the manual light adjustment; a programmable integrated circuit, the function of which is defined in accordance with data written on a memory cell; and light adjustment selection means for selecting whether the light adjustment operation is performed automatically or manually. Furthermore, means is provided which sets corresponding function defining data from the storage device into the programmable integrated circuit in response to an automatic/manual signal supplied from the light adjustment selection means.

For example, a signal supplied from an automatic light adjustment/manual light adjustment means (for example, a switch) disposed in the light source unit of the endoscope apparatus is read by a CPU for totally controlling the apparatus. In response to the read signal, a discrimination is made whether or not the present setting is made to the automatic light adjustment or the manual light adjustment. If the setting (whether the automatic light adjustment or the manual light adjustment is set) is different from the setting which has been employed, corresponding function defining data in the storage device (a ROM) for defining the function is written on a storage region (a memory cell) of the programmable integrated circuit. Thus, different functions can be realized by switching on the same hardware. In this case, numerals are treated in the form of digital values so that adaptation to the present characteristics can be realized without a risk of scattering.

FIG. 7(a) illustrates the structure of a circuit portion of a light adjustment means enabled to switch the automatic light adjustment and the manual light adjustment. A selection signal (ON/OFF signal) for selecting the automatic light adjustment or the manual light adjustment realized by the automatic/manual selection switch is received by a CPU 96 through an I/O 95. The CPU 96 generates different address signals in response to the selection signal, the address signal being then supplied to a ROM 97. Thus, circuit data of an area, in which the corresponding light adjustment pattern is stored, is read, the read circuit data being transmitted to an FPGA 98.

The FPGA 98 constitutes a circuit for the automatic light adjustment or a circuit for the manual light adjustment in accordance with the circuit data. Note that the program for operating the CPU 96 is stored in a ROM 99.

FIG. 7(b) illustrates the configuration of the storage areas in the ROM 97. That is, the automatic light adjustment corresponding pattern and the manual light adjustment corresponding pattern are stored in regions having different addresses.

As contrasted with the conventional apparatus in which the automatic light adjustment and the manual light adjustment require corresponding control circuits, this embodiment has an arrangement in which the two control circuit are constituted by one FPGA 98 and the respective circuit data is stored in one ROM 97. Therefore, the size of the circuit and the cost can be reduced.

The ROM 99 and the ROM 97 may be formed by one ROM.

When a diagnosis or curing treatment is performed with an endoscope of the conventional endoscope apparatus, the component units forming the endoscope apparatus, such as the light source unit, the video signal processing unit, and the electric knife unit are usually collectively placed in a rack to form the endoscope apparatus or racks on which the foregoing units are mounted are combined to each other at the time of diagnosis.

However, in the case where the component units are mounted on the conventional racks, the number of the racks increases excessively if the number of the component units increases. Thus, the configuration of the racks determines the operationality and the configuration method has not been determined. Therefore, it has been very difficult to realize the optimum state of use.

It might therefore be considered feasible to employ a structure in which the respective units forming the endoscope apparatus are connected to one another by interfaces, and a control computer for controlling the units and operation computer for collectively operating the units are disposed to collectively dispose the respective units. With the foregoing structure, the control computer controls each unit and the operation of the operation computer enables the operation of each unit to be collectively operated so that an endoscope apparatus that can easily be operated is realized.

Although the endoscope apparatus having the structure comprising the control computer is very effective when a large number of component units are used, there arises a problem in terms of configuration in a case where a small number of units are used in that the number of the component units cannot be decreased because of use of the control computer and the operation computer.

In order to overcome the foregoing problem, an example of the structure of an endoscope apparatus is shown in FIG. 8, the structure having an arrangement in which each of the peripheral units forming the endoscope apparatus has a control means capable of controlling the peripheral unit and all of connect component units so that the system can totally be controlled by one component unit regardless of the method of combination of the component units.

An endoscope apparatus 101 shown in FIG. 8 comprises an endoscope 102, a light source unit 103A for use together with the endoscope 102, a video signal processing unit 103B, electric knife unit 103C and so forth. The component units 103I (I=A, B, C, . . . ) have corresponding control means (computers) 104$i$ (i=a, b, c, d, . . . ) for controlling the corresponding component unit and all component units. Furthermore, each of the control means 104$i$ has an operation panel 105$i$ arranged to collectively operate the respective units and is formed by a touch panel.

The operation panel 105$i$ comprises transparent electrodes and a multiplicity of switches disposed in a matrix configuration, the operation panel 105$i$ being arranged such that the coordinates of the depressed switch can be detected by scanning performed by a scanning means in the X (the horizontal) direction and the Y (the vertical) direction. The depressed portion in the operation panel is detected and the coordinate data is received by a control means (the computer) 104$i$.

In an example case where the video signal processing unit 103B is operated by using the touch panel of the light source unit 103A, the control means in the light source unit 103A changes the image displayed on the touch panel of the light source unit 103A into an image to be displayed for operating the video signal processing unit 103B in accordance with the depressed switch on the touch panel. Furthermore, the control means switches the light source unit control mode to the video signal processing unit control mode. By a similar method, the electric knife unit 103C can be operated from the light source unit 103A. In addition, another unit can also be operated similarly.

Figure 9:
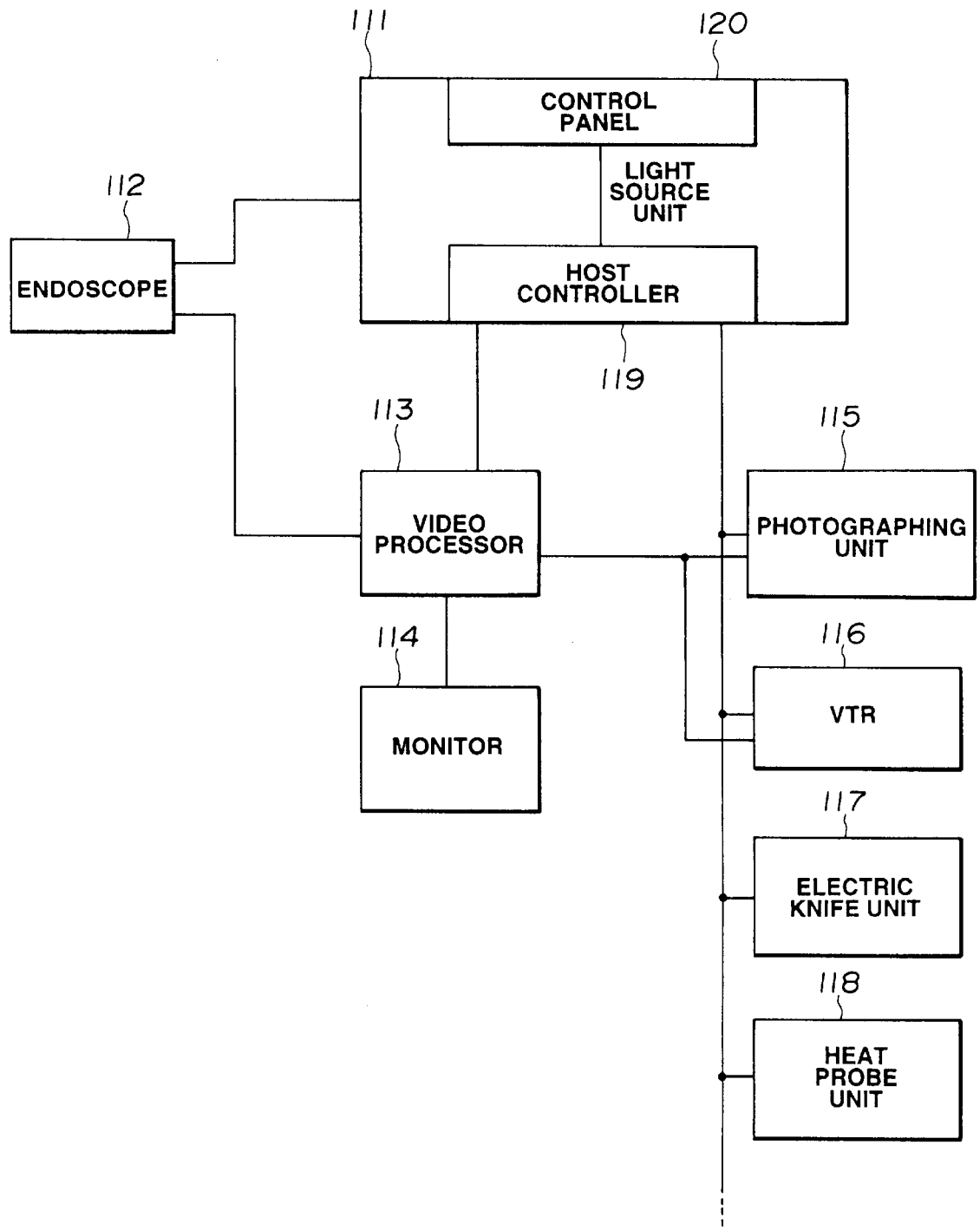
FIG. 9 is a block diagram which illustrates a modification of the endoscope apparatus shown in FIG. 8.

FIG. 9 is a block diagram illustrating a modification of the endoscope apparatus shown in FIG. 8.

The endoscope apparatus according to this modification has the arrangement that the following units are connected to a light source unit 111 to be connected to a endoscope 112: a video processor 113 for forming an image obtained from the endoscope 112 into a video image; a photographing unit 115 for recording the image obtained by the endoscope 112 as a still image; a VTR 116 for recording the image obtained by the endoscope 112 as a moving image; an electric knife unit 117 for use to cure a subject of inspection (a patient); and a heat probe unit 118. A host controller 119 for concentrically controlling the foregoing units is disposed in the light source unit 111. Furthermore, a monitor 114 is connected to the video processor 113.

The light source unit 111 is provided with an operation panel 120 forming a concentric operation portion having an operation screen display portion consisting of a liquid crystal display or the like for displaying the operation switches, and an input detection portion comprising a touch panel disposed on the operation screen display portion.

On the operation screen display portion of the operation panel 120, symbols showing the corresponding component units are always displayed. When the symbol is touched, the input detection portion transmits a signal to the host controller 119 so that the unit corresponding to the touched symbol is controlled. The host controller 119 transmits a signal to the selected unit through the interface so as to cause the unit to be a waiting mode in which the function of the unit can be adjusted. Also the operation screen display portion is controlled to correspond to the selected unit.

Since this modification has an arrangement in which the light source unit 111 is able to concentrically operate another endoscope apparatus, a complicated labor of operating a corresponding adjustment switch when each unit is operated can be saved.

The structure of the apparatus is not limited to this. For example, the operation panel and the host controller may be disposed in the video processor.

A fifth embodiment of the present invention will now be described with reference to FIGS. 10 to 16.

The fifth embodiment has an arrangement that a control portion in a light source unit of an endoscope apparatus for controlling each function is constituted by using a programmable integrated circuit. The light source unit has a plurality of functions: a function for adjusting the quantity of irradiation light; a function for adjusting the sensitivity at the photography; and a function for adjusting the quantity of air to be supplied.

Figure 10:
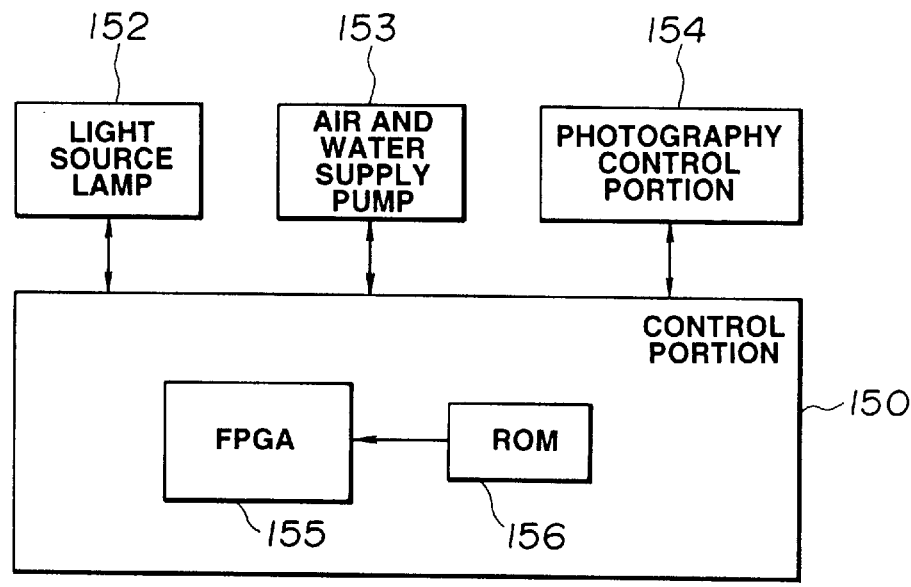

The light source unit, as shown in FIG. 10, comprises a control portion 150 having a digital circuit which is capable of changing the circuit function. A light source lamp 152 for emitting the irradiation light; an air and water supply pump 153 for supplying air or the like through the endoscope; and a photographing control portion 154 for adjusting sensitivity of a photographing unit are connected to the control portion 150 so that each portion is controlled. The control portion 150 has a programmable integrated circuit preferably comprising an FPGA 155 so as to serve as a digital circuit constituting means for constituting a circuit, for example, a logical circuit, in accordance with circuit data for defining the circuit function in a digital circuit. The control portion 150 has a storage device preferably comprising a ROM 156 serving as a circuit data storage means for storing the circuit data. Thus, the circuit can be constituted and changed in accordance with the circuit data.

Figure 11:
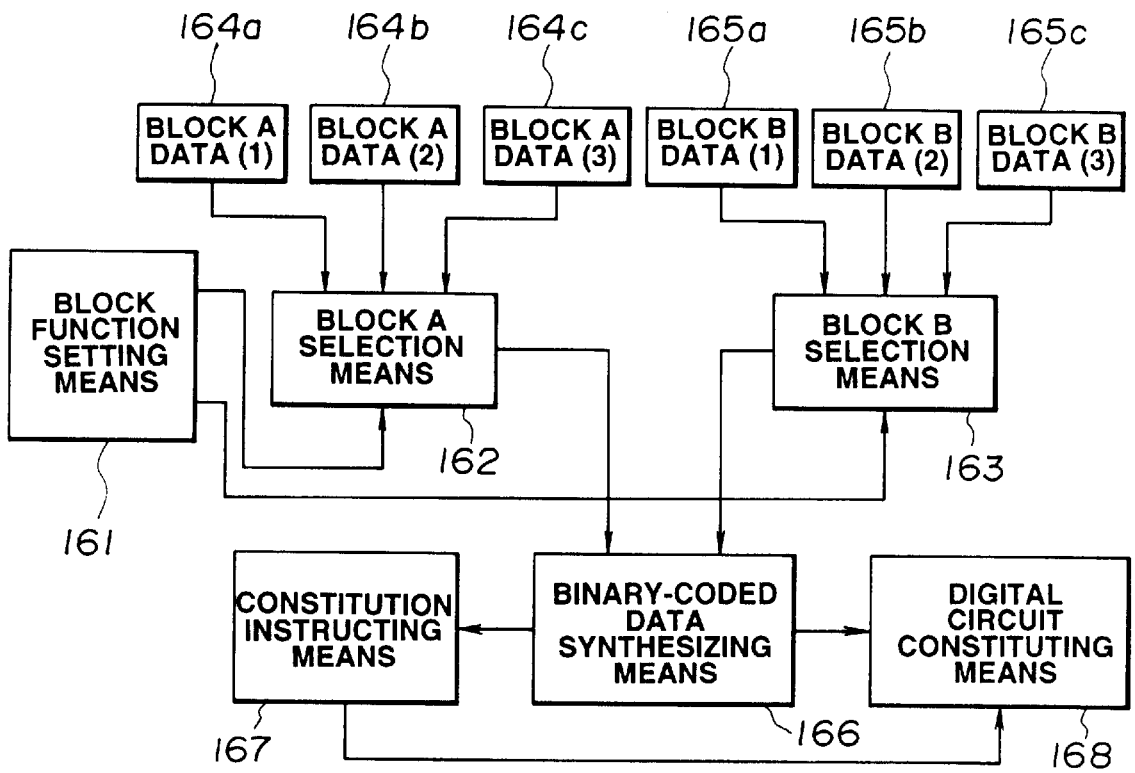

The functional structure of the control portion of the light source unit is shown in FIG. 11. FIG. 11 illustrates the functional structure of a portion for setting the operation of two functions. Referring to FIG. 11, the operation of the control portion for constituting a circuit will now be described.

A block function setting means 161 for instructing setting of each function block which corresponds to each function is provided. A block A selection means 162 and a block B selection means 163 for selecting the setting of operation for each function block select circuit data for setting the operation. Among the plural function blocks, an assumption is made here that the block A is a light quantity adjustment function and the block B is a photography sensitivity adjustment function. The instruction of setting the operation for each function block is, in accordance with, for example, an operation instruction made by a user, supplied to the block A selection means 162 and the block B selection means 163 by the block function setting means 161.

The block A selection means 162 selects circuit data corresponding to the foregoing instruction of setting from among a plurality of block A data (1) 164a, (2) 164b and (3) 164c to supply the selected circuit data to a binary-coded data synthesizing means 166. The block B selection means 163 selects circuit data corresponding to the foregoing instruction of setting from among a plurality of block B data (1) 165a, (2) 165b and (3) 165c to supply the selected circuit data to a binary-coded data synthesizing means 166. The block data denoting circuit information having a specific function corresponding to each of the foregoing sections is, as binary-coded data, stored in a storage device, such as a ROM in such a manner that a data table is formed in the storage device. The block data can be read from an external unit by communication in place of the storage device.

The binary-coded data synthesizing means 166 synthesizes a plurality of circuit data items supplied from the block A selection means 162 and the block B selection means 163 into one data item in order to constitute the most effective circuit satisfying the desired function in accordance with circuit data about the plural functions. After the synthesis of the circuit data has been completed in the binary-coded data synthesizing means 166, a signal representing the completion of the synthesis is supplied to a constitution instruction means 167 for instructing the circuit structure. When the constitution instruction means 167 detects the completion of the synthesis, it supplies a circuit constitution instruction to a digital circuit constituting means 168. Thus, the digital circuit constituting means 168. Thus, the digital circuit constituting means 168 constitutes a circuit corresponding to the synthesized circuit data. As a result, the circuit function in the control portion is set. The digital circuit constituting means 168 is constituted by a programmable integrated circuit so that a digital circuit having a predetermined function in accordance with the circuit data is constituted.

By constituting the control portion as described above, the operation characteristics of the circuit can be set to be freely adaptable to the state of use by a user or to satisfy the desire of the user. Furthermore, only a circuit having a required function can be constituted in accordance with the state of use. Thus, the apparatus structure can be simplified. In a case where specific data among circuit data to be selected in accordance with the value set by a user is used frequently, it may automatically be selected at the time of the supply of electric power to the apparatus without the necessity of performing selection by the user.

An example will now be described in which the control portion constituted by using the programmable integrated circuit as described above is employed in a light quantity adjustment means, a photography sensitivity adjustment means and an air supply quantity adjustment means.

Figure 12:
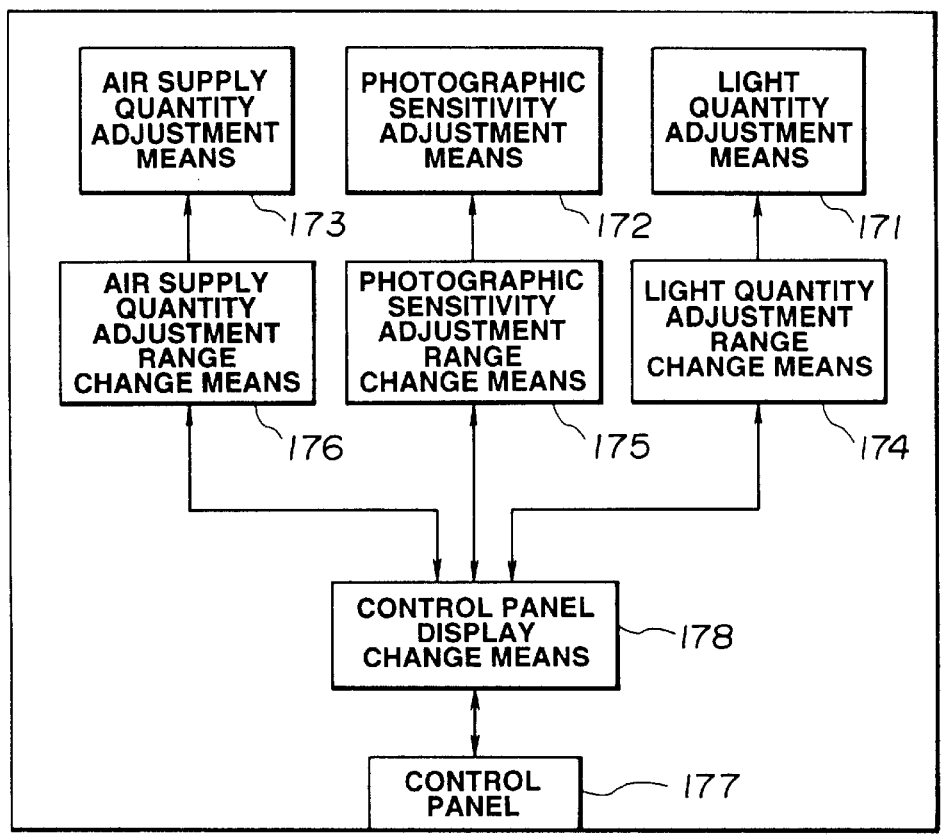

FIG. 12 illustrates the functional structure of the means for adjusting each function in the light source unit. A light quantity adjustment means 171, a photography sensitivity adjustment means 172 and an air supply quantity adjustment means 173 respectively have a light quantity adjustable range changing means 174, a photography sensitivity adjustable range changing means 175 and an air supply quantity adjustable range changing means 176 connected thereto for the purpose of changing the respective adjustable range. The foregoing adjustable range changing means are connected to an operation panel display changing means 175 for changing the display on an operation panel 177. Each of the adjustable range changing means, the control portion for each adjustment means and the operation panel display changing means are constituted by digital circuits each including the foregoing programmable integrated circuit so that the circuit change is enabled.

The light source unit for an endoscope comprises the front operation panel that has switches for setting adjustment parameter values for the light quantity adjustment, the photography sensitivity adjustment and the air supply quantity adjustment and display portions for indicating the state of settings.

Figure 13:
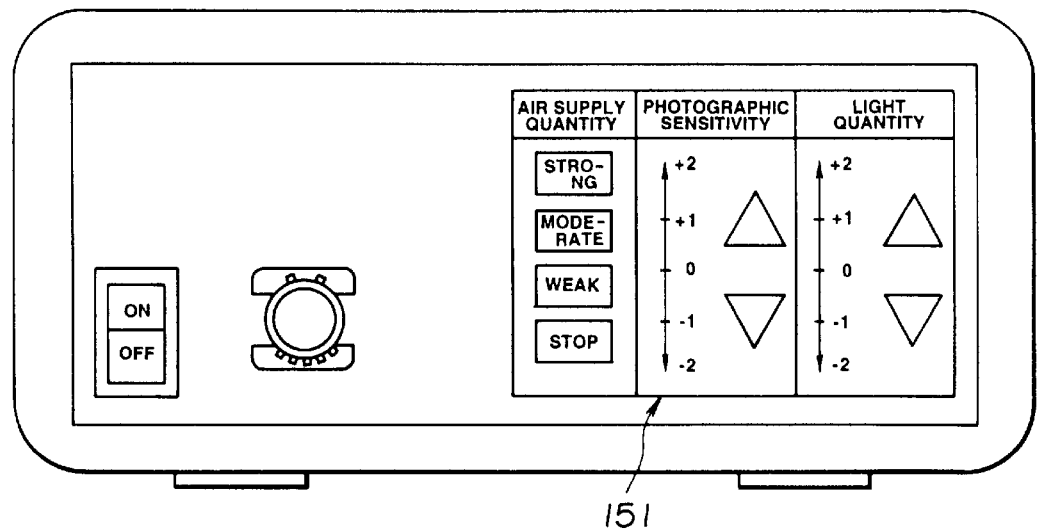

The conventional apparatus has been usually arranged as shown in FIG. 13 in such a manner that a parameter setting means 151 of the operation panel has been fixed and it cannot be changed to be adaptable to the state of use. The air supply adjustment can be adjusted to four stages consisting of "stop", "weak", "moderate" and "strong". The photography sensitivity adjustment and the light quantity adjustment are each adjustable within a range from −2 to +2 either stepwise or in a stepless manner. Thus, the adjustment is limited to predetermined values or within a predetermined range.

Assuming that the photography sensitivity adjustment for a certain subject of inspection is finally adjusted to a value in the vicinity of +1 and the same for another subject of inspection is finally adjusted to a value in the vicinity of −1, the adjustment of the former case is independent in the range from about −2 to 0. On the other hand, the adjustment of the latter case is independent in the range from about 0 to +2. In this case, about half of the adjustment parameter range becomes independent from the final adjustment. Therefore, a problem arises in that set values in a region that is not required for the adjustment are provided and the adjustable range is too wide and therefore fine adjustment near a desired value cannot be performed. As for the light quantity adjustment, some subjects do not require the overall adjustable range at the time of the light quantity adjustment because only a value near the fully-opened diaphragm position or only a value near the fully-closed diaphragm position is used.

In order to enable the adjustable range or the adjustment step to be changed to be adaptable to the state of use, it might be considered feasible to employ a structure in which circuits corresponding to the respective operation settings are prepared to have several adjustable ranges. However, the size of the apparatus is enlarged excessively and therefore the cost cannot be reduced to practically employ the foregoing structure.

Accordingly, this embodiment has an arrangement where the control portion is constituted by a digital circuit using the programmable integrated circuit, the internal structure of which is constituted in accordance with circuit data, and the adjustable range changing means is used to freely set the adjustable range and the adjustment steps in accordance with the state of use.

Figure 14:
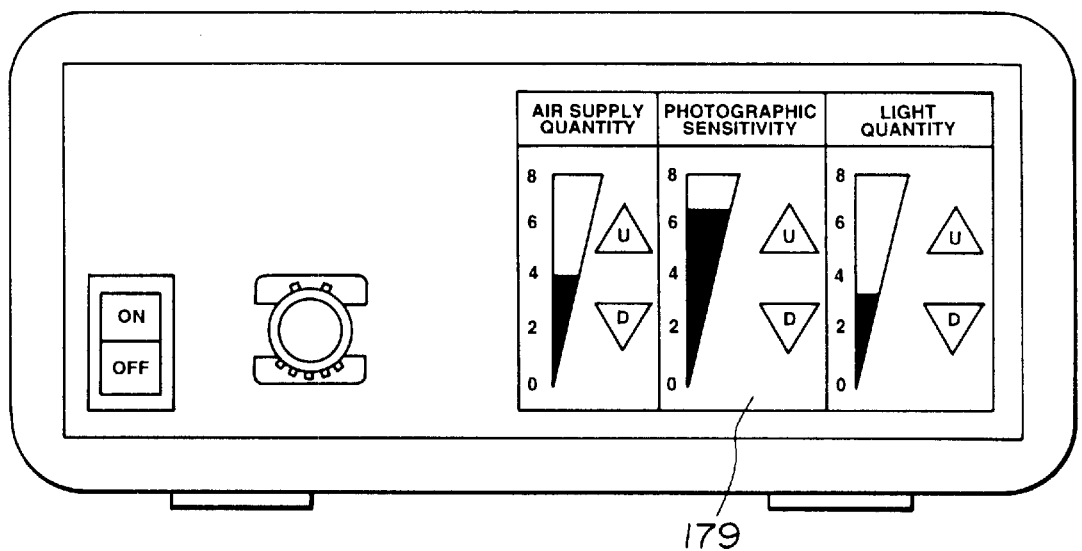

The structure of an operation panel according to this embodiment is shown in FIG. 14. A parameter setting portion 179 of the operation panel is formed by a touch panel. A display means preferably comprising a liquid crystal panel is disposed below the touch panel. The touch panel consists of transparent electrodes and a multiplicity of switches disposed in a matrix configuration. When a scanning means scans in the X direction (in the horizontal direction) and in the Y direction (in the vertical direction), the coordinates of the depressed switch can be detected. For example, if a portion expressed as "quantity of air supply" is touched, the coordinates of the touched portion are received by the control means and therefore an operation instruction corresponding to the coordinates, that is, the instruction of changing the adjustable range of the air supply quantity, can be detected.

In a case where the adjustable range of the air supply quantity is changed, the portion "air supply quantity" in the parameter setting portion 179 is initially depressed so that commencement of the change of the adjustable range is instructed. When the "air supply quantity" is depressed, the instruction to change the adjustable range is issued to the air supply quantity adjustable range changing means 176 through an operation panel display changing means 178. In response to this, the air supply quantity adjustable range changing means 176 changes the adjustable range of the air supply quantity adjustment means 173. In accordance with this, the operation panel display changing means 178 changes the image indicated on the display portion of the operation panel 177. When the adjustable range is changed, the portion "U" (up) or "D" (down) is depressed to vertically move the central value of the adjustment or the upper limit value and the lower limit value of the same so as to set the range. When the "air supply quantity" portion is again depressed after the adjustable range has been changed, a new adjustable range can be set. Note that the adjustment steps may be changed whenever the "air supply quantity" is depressed.

Figure 15:
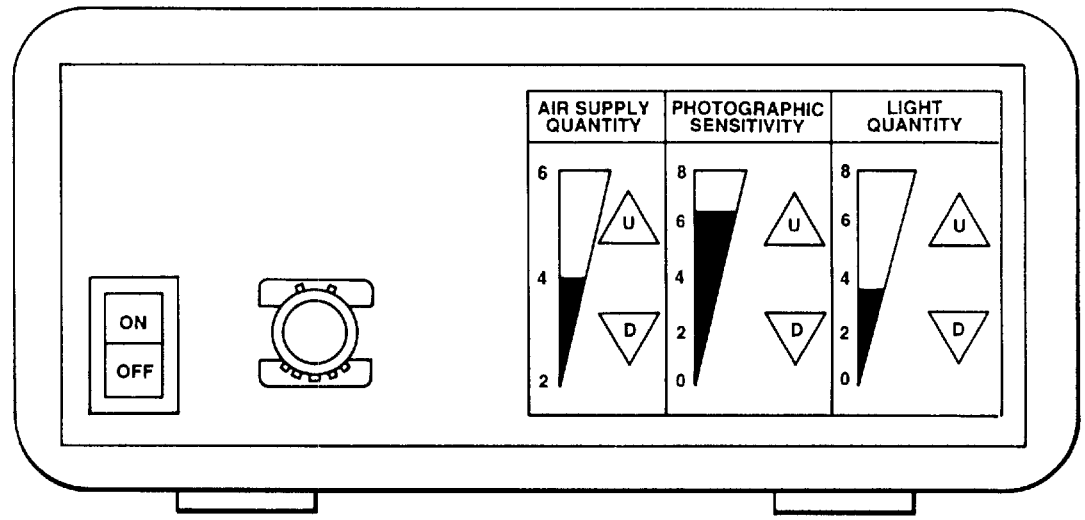
Figure 16:
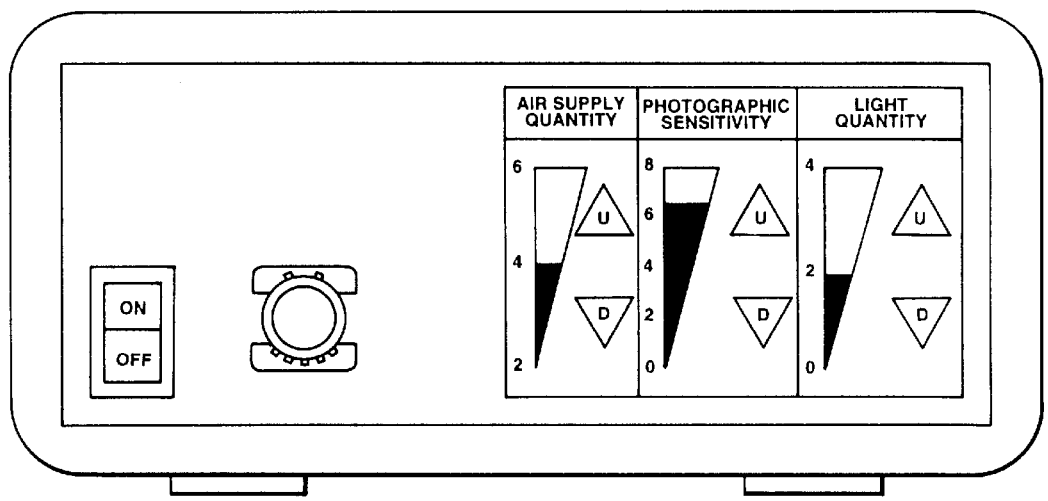

An assumption is made here that the initial setting of the range in which the air supply quantity can be changed is made to be from 0 to 8 as shown in FIG. 14. By issuing an instruction to change the adjustable range as described above, the central value of the adjustment is changed to 4 and the adjustable range is changed from 2 to 6 as shown in FIG. 15. As a result, a finer adjustment than the initial state can be performed in a desired adjustable range.

Also the light quantity adjustment and the photography sensitivity adjustment can be performed similarly such that the range in which the light quantity is adjusted is changed, for example, from 0 to 8 to 0 to 4 so that a finer light adjustment of the value on the dark side is performed.

The operation setting of another function of the light source unit or another apparatus may be similarly changed to be adaptable to the state of use as well as the foregoing function.

As described above, according to this embodiment, the function, the state of operation and the operation characteristics of the apparatus can freely be set to be adaptable to the state of use. Therefore, an effect can be obtained in that the apparatus can be always used in an optimum state.

Figure 17:
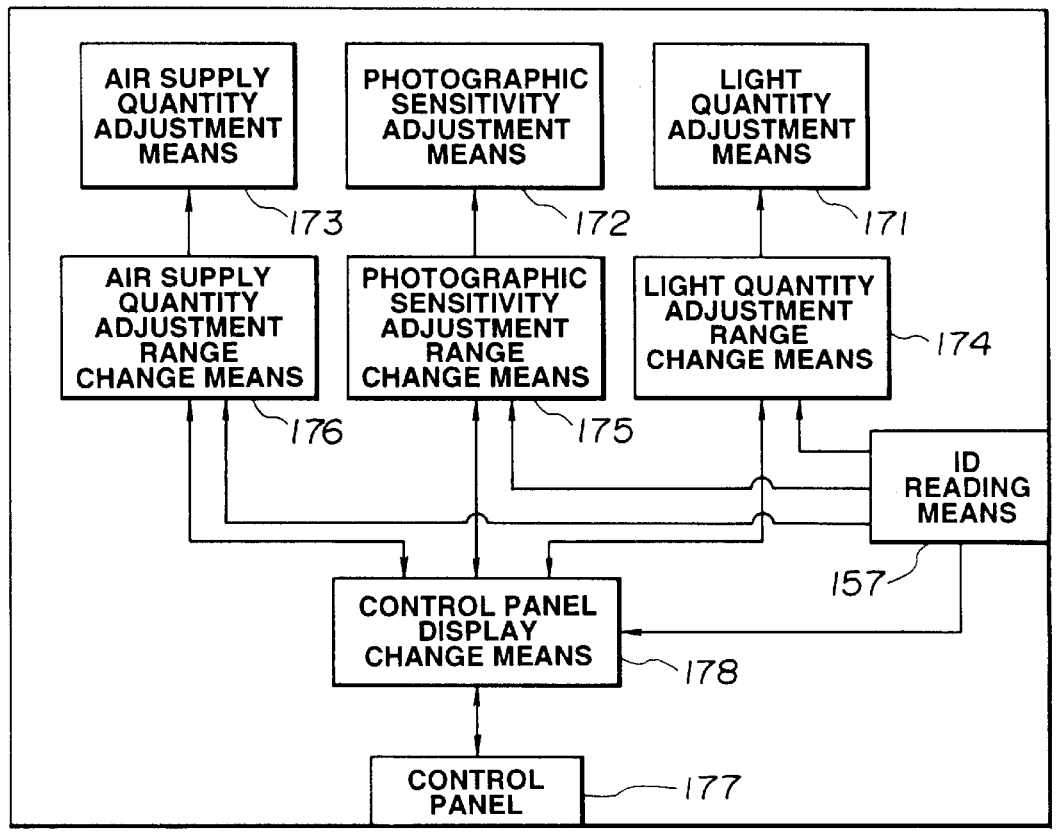
FIG. 17 is a block diagram which illustrates a modification of a function adjustment means having an adjustable range changing means.
Figure 18:
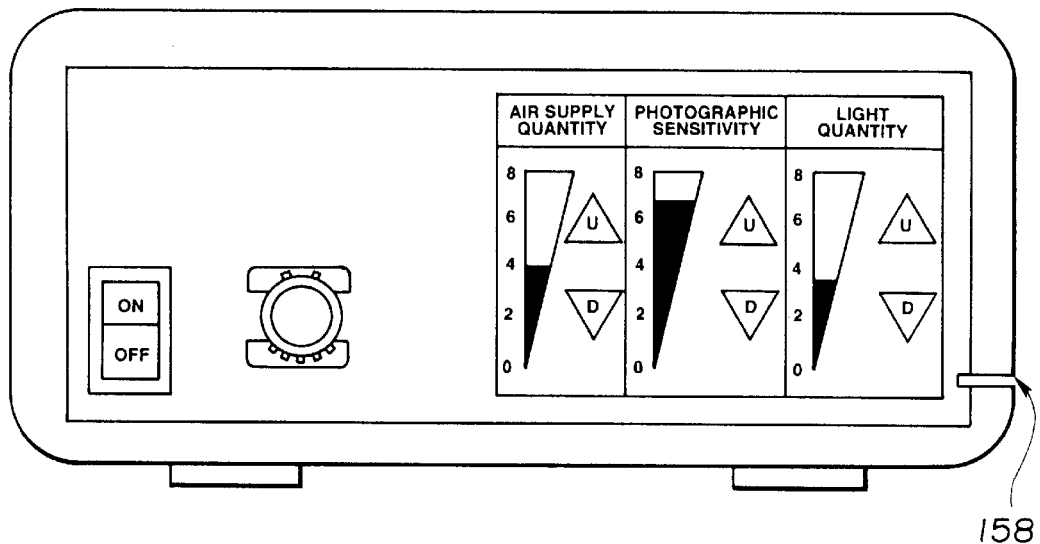
FIG. 18 is an explanatory view which illustrates the structure of an operation panel of the light source unit according to the modification shown in FIG. 17.

A modification of a function adjustment means having the adjustable range changing means shown in FIG. 12 is shown in FIG. 17. This modification comprises an ID reading means 157 to recognize a subject of inspection or a user. An ID card insertion portion 158 is disposed adjacent to the operation panel as shown in FIG. 18 to receive the inserted ID card for each subject of inspection or each user so that the subject of inspection or the user is identified by the ID reading means 157.

In this case, the most flexible adjustable range for each subject of inspection is previously registered in the storage means or a desired adjustable range for each user is registered to change the adjustable range by each adjustable range changing means in accordance with the identification detected by the ID reading means 157. As a result of the structure thus made, simple reading of the ID of the subject of inspection or the user enables setting to be changed such that the optimum adjustable range is automatically realized for each subject of inspection or the user.

As described above, each adjustment means is so constituted that the adjustable range can be changed. As a result, a desired adjustable range or desired adjustment steps can be set to be adaptable to the state of use, such as the type of the subject of inspection and the desire of the user. Thus, the apparatus can always be used in an optimum operation set state.

An example of the structure of the light quantity adjustment means of the light source unit will now be described. The light quantity adjustment means of the light source unit for automatically adjusting light has been formed in such a manner that the response of the automatic light adjustment circuit is fixed. For example, the loop gain and the frequency response characteristics of the automatic light adjustment circuit have been set to values with which the diaphragm does not disperse (encounters hunting) by determining the integration time constant to be adaptable to the characteristics of the apparatus or the subject. Therefore, some subjects, for example, the large intestine, cause the light adjustment circuit to operate frequently because plica is continued and therefore causes a problem in that observation cannot easily be performed.

Figure 19:
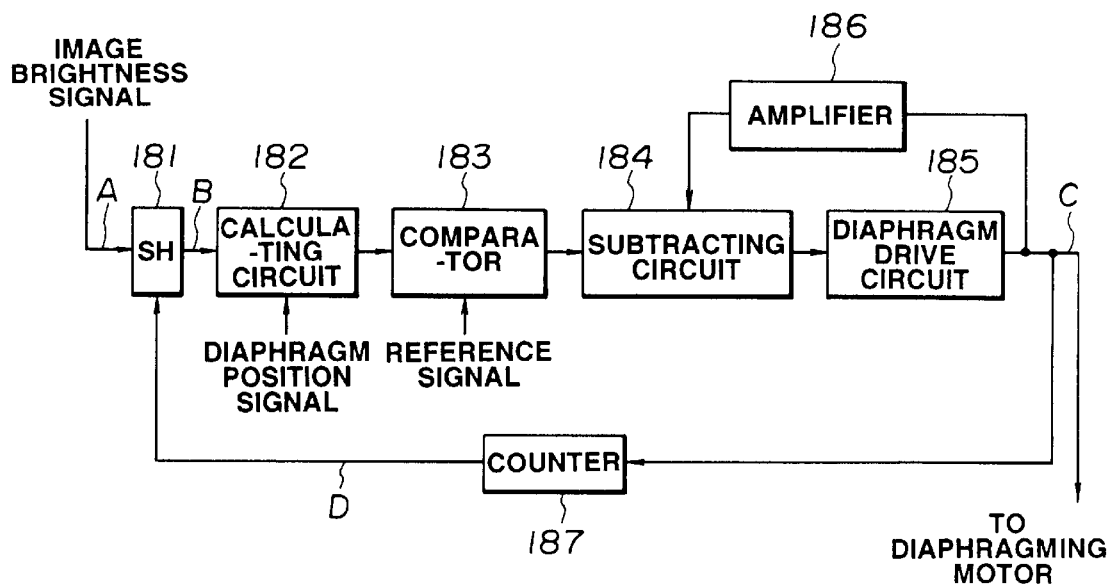
FIG. 19 is a block diagram which illustrates a first structural example in which the response frequency of an automatic light adjustment circuit of a light quantity adjustment means of the light source unit can be changed.
Figure 20:
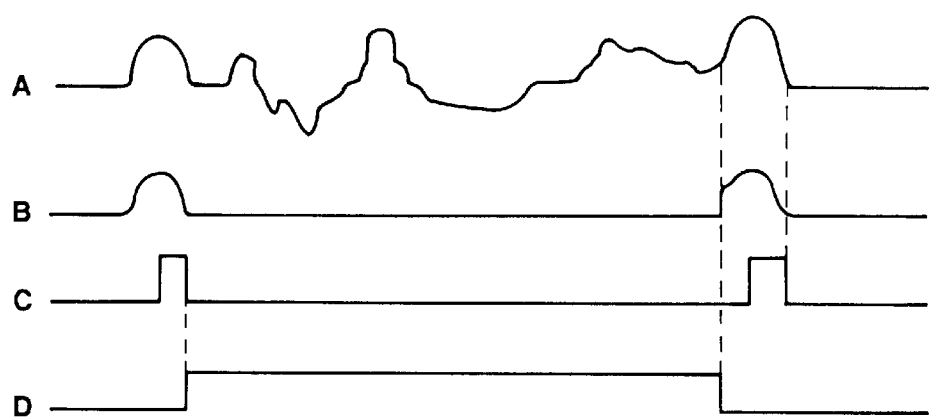
FIG. 20 is an operation waveform graph showing a signal for each portion of the automatic light adjustment circuit shown in FIG. 19.

Accordingly, this example is structured such that the response frequency can be changed to perform an adequate light adjustment operation without changing the response speed of the automatic light adjustment circuit. FIG. 19 illustrates a first structural example with which the response frequency of the automatic light adjustment circuit can be changed. FIG. 20 is a graph showing the operational waveform of signals for portions of the structure shown in FIG. 19.

The automatic light adjustment circuit has an arrangement that it generates a diaphragm drive signal in response to an image brightness signal which is in proportion to the brightness of the observed image obtained by integrating video signals or the like by a video signal processing means, such as a video processor, to instruct the light adjustment. In this example, the input stage has a sample holding circuit (SH) 181 for holding the image brightness signal for a predetermined amount of time.

Image brightness signal (A) is supplied to a calculating circuit 182 through the sample holding circuit 181. After correction has been performed in the calculating circuit in response to the diaphragm position signal, the image brightness signal (A) is supplied to a comparator 183 so as to be subjected to a comparison with a reference signal. A difference signal which is the output from the comparator 183 is allowed to pass through a subtraction circuit 184 and a diaphragm drive circuit 185 so as to be transmitted to a diaphragming motor as a diaphragm drive signal (C). In the subtraction circuit 184, a signal value obtained by amplifying the diaphragm drive signal, which is the output from the diaphragm drive circuit 185, by an amplifier 186, that is, a value which is proportional to the diaphragm drive signal, is subtracted from the difference signal, which is the output from the comparator 183. As a result of the foregoing being fed back, the level adjustment is performed so that a diaphragm drive signal is generated.

A counter 187 for transmitting a control signal to the sample holding circuit 181 is connected to the output terminal of the diaphragm drive circuit 185, the diaphragm drive signal also being supplied to the counter 187. The counter 187 starts counting when the diaphragm drive circuit 185 transmits the diaphragm drive signal. At this timing, holding signal (D) for holding the image brightness signal for a predetermined time is transmitted to the sample holding circuit 181. As a result, the sample holding circuit 181 holds the image brightness signal, thus holding output (B) from the sample holding circuit 181 to be unchanged for a predetermined amount of time as shown in FIG. 20.

As described above, the provision, in the automatic light adjustment circuit, the means for limiting the processing of the input signal by holding the image brightness signal for a predetermined time from the output of the diaphragm drive signal enables the response of the automatic light adjustment circuit to be restricted. Therefore, the response frequency can be changed without lowering of the response speed, and accordingly an adequate light adjustment operation can always be performed regardless of the subject. As a result, even if a subject, such as the large intestine, of a type plica is continued, is observed, the frequency operation of the automatic light adjustment circuit can be prevented. Thus, a satisfactory observation can be made.

Figure 21:
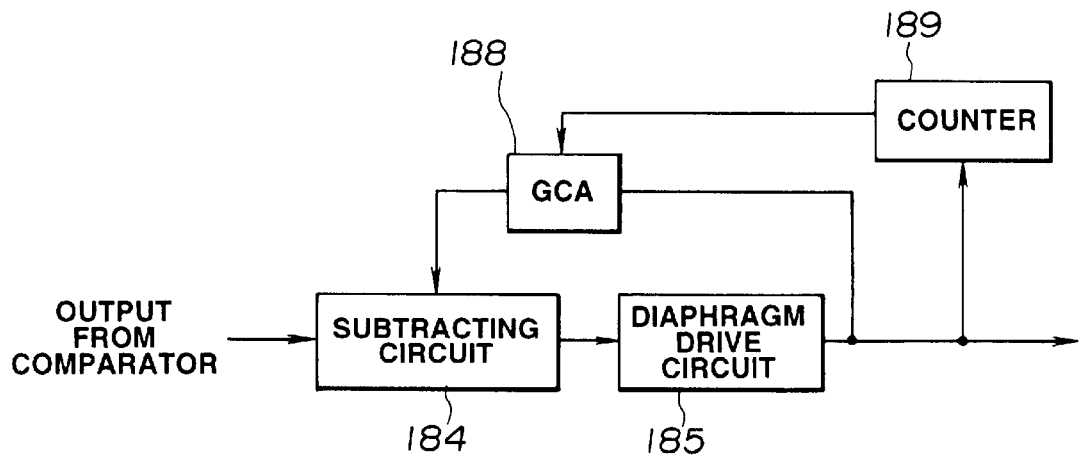
FIG. 21 is a block diagram which illustrates a second structural example in which the response frequency of the automatic light adjustment circuit can be changed.

FIG. 21 illustrates a second structural example having an arrangement where the response frequency of the automatic light adjustment circuit can be changed. The second structural example has an arrangement in which a means for controlling the gain of a feedback loop for adjusting the level of the diaphragm drive signal is provided in place of the sample holding circuit according to the first structural example.

A gain control amplifier (GCA) 188 is disposed in a feedback loop of the subtraction circuit 184 and the diaphragm drive circuit 185 so that the gain is changed in response to the gain switch signal supplied from a counter 189. The counter 189 starts counting when the diaphragm drive signal is transmitted from the diaphragm drive circuit 185. At this timing, a gain switch signal for raising the gain of the GCA 188 for a predetermined amount of time is transmitted to the GCA 188. As a result, the gain of the feedback loop for generating the diaphragm drive signal is raised, causing the output from the subtraction circuit 184 to be reduced. Thus, the gain of the diaphragm drive signal, which is the output with respect to the image brightness signal which is the input for the automatic light adjustment circuit, is lowered. Therefore, the diaphragm drive signal is not transmitted for a predetermined amount of time, and accordingly, the response frequency of the automatic light adjustment circuit is lowered.

The second structural example is also able to restrict the response of the automatic light adjustment circuit similarly to the first structural example, thus enabling the response frequency to be changed without lowering of the response speed.

Figure 22:
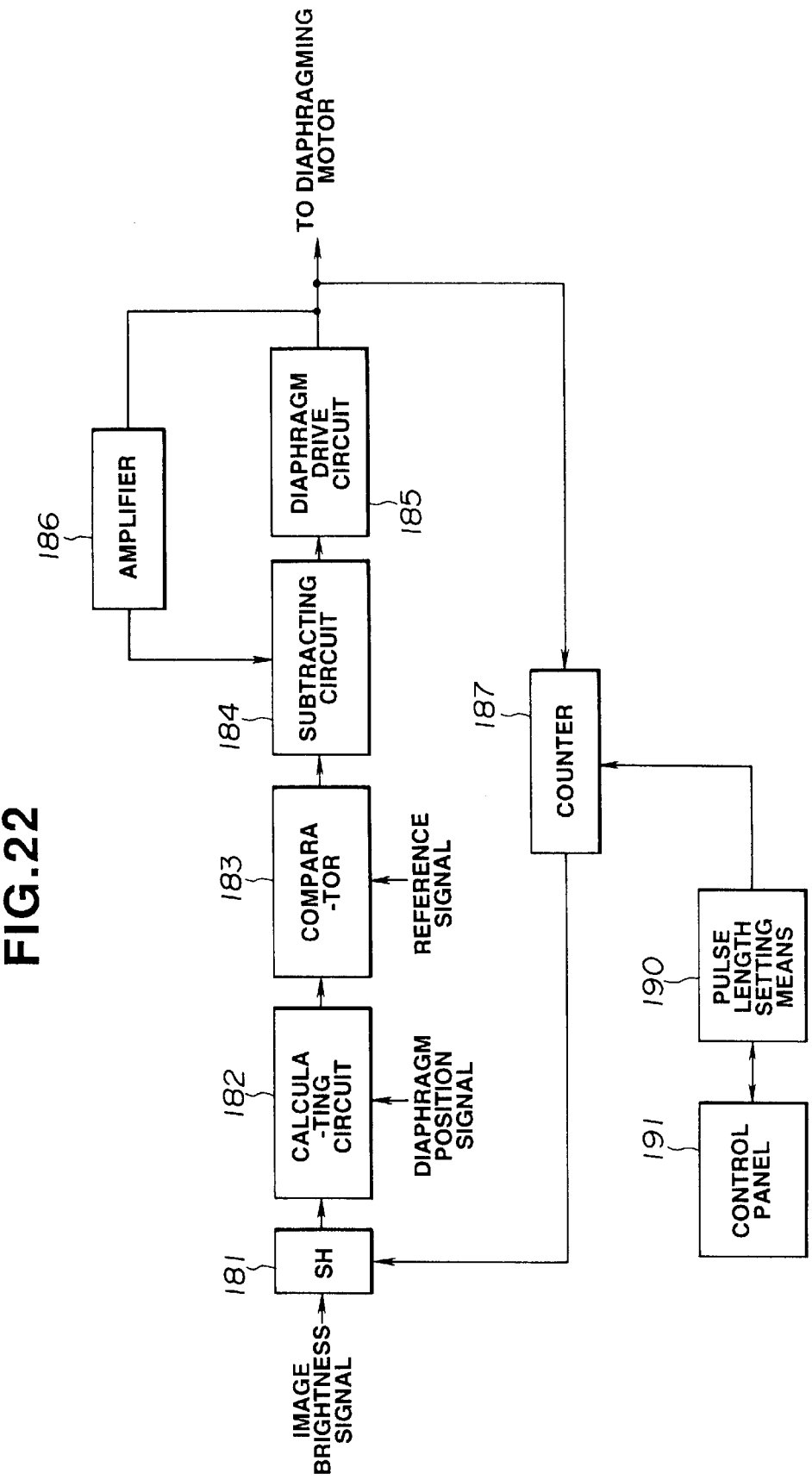
FIG. 22 is a block diagram which illustrates a third structural example in which the response frequency of the automatic light adjustment circuit can be changed.

FIG. 22 illustrates a third structural example has, in addition to the arrangement of the first structural example, a pulse length setting means 190 for changing the time in which the counter 187 performs counting, and an operation panel 191 for instructing the operation of the pulse length setting means 190.

This example enables the period in which the response of the automatic light adjustment circuit is restricted, to be set to a desired length by use of the operation panel 191 by a user. When a setting value about the period, in which the response of the automatic light adjustment circuit is restricted, is supplied through the operation panel 191, the pulse length setting means 190 transmits, to the counter 187, a signal representing the pulse length corresponding to the supplied set value. As a result, the pulse width of the holding signal to be transmitted from the counter 187 is changed in accordance with the set value so that the period in which the image brightness signal is held in the sample holding circuit 181 is set.

The provision of the input means for setting the period in which the response of the automatic light adjustment circuit is restricted enables the response frequency of the automatic light adjustment circuit to be set to an arbitrary value for a user.

Note that each circuit in the foregoing light quantity adjustment means may, of course, be constituted by the FPGA.

A sixth embodiment of the present invention will now be described with reference to FIGS. 23 to 26. The sixth embodiment is an example having an arrangement such that the automatic light adjustment means of the endoscope apparatus is constituted by using a programmable integrated circuit.

Figure 23:
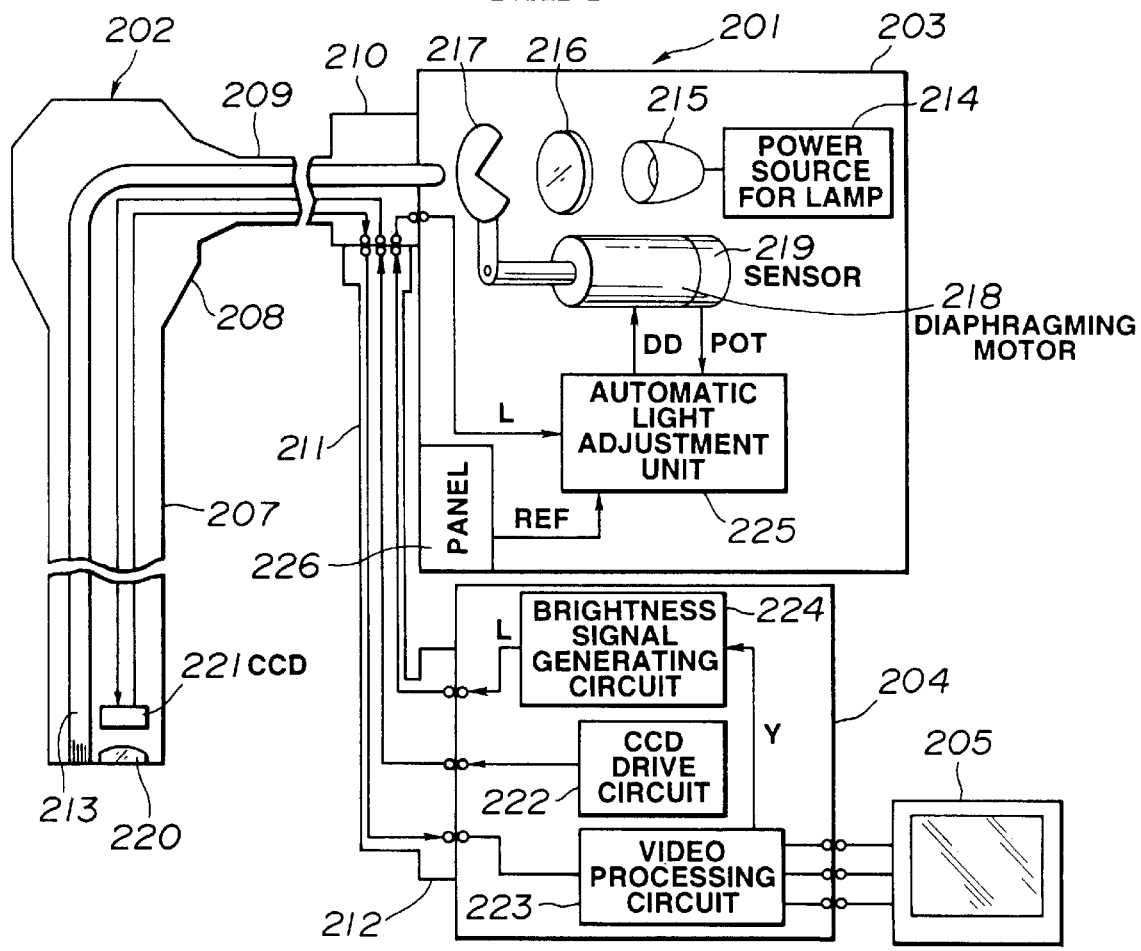

An endoscope apparatus 201 according to the sixth embodiment, as shown in FIG. 23, comprises: an electronic endoscope 202 including an image pickup device; a light source unit 203 for supplying irradiation light to the electronic endoscope 202; a video processor 204 for processing a signal of the image pickup device included in the electronic endoscope 202; and a monitor 205 for displaying a video signal transmitted from the video processor 204.

Although FIG. 23 illustrates the endoscope apparatus 201 in the foregoing one combination, an electronic endoscope and a video processor each having different characteristics can be connected to the light source unit 203.

The electronic endoscope 202 comprises: an elongated insertion portion 207; an operation portion 208 disposed at the rear end of the insertion portion 207; and a universal cable 209 extending from the operation portion 208. A connector 210 disposed at an end of the universal cable 209 can be detachably received by a connector receiver of the light source unit 203.

An end of a signal cable 211 is connected to the side portion of the connector 210 through the connector. A signal connector 212 disposed at another end of the signal cable 211 can detachably be attached to the video processor 204.

A light guide 213 is inserted into the insertion portion 207 and the universal cable 209, the end of the light guide 213 adjacent to the operator reaching the connector 210. Therefore, by attaching the connector 210 to the light source unit 203, irradiation light is supplied from the light source unit 203 to the end of the light guide 213 adjacent to the operator.

That is, irradiation light from a lamp 215, which is caused to emit light by a lamp power source 214, is condensed by a condenser lens 216, and then it is allowed to pass through a diaphragm 217 which controls the quantity of light which passes through the same. Then, light is supplied to the end of the light guide 213 adjacent to the operator. The diaphragm 217 is attached to the rotational shaft of a diaphragming motor 218 to be rotated in accordance with the rotational angle of the diaphragming motor 218 so that the quantity of light which passes through the same is restricted.

A sensor (or an encoder) 219 for detecting the rotational position of a potentiometer is attached to the diaphragming motor 218. The sensor 219 transmits the position of the diaphragm 217 or a position signal POT corresponding to the quantity of light passed by the diaphragm.

Irradiation light supplied to the end of the light guide 213 adjacent to the operator is transferred to the leading end of same so as to be emitted forwards over the leading end surface of the light guide 213 secured to an irradiating window at the leading portion of the insertion portion 207 so that the subject, such as an affected part, is irradiated with light. The subject, irradiated with light, forms an optical image on a focal plane of an objective lens 220 attached to the observation window formed at the leading portion of the insertion portion 207.

An image pickup device, for example, a CCD 221 is disposed at the focal plane of the objective lens 220, the CCD 221 photoelectrically converting the image of the subject. The CCD 221 is supplied from a CCD drive signal from a CCD drive circuit 222 disposed in the video processor 204. The supply of the signal causes a photoelectrically converted image signal to be transmitted.

The image signal, which is output from the CCD 221, is received by a video processing circuit 223 so that a standard video signal, for example, an RGB signal is generated. The RGB signal is supplied to the monitor 205 so that the color image of the subject is displayed.

The video processing circuit 223 also generates brightness signal Y. The brightness signal Y is supplied to a brightness signal generating circuit 224. In the brightness signal generating circuit 224, brightness signal L for use in controlling the quantity of light is generated. The brightness signal generating circuit 224 comprises: an integrating circuit for integrating, for example, signal periods for one frame, and brightness signals Y; and a sample holding circuit for sample-holding the integrated brightness signals Y. The integrated signal (the integrated brightness signal) held in the sample holding circuit is transmitted as the brightness signal L.

The brightness signal L is supplied to an automatic light adjustment unit 225 disposed in the light source unit 203 through a signal line in the signal cable 211. The automatic light adjustment unit 225 is supplied with the position signal POT from the sensor 219 and also supplied with reference signal REF serving as a reference of brightness from a reference setting switch of the panel 226.

The automatic light adjustment unit 225 transmits diaphragming motor drive signal DD for controlling the drive of the diaphragming motor 218 in such a manner that the brightness signal L coincides with the reference signal REF if the supplied brightness signal L is deviated from the position signal POT supplied from the sensor 219 and the reference signal REF. In this case, reference with the position signal POT supplied from the sensor 219 is made to determine the drive signal DD.

Figure 24:
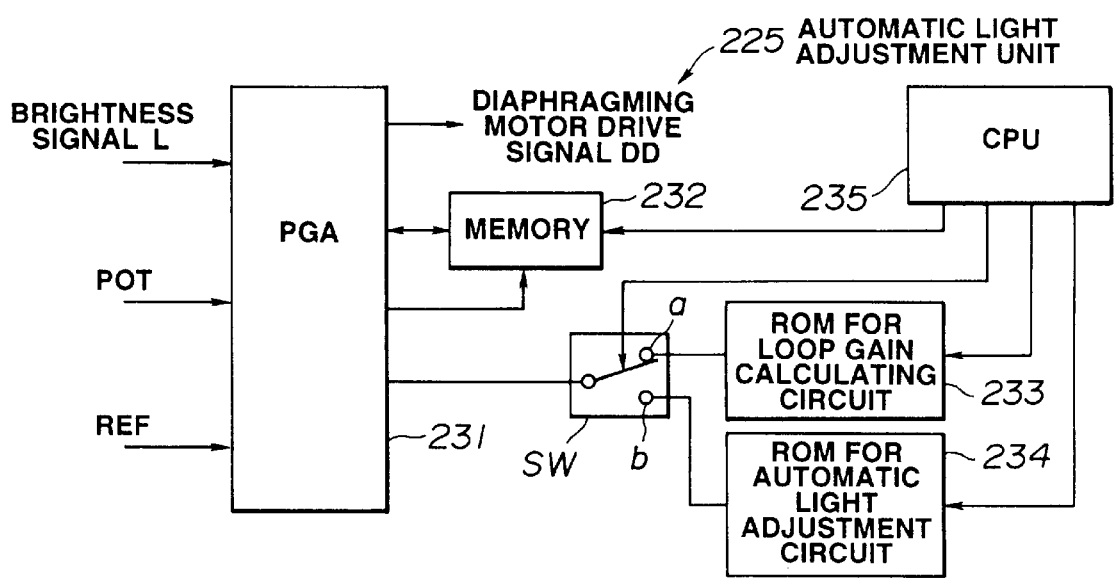

FIG. 24 illustrates the structure of the automatic light adjustment unit 225. The automatic light adjustment unit 225 comprises: a programmable gate array (hereinafter abbreviated to a "PGA") 231 having calculation and automatic light adjustment functions for generating a diaphragming motor drive signal DD and performing a calculation in response to the brightness signal L to generate adequate loop gain data for the light adjustment unit; a memory 232 serving as a correction value storage means for storing loop gain correction data in response to the position signal POT; a ROM 233 for a loop gain calculating circuit, the ROM 233 serving as a calculation circuit data storage means for storing circuit data for constituting the loop gain calculating circuit; a ROM 234 for an automatic light adjustment circuit, the ROM 234 serving as an automatic light adjustment circuit data storage means for storing circuit data for constituting the automatic light adjustment circuit; a switch SW for switching the circuit data; and a CPU 235 for controlling the ROMs 233 and 234 and the switch SW.

In the PGA 231, a logical circuit is formed in accordance with a program of the circuit data recorded in the ROMs 233 and 234. The circuit structure in the PGA 231 can be changed by rewriting the program.

In the sixth embodiment, the control performed by the CPU 235 initially causes the circuit constituting data in the ROM 233 for the loop gain calculating circuit to be read to form a function as the loop gain calculating circuit in the PGA 231, and the loop gain correction data for setting an adequate loop gain is generated and stored in the memory 232. Then, the circuit constituting data in the ROM 234 for the automatic light adjustment circuit is read to form a function as an automatic light adjustment circuit in the PGA 231 so that the automatic light adjustment is performed. This embodiment is characterized in that the loop gain correction data stored in the memory 232 is used at the foregoing moment to perform control in such a manner that a predetermined loop gain is realized. The foregoing arrangement will now be specifically described.

When power is supplied to the light source unit 203 and the video processor 204, the CPU 235 controls switching of the switch SW to cause contact a to be turned on so that a state is realized in which the ROM 233 for the loop gain calculating circuit is connected to the PGA 231. The CPU 235 supplies a data reading address signal to the ROM 233 for the loop gain calculating circuit so as to cause the circuit data to be transmitted from the ROM 233 for the loop gain calculating circuit to the PGA 231.

Figure 25:
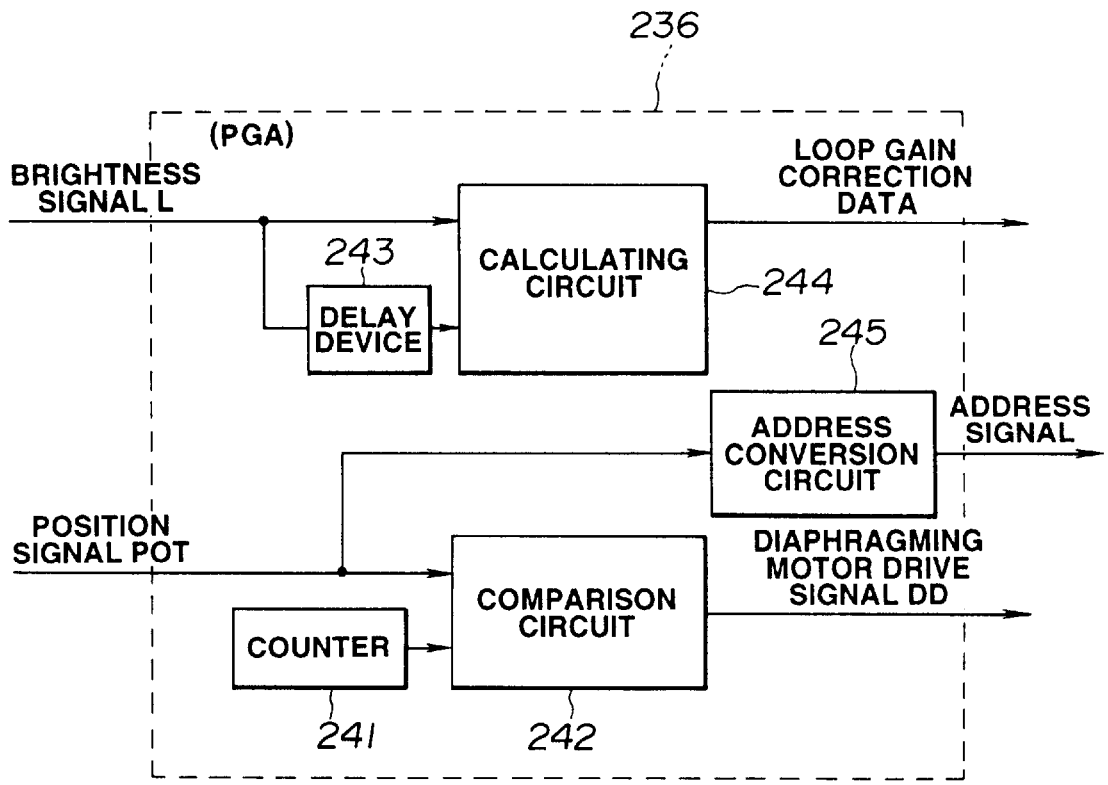

The PGA 231 forms a loop gain calculating circuit in accordance with the circuit data supplied from the ROM 233 for the loop gain calculating circuit. FIG. 25 illustrates the structure of a loop gain calculating circuit 236 formed by the PGA 231.

In the loop gain calculating circuit 236, a counter 241 and a comparison circuit 242 form a circuit for generating the diaphragming motor drive signal DD. The initial value of the counter 241 is made to be zero. The initial value zero of the counter 241 and the position signal POT are subjected to a comparison in the comparison circuit 242. The comparison circuit 242 transmits the diaphragming motor drive signal DD so as to make the position signal POT coincide with zero. Therefore, the diaphragm 217 is set to the initial value corresponding to the full-open state.

Then, a clock is supplied to the counter 241 so that the result of counting is, starting from zero, sequentially increased by one. Therefore, the value of the counter 241 sequentially increased by one and the position signal POT representing zero are subject to a comparison in the comparison circuit 242 so that an error signal is obtained. The error signal is, as the diaphragming motor drive signal DD, transmitted to the diaphragming motor 218. As a result, the diaphragm 217 is diaphragmed by a predetermined quantity of light from the full-open state by a degree of the position signal corresponding to the increase of one in the counter 241.

The brightness signal L in the foregoing diaphragm state is directly supplied to a calculating circuit 244, the brightness signal L being also supplied to the calculating circuit 244 after it has been delayed by one step by a delay device 243. The calculating circuit 244 calculates the difference between the supplied brightness signal L and the brightness signal delayed by one step. Further, the ratio of the difference signal and the brightness signal delayed by one step is calculated. A value obtained by multiplying an inverse number of the obtained ratio with a coefficient is transmitted as a loop gain correction data.

The loop gain correction data is supplied to the memory 232 so as to be stored in a memory cell instructed with an address signal generated by converting the position signal POT in an address conversion circuit 245. Thus, loop gain correction data with respect to the brightness signal L in a state where the counted value of the counter 241 has been sequentially increased by one is calculated to be stored in the memory 232 with the address corresponding to the position signal POT.

By obtaining the loop gain correction data corresponding to each position signal POT, that is, each diaphragm position, the CPU 235 switches the switch SW so that the contact b is turned on when the calculation at the full-diaphragm position has been completed (the completion may be discriminated in accordance with the time because the required time is determined depending upon the number of steps of the diaphragm 217 or in accordance with the full opening judged from the position of the diaphragm 217). The CPU 235 supplies a data reading address signal to the ROM 234 for the automatic light adjustment circuit. The ROM 234 for the automatic light adjustment circuit then transmits circuit data to the PGA 231.

Figure 26:
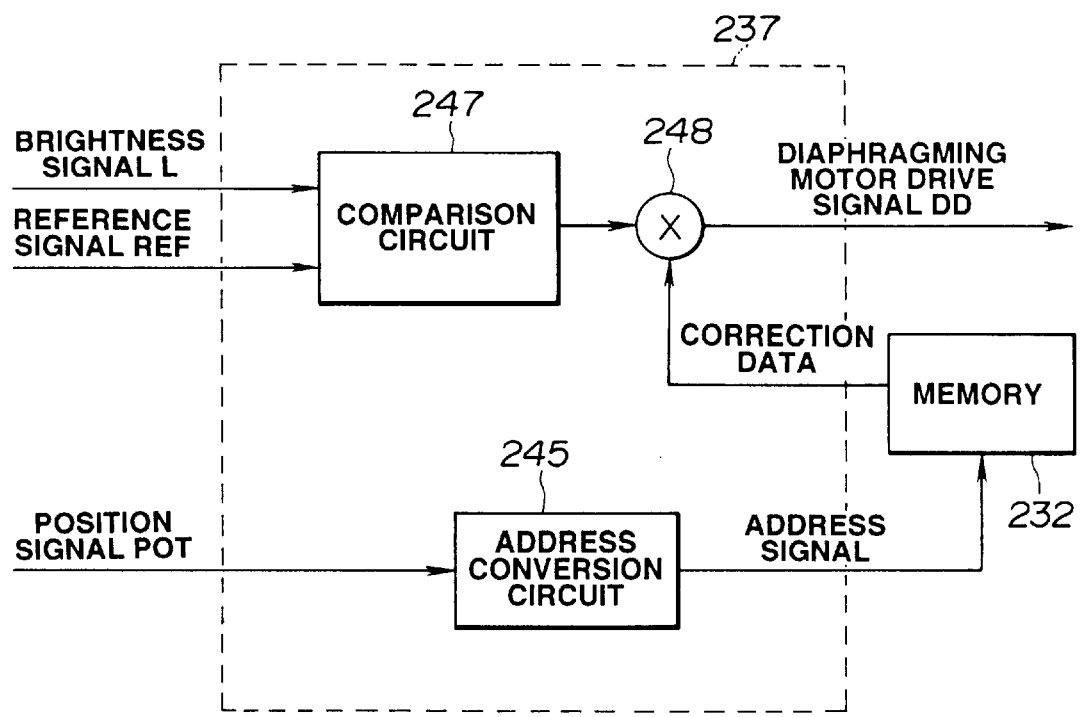

The PGA 231 constitutes the automatic light adjustment circuit in accordance with the circuit data supplied from the ROM 234 for the automatic light adjustment circuit. FIG. 26 illustrates the structure of an automatic light adjustment circuit 237 formed by the PGA 231.

In a case where the correction using the loop gain correction data stored in the memory 232 is not performed, when the brightness signal L is received by the automatic light adjustment circuit 237 similarly to a usual automatic light adjustment circuit, the automatic light adjustment circuit 237 transmits the diaphragming motor drive signal DD to make the difference to be zero after the comparison circuit 247 subjects the brightness signal L and the reference signal REF serving as a reference to a comparison. Therefore, the diaphragming motor drive signal DD having a value which is proportional to the foregoing difference is transmitted in the case where the correction is not performed.

The automatic light adjustment circuit 237 is characterized in that it reads correction data from the memory 232 through the address conversion circuit 245 in response to the address signal corresponding to the diaphragm position POT. Then, the foregoing difference signal is multiplied by the correction data in a multiplier 248 to correct the loop gain so as to transmit the diaphragming motor drive signal DD.

Thus, the loop gain at each diaphragm position POT can be made constant, and accordingly the conventional problem that a filter for lowering the response speed for the purpose of stabilizing the operation must be placed at the largest loop gain and therefore the sacrifice of the response can be overcome. That is, since the loop gain can be made constant regardless of the combination of the units, automatic light adjustment can be performed at an optimum response speed without lowering of the response speed in any combination of several types of endoscopes and video processors.

By using the PGA 231 to constitute the loop gain calculating circuit for obtaining data for correcting the loop gain at the time of the system start, the correction data can be set to realize an optimum loop gain regardless of the combination. Furthermore, constitution of the loop gain calculating circuit and the automatic light adjustment circuit by the same PGA by rewriting the circuit data will reduce the size of the circuit.

Although the foregoing embodiment has the arrangement that the difference between the brightness signal L and the reference signal REF is multiplied by the correction of the loop gain, a damper signal generated due to the displacement of the diaphragm may be multiplied by the same to be added to the drive signal.

The brightness signal L is not limited to the integrated signal of the brightness signal Y of the video signal. It may be the signal EE according to the third embodiment, the signal EE being supplied to the calculating circuit 244 to obtain the difference from delayed signal EE forward by one step so as to obtain the ratio of the delayed signal EE forward by one step and the difference signal. An inverse number of the data is, as the correction data of each diaphragm position, stored in the memory 232 in response to an address signal corresponding to each diaphragm position.

Another example of the structure of an endoscope apparatus having the automatic light adjustment means capable of correcting the loop gain will now be described.

Figure 27:
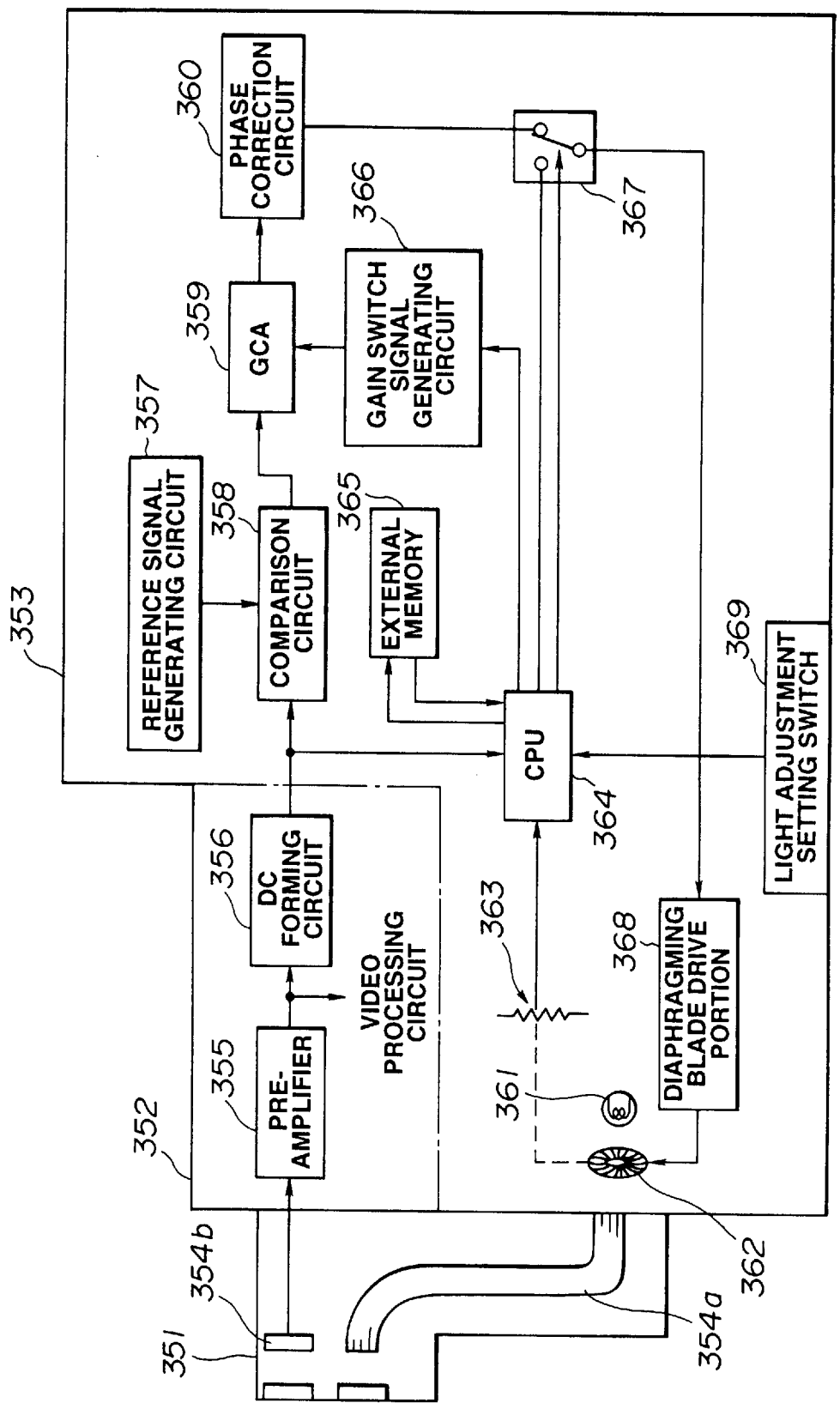
FIG. 27 is a block diagram which illustrates a first structural example of an endoscope apparatus having an automatic light adjustment means capable of correcting a loop gain.

FIG. 27 illustrates a first example of the structure of the endoscope apparatus having the automatic light adjustment means capable of correcting the loop gain.

The endoscope apparatus shown in FIG. 27 comprises: an electronic endoscope 351 to be inserted into the coelom; a camera control unit 352 (hereinafter called "CCU") that receives an output signal from the electronic endoscope 351 to transmit a video signal; and a light source unit 353 for supplying light to the electronic endoscope 351. The CCU 352 comprises a preamplifier 355 for amplifying an output signal from a solid-state image sensing device 354b disposed in the electronic endoscope 351 and arranged to converting the image of a subject into an electric signal; a DC forming circuit 356 for smoothing the output signal from the pre-amplifier 355 with an arbitrary time constant; and a video processing circuit (omitted from illustration).

The light source unit 353 comprises: a reference signal generating circuit 357 for transmitting a signal corresponding to the brightness that can be set arbitrarily by an operator using the panel; a comparison circuit 358 that receives an output signal from the DC forming circuit 356 and subjects it to a comparison with an output signal from the reference signal generating circuit 357 to transmit the difference; a gain control amplifier (GCA) 359 for switching the gain of the output signal from the comparison circuit 358 in response to a control signal supplied from outside; a phase correction circuit 360 for correcting the frequency characteristics; a lamp 361 for irradiating a subject with light; a diaphragming blade 362 for diaphragming the quantity of light emitted from the lamp 361; a diaphragming blade drive portion 368 for operating the diaphragming blade 362; a potentiometer 363 having a shaft that moves in synchronization with the drive shaft of the diaphragming blade 362; a CPU 364 that receives the output from the DC forming circuit 365 and that from the potentiometer 363 to perform a predetermined calculation; an external memory 365 connected to the CPU 364 and arranged to store data calculated by the CPU 364 in response to an address signal corresponding to the output from the potentiometer 363; a gain switch signal generating circuit 366 that receives data transmitted from the CPU 364, which has read data corresponding to the address signal of the external memory 365 to transmit the same to a gain switching control terminal of a GCA 359; and a switch 367 that receives the output from the CPU 364 and that from the phase correction circuit 360 to select the output from the CPU 364 during a period from commencement of a predetermined calculation in accordance with the output from a light adjustment setting switch 369 to completion of the calculation.

Irradiation light emitted from the lamp 361 is, through the diaphragming blade 362, made incident upon the base portion of a light guide 354a passing through the electronic endoscope 351. Irradiation light is then transferred to the leading portion of the electronic endoscope 351 through the light guide 354 so as to be applied to a portion to be observed.

The operation of the thus-constituted endoscope apparatus will now be described.

Referring to FIG. 27, when an operator depresses the light adjustment setting switch 369 after electric power has been supplied, the CPU 364 starts a predetermined calculation to obtain the gain of the light adjustment means with respect to the diaphragm position. The switch 367 selects the output from the CPU 364 as an input signal.

The CPU 364 transmits a control signal to the diaphragming blade drive portion 368 to operate the diaphragming blade 362 in order to make the output from the potentiometer 363 change in a stepped manner at each predetermined quantity. Specifically, the CPU 364 monitors the output from the potentiometer 363 to cause the output from the potentiometer 363 to be changed in a stepped manner at predetermined intervals in a direction from the full open to the closed position and to cause the value of the counter in the CPU, which similarly changes in that stepped manner, and the output from the potentiometer 363 to coincide with each other by controlling the position of the diaphragming blade 362. Thus, the CPU 364 operates the diaphragming blade 362 in the stepped manner to receive the level of the output signal from the DC forming circuit 356 at each position.

Figure 28:
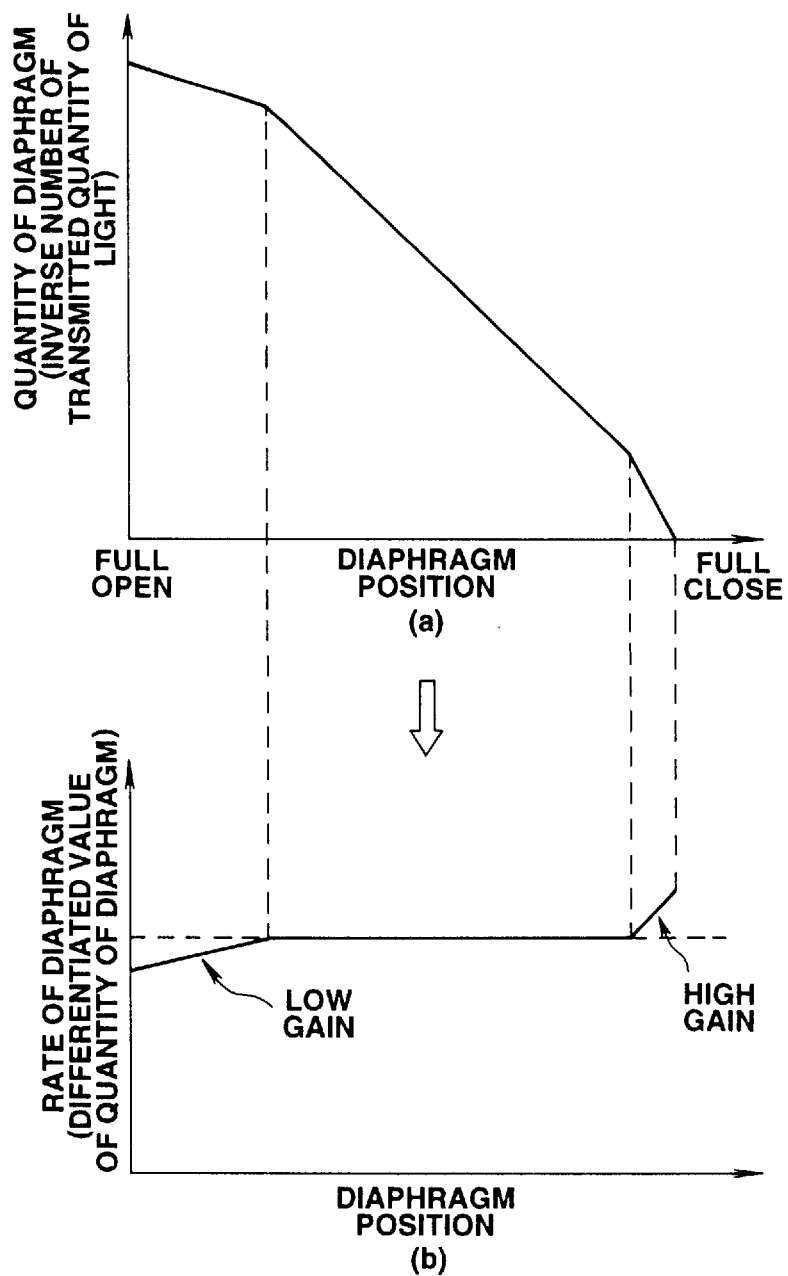
FIG. 28 is a characteristic graph which illustrates the relationship among the diaphragm position of a diaphragming blade, the quantity of diaphragm and the diaphragm ratio of the light source unit having the structure shown in FIG. 27.

In accordance with the relationship between the diaphragm position and the quantity of diaphragm shown in FIG. 28(a), the CPU 364 calculates a difference signal (Vn–1–Vn) between the output signal level Vn from the DC forming circuit 356 at each position of the diaphragming blade 362 at the time of the step operation and the output signal level Vn–1 from the DC forming circuit 356 at a position one step forward the present diaphragm position. Then, the ratio of the difference signal (Vn–1–Vn) and output level Vn–1 is obtained. That is, the difference (Vn–1–Vn) between the output signal level from the DC forming circuit 356 at each diaphragm position and the output signal level from the DC forming circuit 356 at the position one step forward is divided by the output signal Vn–1 from the DC forming circuit 356 at a position forwards by one step, and then the result of the division is multiplied by constant A. The thus-obtained value, that is, the diaphragm ratio shown in FIG. 28(b) is, with the address signal with respect to the output signal from the potentiometer 363, written on the external memory 365.

The foregoing predetermined process is performed until the diaphragming blade 362 is fully closed, and then the switch control output is transmitted from the CPU 364 so that the switch 367 selects the output from the phase correction circuit 360.

Figure 29:
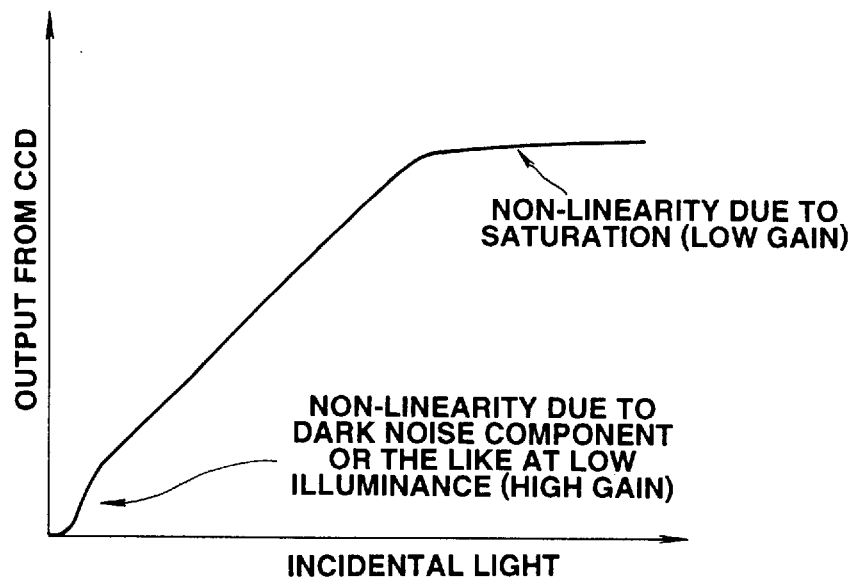
FIG. 29 is a characteristic graph which illustrates the characteristics of an output from a CCD with respect to the incident light in the electronic endoscope having the structure shown in FIG. 27.

Then, an operation similar to that performed by the usual automatic light adjustment circuit is performed. That is, the output signal from the solid-state image sensing device 354b, which is in proportion to the light quantity of the subject, is supplied to the DC forming circuit 356 through the pre-amplifier 355 as shown in FIG. 29. In the DC forming circuit 356, the signal is integrated. The output from the DC forming circuit 356 is subjected to a comparison with the output from the reference signal generating circuit 357 so that a signal corresponding to the difference is transmitted. As the output from the reference signal generating circuit 357, a signal in proportion to the light adjustment level set by an operator is transmitted.

Figure 30:
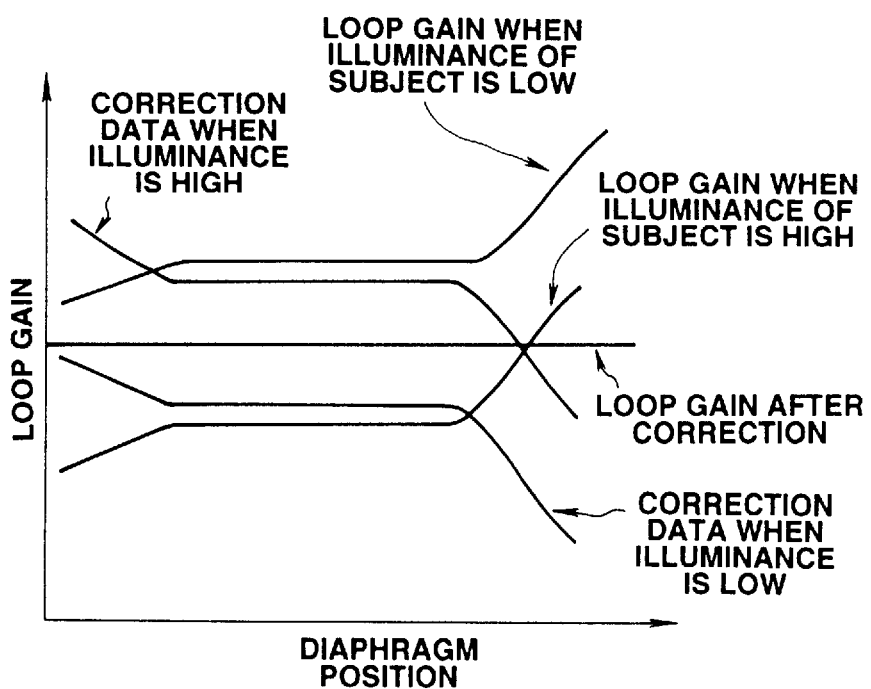
FIG. 30 is an operation explanatory view which illustrates correction of the loop gain of light adjustment by a CPU in the light source unit having the structure shown in FIG. 27.

The difference signal, which is the output from the comparison circuit 358, is amplified by the GCA 359. The degree of amplification performed in the GCA 359 is, as shown in FIG. 30, not constant as is realized in the usual automatic light adjustment circuit, but it is changed in accordance with the output from the potentiometer 363. The CPU 364 reads the correction value calculated in the foregoing initial operation and stored in the external memory 365 with the address corresponding to the output value from the potentiometer 363 so as to transmit a gain switching signal from the gain switching signal generating circuit 366 to the GCA 359 to make the degree of amplification to correspond to the correction value.

The phase of the difference signal amplified by the GCA 359 is corrected by the phase correction circuit 360 so as to be supplied to the diaphragming blade drive portion 368 through the switch 367. As a result, the diaphragming blade 362 is operated in a direction in which the output from the comparison circuit 358 is reduced.

Therefore, when an instruction of writing into the external memory 365 is made by an operator, the CPU 364 operates the diaphragming blade 362 in a stepped manner by a predetermined interval. Thus, signals in proportion to the illumination of the subject at this time are sequentially supplied, and the differences from signals adjacent to the signals supplied sequentially are obtained. The thus-obtained differences are calculated in a predetermined manner. The obtained correction value is written on the address of the external memory 365 corresponding to the diaphragming position or the degree of opening of the diaphragming blade 362. After data with respect to all diaphragm positions or degrees of opening has been written, writing into the external memory 365 is inhibited. Data corresponding to the diaphragm position or the degree of opening is read arbitrarily to correct the loop gain in the GCA 359, and the phase is corrected in the phase correction circuit 3600 so as to control the diaphragming blade drive portion 368.

As a result, even if the combination of the units in the system is changed, the previous presetting performed by a user enables the optimum response to be automatically calculated and set. Therefore, hunting can be prevented regardless of the combination and the response can be improved.

As a result of the foregoing structure, the setting of the light adjustment characteristics performed at the time of use enables the gain at the diaphragming blade position in the total system to be obtained. A correction value corresponding to the value of the gain can be calculated and stored, and therefore the loop gain of the light adjustment means can be corrected arbitrarily in accordance with the diaphragming blade position at the time of the automatic light adjustment operation. Therefore, the diaphragm can be controlled always adequately without hunting regardless of the combination with a camera control unit in a case where a plurality of camera control units are used.

Figure 31:
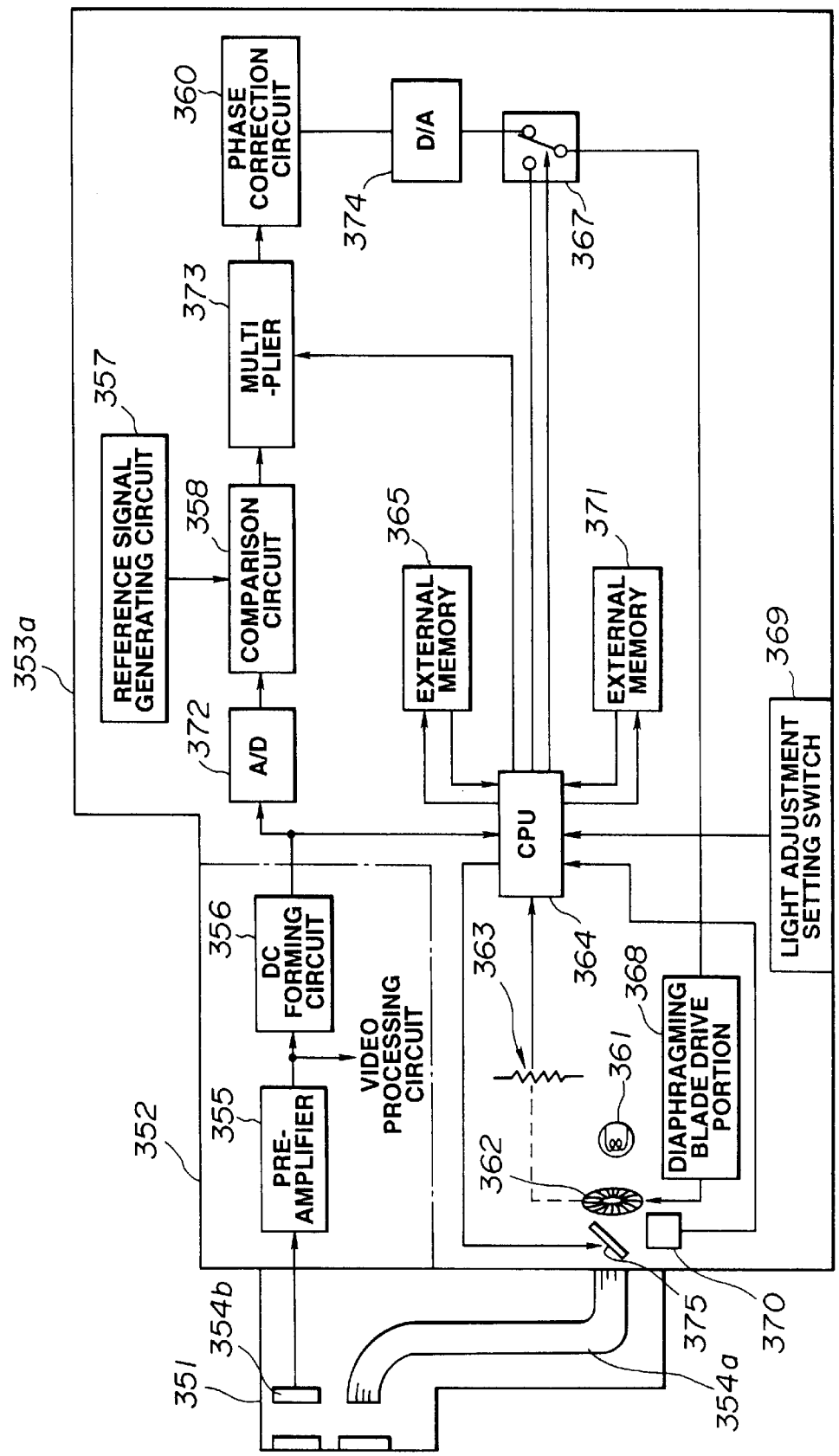
FIG. 31 is a block diagram which illustrates a second structural example of an endoscope apparatus having an automatic light adjustment means capable of correcting the loop gain.
Figure 32:
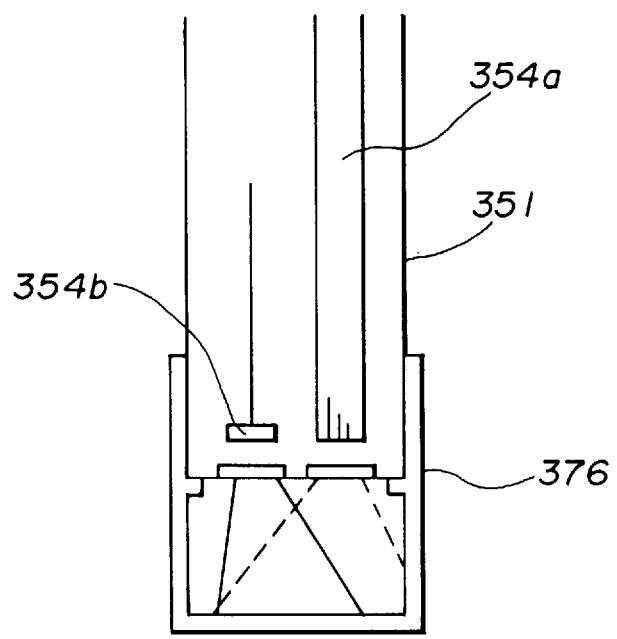
FIG. 32 is an explanatory view which illustrates an adapter that can be connected to the leading portions of an electronic endoscope.

FIG. 31 illustrates a second structural example of an endoscope apparatus having the automatic light adjustment means capable of correcting the loop gain. Since the second structural example has an arrangement substantially similar to that according to the first structural example shown in FIG. 27, only the different structures will now be described in such a manner that the same structures are given the same reference numerals and their descriptions are omitted here.

The second structural example shown in FIG. 31 has an arrangement in which a light source unit 353a comprises an A/D converter 372 that receives the output signal from the DC forming circuit 356 to convert it into a digital signal. Furthermore, a multiplier 373 for multiplying the output signal from the comparison circuit 358 by a control signal supplied from outside is disposed between the comparison circuit 358 and the phase correction circuit 360. The output from the A/D converter 372 and the output signal from the reference signal generating circuit 357 are subjected to a comparison by the comparison circuit 358. In the multiplier 373, the difference signal, which is output from the comparison circuit 358, is multiplied by a control signal supplied from outside so as to be supplied to the phase correction circuit 360. Furthermore, a D/A converter 374 for converting the output from the phase correction circuit 360 into an analog signal is provided. Thus, the phase of the output from the multiplier 373 is corrected by the phase correction circuit 360, and it is then converted into an analog signal by the D/A converter 374 before it is supplied to the switch 367.

A half mirror 375 is disposed on the emission side of the diaphragming blade 362, while a light receiving device 370 is disposed in the reflection direction of the half mirror 375. Thus, the output from the light receiving device 370 is arranged to be received by the CPU 364. In addition to the external memory 365 for storing calculation data in the CPU 364 in response to the address signal corresponding to the output from the potentiometer 363, another external memory 371 for storing calculation data in the CPU 364 in response to the output from the DC forming circuit 356 is provided. The CPU 364 receives the output from the DC forming circuit 365, the output from the potentiometer 363, and the output from the light receiving device 370 to perform predetermined calculations.

With the foregoing structure, when an operator depresses the light adjustment setting switch 369 for the initial setting, the control performed by the CPU 364 causes the half mirror 375 to be introduced into the emission light passage. Furthermore, the CPU 374 starts a predetermined calculation in order to obtain the gain of the light adjustment means with respect to the diaphragm position. The switch 367 selects the output from the CPU 364 as the input signal until the CPU 364 completes the calculation.

Similarly to the structural example shown in FIG. 27, the CPU 364 causes the output from the potentiometer 363 to be changed in a stepped manner at each predetermined quantity by transmitting the control signal to the diaphragming blade drive portion 368 to drive the diaphragming blade 362. By operating the diaphragming blade 362 in the stepped manner as described above, the CPU 364 receives the output signal level from the DC forming circuit 356 and the output signal level from the light receiving device 370 at each position.

The CPU 364 calculates the ratio of the difference among the output signal levels of the light receiving device 370 at each position at the time of the stepped-operation of the diaphragming blade 362 with respect to the output signal level from the light receiving device 370 when the diaphragming blade 362 is fully opened so as to obtain a value in proportion to the gain at each position of the diaphragming blade 362. Furthermore, the CPU 364 obtains a value corresponding to the gain of the CCU 352 with respect to the emitted light in accordance with the output signal from the DC forming circuit 356 and the output from the light receiving device 20 at each position of the diaphragming blade 362 at the stepped-operation.

The CPU 364 obtains the difference between the output signal level from the light receiving device 370 at each diaphragm position and the output signal level from the light receiving device 20 one step forwards the present diaphragm position. The difference is divided by the output signal level from the light receiving device 370 at the full opened position, the obtained value being written on the external memory 365 with the address signal corresponding to the output signal from the potentiometer 363.

The CPU 364 receives output signals from the light receiving device 370 and the DC forming circuit 356 when the diaphragming blade 362 is operated in the stepped manner. In accordance with the output signals from the light receiving device 20 one step forwards from the present diaphragm position and the DC forming circuit 356, the difference from the output from the light receiving device 370 at the present diaphragm position and the output from the light receiving device 370 one step forwards and the difference between the output from the DC forming circuit 356 at the present diaphragm position and the output from the DC forming circuit 356 one step forwards are calculated. The difference signal from the DC forming circuit 356 is divided by the difference signal of the light receiving signal 50. The obtained value is written on the external memory 371 with the address signal which corresponds to the output signal from the DC forming circuit 356.

The foregoing predetermined process is performed until the diaphragming blade is fully closed, and then a switch control output is transmitted from the CPU 364. Thus, the switch 367 selects the output from the phrase correction circuit 360. As a result of the control performed by the CPU 364, the half mirror 375 is retracted from the optical path.

Then, an operation similar to that performed by a usual automatic light adjustment circuit is performed such that the output signal from the solid-state image sensing device 354b in proportion to the light quantity of the subject is received by the DC forming circuit 356 through the pre-amplifier 355. In the DC forming circuit 356, the signal is integrated. The output from the DC forming circuit 356 is converted into a digital signal by the A/D converter 372, and it is then subjected to a comparison with the output from the reference signal generating circuit 357 so that a signal is transmitted in accordance with the difference. As for the output from the reference signal generating circuit 357, a signal that is in proportion to the light adjustment level set by a user is transmitted.

The difference signal, which is the output from the comparison circuit 358, is multiplied by the output from the CPU 364. At this time, the CPU 364 reads, with the address corresponding to the output value from the potentiometer 363, the value corresponding to the gain of the diaphragming blade 362 at the diaphragm position calculated at the initial operation and stored in the external memory 365.

Furthermore, the value corresponding to the gain of the CCU 352 in accordance with the emitted light stored in the external memory 371 is read with the addresses corresponding to the output value from the DC forming circuit 356. The CPU 364 multiplies data from the external memory 365 and the external memory 371 to obtain the inverse number to be multiplied by the inverse number of the reference value so as to be transmitted to the multiplier 373 as a multiplier factor.

The phase of the difference signal multiplied with data of the CPU 364 in the multiplier 373 is corrected by the phase correction circuit 360, and then it is converted into an analog signal by the D/A converter 374. It is then supplied to the diaphragming blade drive portion 368 through the switch 367. As a result, the diaphragming blade 362 is operated in a direction in which the output from the comparison circuit 358 is reduced.

As described above, in this example, the light adjustment characteristics are set at the time of use so as to obtain the gain of the diaphragming blade at the diaphragming blade position and the output signal from the camera control unit, that is, the gain of the camera control unit in accordance with the quantity of light made incident upon the solid image sensing device. A correction value in accordance with the obtained value is calculated and stored, and thus the loop gain can be, at an arbitrary time at the time of the automatic light adjustment operation, corrected in accordance with the diaphragming blade position and the quantity of light made incident upon the solid state image sensing device. Therefore, adequate diaphragm control can always be performed without generation of hunting regardless of the combination of a plurality of the camera control units.

If a cap-like adapter 376, the inside surface of which is applied with paint having a uniform reflectance, is placed to cover the leading portion of the electronic endoscope 351 to set the light adjustment characteristics, saturation of the output from the CCU 352 during the calculation in the stepped operation can be prevented and therefore a calculation with excellent reproducibility can be performed. By employing the foregoing method, white balance adjustment can be performed simultaneously with setting of the light adjustment characteristics.

Figure 33:
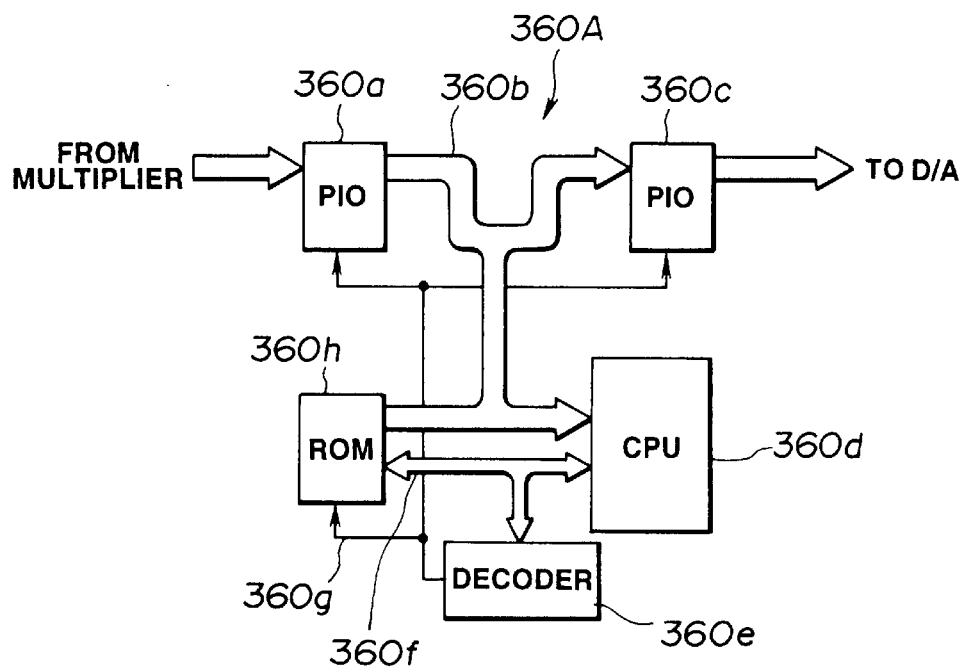
FIG. 33 is a block diagram which illustrates a structural example of a phase correction circuit of a light adjustment circuit to be disposed in the endoscope apparatus shown in FIG. 31.
Figure 34:
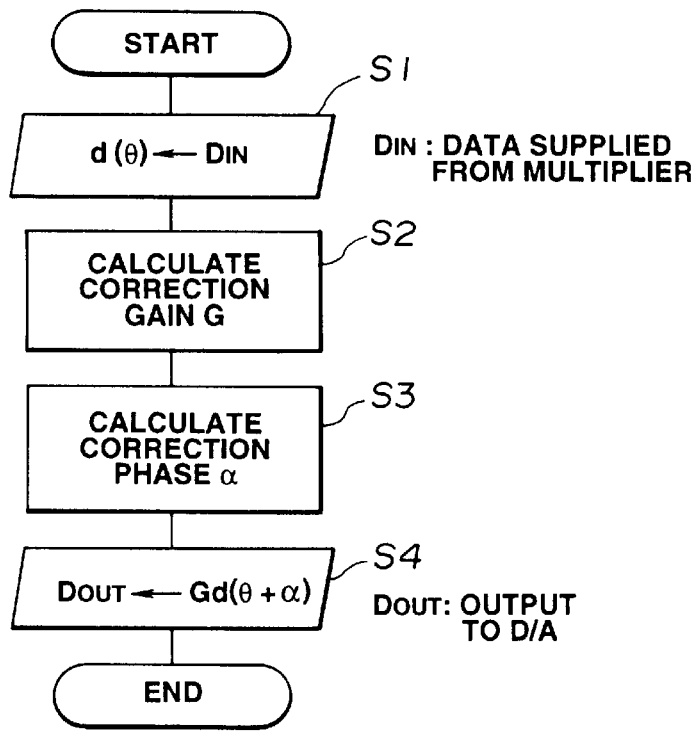
FIG. 34 is a flow chart which illustrates the operation of a calculating CPU in the phase correction circuit shown in FIG. 33.

FIG. 33 illustrates a structural example of a phase correction circuit of a light adjustment circuit provided in the endoscope apparatus shown in FIG. 31.

A phase correction circuit 360A shown in FIG. 33 has a PIO (Parallel Input/Output Controller) 360a for receiving the difference signal data supplied from the multiplier 373. The PIO 306a is connected to the calculating CPU 360d through a data bus 360b. Furthermore, a calculating CPU 360d, a ROM 360h in which a control program is stored, and a PIO 360c for transmitting calculated data obtained by correcting the phase of the difference signal data to the D/A converter 374 are connected to the data bus 360b. In addition, a decoder 360e for generating a chip selection signal 360g in accordance with the address data supplied from the calculating CPU 360d is provided for the data bus 360b. The decoder 360e is connected to the calculating CPU 360d and the ROM 360h through an address bus 360f. Although omitted from illustration, a control but for transferring a control signal transmitted from the calculating CPU 360d is connected to the PIO 360a, PIO 360c and the ROM 360h.

The operation of the thus-constituted phase correction circuit 360A will now be described. When electric power is supplied, the calculating CPU 360d loads the control program from the ROM 360h to initialize the PIO 360a and 360c ; before the calculating process is commenced calculating correction gain G in accordance with the magnitude of the difference signal data in step S2 and by calculating correction phase α in step S3. In accordance with the calculated data, the supplied difference signal data is corrected in step S4 to transmit $D_{out}$ to the D/A converter 374 through the PIO 360c.

By constituting the phase correction circuit as described above, the correction coefficient for correcting the difference signal can be changed to be adaptable to the hardware. Thus, the general-purpose properties can be improved. As for the correction coefficient of one hardware, a plurality of function tables are possessed to be adaptable to the change regions for the difference signal so that the accuracy in control can be improved.

Figure 35:
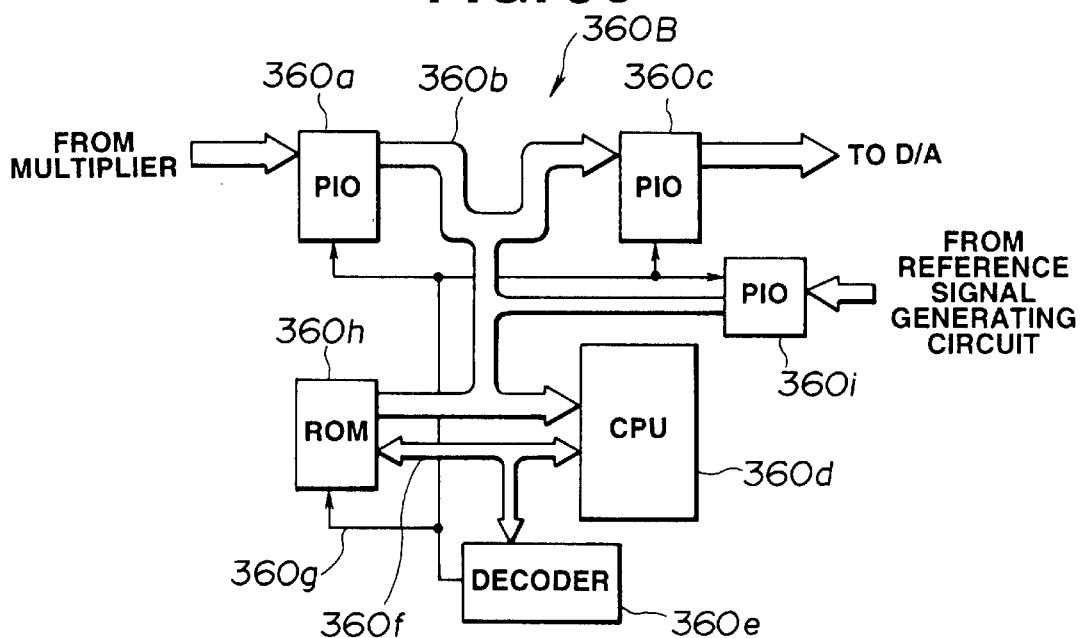
FIG. 35 is a block diagram which illustrates the structure of a modification of the phase correction circuit shown in FIG. 33.

A modification of the structure of the phase correction circuit shown in FIG. 33 will now be described with reference to FIG. 35. A phase correction circuit 360B according to this modification, in addition to the structure shown in FIG. 33, a PIO 360i for receiving data corresponding to the light adjustment level set by a using through the reference signal generating circuit 357. The PIO 360i is connected to the calculating CPU 360d through the data bus 360b.

Figure 36:
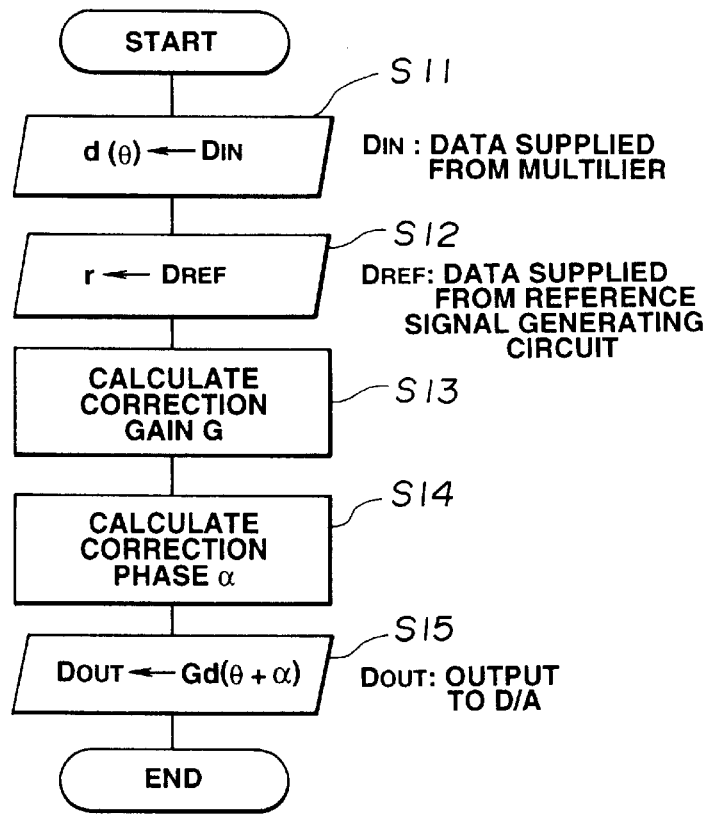
FIG. 36 is a flow chart which illustrates the operation of a calculation CPU in the phase correction circuit according to the modification shown in FIG. 35.

The phase correction circuit 360B according to this modification is operated similarly to the phase correction circuit 360A shown in FIG. 33. As described in a flow chart shown in FIG. 36, difference signal data $D_{IN}$ transmitted from the PIO 360a by the multiplier 373 is received in step S11. Then, reference signal data $D_{REF}$ transmitted from the reference signal generating circuit 357 is received from the PIO 360i in step S12. Then, the loop characteristics of the control system are optimized by calculating correction phase α in step S13 in accordance with the magnitude of the difference signal data. The thus-calculated data is used to correct the supplied difference signal data in step S15 to transmit it to the D/A converter 374 through the PIO 360c as $D_{out}$. That is, the correction coefficient is calculated while considering the reference value of the light adjustment level.

Since this modification enables the value of the light adjustment level set by the operator to be reflected on the calculation of the correction coefficients well as the magnitude of the difference signal, control adaptable to a finer condition for use can be performed in addition to the effect obtainable from the phase correction circuit shown in FIG. 33.

Although the descriptions have been made with reference to FIGS. 27 to 36 about the examples of the structure of the light adjustment circuit for adjusting light by using the electronic endoscope, the present invention is not limited to this. A similar effect can be obtained from a structure in which an external camera is attached to an optical endoscope.

The foregoing structure of the automatic light adjustment means having the arrangement that the gain of the diaphragm at each diaphragm position is obtained to calculate the data for correcting the loop gain of the automatic light adjustment means, and the correction value is stored so that the response of the light quantity control means is corrected in accordance with the stored correction value. Therefore, the combination of the image pickup unit and the light source unit is not limited. Thus, an effect can be obtained in that an automatic light adjustment means capable of operating smoothly and exhibiting excellent response without generation of hunting can be realized without a necessity of modification regardless of the combination.

A seventh embodiment of the present invention will now be described with reference to FIGS. 37 and 38. The seventh embodiment has an arrangement in which the control portion in the light source unit is constituted by a programmable integrated circuit to enable several kinds of endoscopes, such as electronic endoscopes and fiber scopes, to be used in a combined manner.

Figure 37:
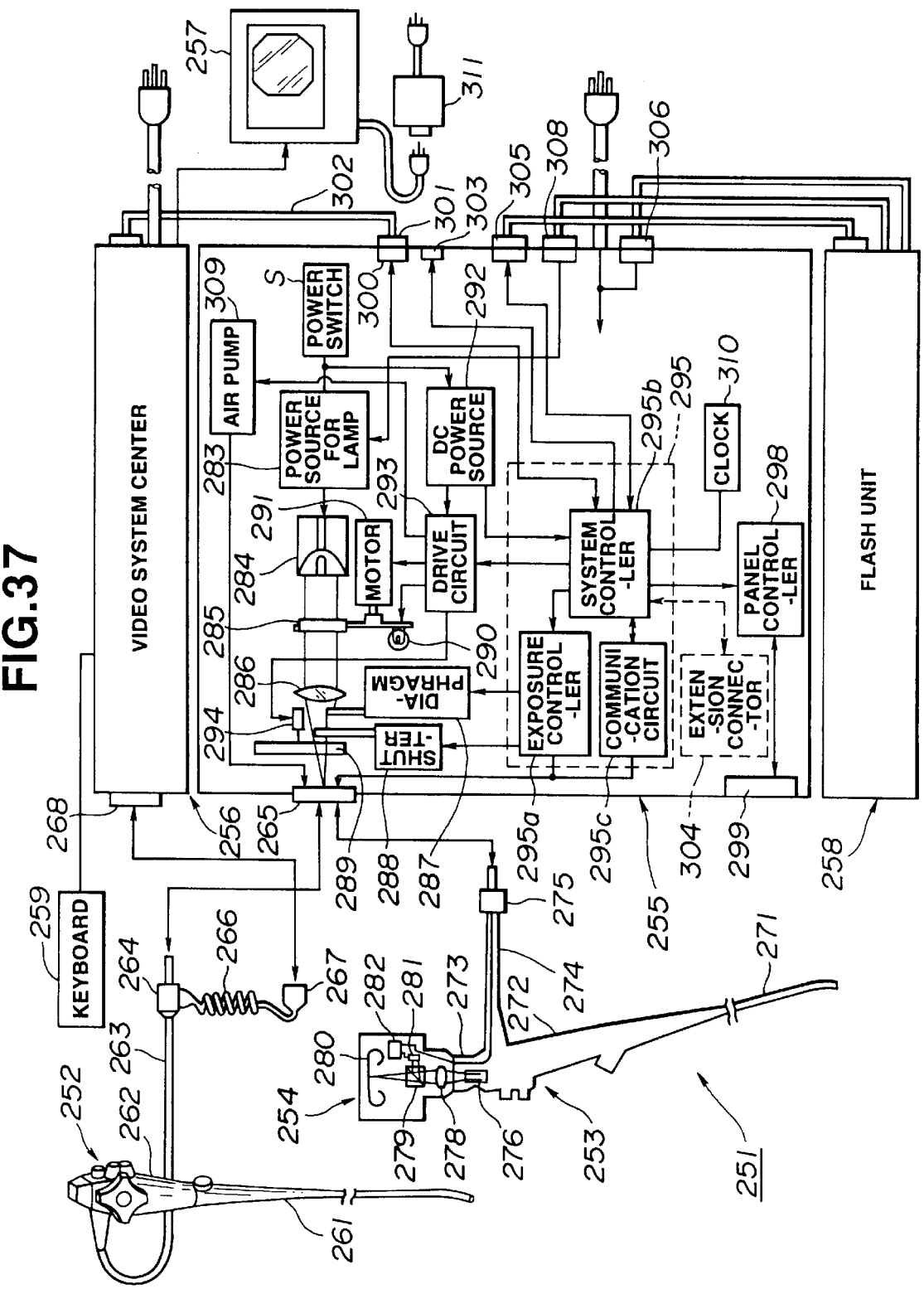

An endoscope system 251 according to the seventh embodiment is able to realize endoscope apparatuses having different structures as shown in FIG. 37 since it comprises a field sequential electronic endoscope 252, a fiber scope 253, a photographing unit 254 to be attached to the fiber scope 253, a light source unit 255 capable of adapting to either the field sequential electronic endoscope 252 or the fiber scope 253, a video system center 256 for use together with the field sequential electronic endoscope 252, a color monitor 257 to be connected to the video system center 256, and a flash unit 258 that can be connected to the light source unit 255 and for use to emit flash light. The video system center 256 is connected to a keyboard 259.

The electronic endoscope 252 comprises an elongated insertion portion 261, an operation portion 262 and a universal cable 263. The universal cable 263 has an end at which a light source connector 264 is attached so as to be detachably connected to a connector receiver 265 of the light source unit 255. A signal connector 267 at an end of a signal cable 266 extending from the light source connector 264 can be detachably connected to a connector receiver 268 of the video system center 256.

The insertion portion 261 and the universal cable 263 include a light guide (omitted from illustration) inserted thereto. Thus, the connection established between the light source connector 264 and the light source unit 255 causes irradiation light to be supplied from the light source unit 255. The insertion portion 261 has an end at which an objective lens and a CCD disposed on the focal plane of the objective lens (which are omitted from illustration) are disposed. A signal photoelectrically converted by the CCD is supplied to a signal processing circuit in the video system center 256 when the signal connector 267 is connected to the video system center 256 so that a video signal is generated which is displayed on the color monitor 257.

The fiber scope 253 has an elongated insertion portion 271, an operation portion 272, an ocular portion 273 and a light guide cable 274. The light guide cable 274 has an end at which a light source connector 275 is disposed. Thus, the light guide cable 274 can be detachably connected to the connector receiver 265 of the light source unit 255.

The insertion portion 271 and the light guide cable 274 include a light guide (omitted from illustration) inserted thereto. When the light source connector 275 is connected to the light source unit 255, irradiation light can be supplied from the light source unit 255. The insertion portion 271 has an end at which an objective lens (omitted from illustration) is disposed, the objective lens having the focal plane on which the leading surface of an image guide 276 is disposed. Thus, an optical image can be transferred to the end surface facing the ocular portion 273 to be observed through an ocular window of the ocular portion 273.

The photographing unit 254 to be connected to the ocular portion 273 forms an optical image on a film 280 through a lens 278 and a beam splitter 279. The quantity of light to which the film 280 is exposed is detected by a sensor 281 for receiving light reflected by the beam splitter 279 so as to be supplied to a control circuit 282.

The control circuit 282 is connected to an electric contact (omitted from illustration) of the light source connector 275 through a signal line so as to be connected to an electric system in the light source unit 255.

The light source unit 255 has a lamp 284, such as a xenon lamp, to which electric power is supplied from a lamp power supply circuit 283 which is turned on when a power switch S is switched on. Light emitted from the lamp 284 is allowed to pass through a filter 285, a lens 286, a diaphragm 287 and a shutter 288 before it passes through an RGB rotational filter 289 which can be retracted from the optical path or it does not pass through the RGB rotational filter 289. Then, light is supplied to the end surface of the light guide at the light source connector 264 or 275 to be connected to the connector receiver 265.

The filter 285 is attached to either of filter turrets, the residual filter turret having an emergency lamp 290 attached thereto. The rotation of a motor 291 enables the filter 285 or the emergency lamp 290 to be selectively disposed on the optical path. The motor 291 and the emergency lamp 290 are operated by a drive circuit 293 to which electric power is supplied from a DC power supply circuit 292. The drive circuit 293 rotates a motor 294 that rotates the RGB rotational filter 289.

The diaphragm 287 and the shutter 288 are controlled by an exposure controller 295a constituted by a PGA 295 and formed in a case where, for example, the fiber scope 253 is connected. The exposure controller 295a is connected to an electric contact (omitted from illustration) of the connector receiver 265. When the light source connector 275 of the fiber scope 253 is connected to the connector receiver 265, the exposure controller 295a is connected to the control circuit 282 of the photographing unit 254 through the fiber scope 253 to control the quantity of exposure in response to a signal supplied from the control circuit 282.

The operation of the exposure controller 295a is controlled by a system controller 295b. The system controller 295b is supplied with electric power from the DC power supply circuit 292. The system controller 295b is connected to an electric contact (omitted from illustration) of the connector receiver 265 through a communication circuit 295c having a combination detection function. When the connection of the fiber scope 253 is detected or when the light source connector 275 is connected, the connection of the photographing unit 254 is detected from the communication with the control circuit 282 through the fiber scope 253 so as to control the operation of the control circuit 282 and control the operation of the exposure controller 295a in response to a signal supplied from the control circuit 282.

In a case where the electronic endoscope 252 is connected to the light source unit 255 in place of the fiber scope 253, the communication circuit 295c detects the connection of the electronic endoscope 252 so as to realize a circuit function adaptable to the electronic endoscope 252.

The system controller 295b controls the operation of the drive circuit 293. The system controller 295b is connected to an operation panel 299 through a panel controller 298 so as to set the controlled contents of the system controller 295b or change the contents of display on a display portion of the operation panel 299 in accordance with the set state when the switch of the operation panel 299 is switched on.

The system controller 295b is electrically connected to the video system center 256 through a cable 302 having an electric connector 301 connected to an electric connector receiver 300. Thus, the system controller 295b synthesizes the signal processing to be performed by the video system center 256 and the RGB irradiating operation to be performed in the light source unit 255 or generates a light adjustment signal in response to a brightness signal supplied from the video system center 256 so as to control the diaphragm drive through a diaphragm drive circuit formed in place of the exposure controller 295a in order to perform the automatic light adjustment.

The system controller 295b is connected to an option connector 303 and a machine extension connector 304.

The system controller 295b is connected to a flash unit 258 through a flash signal connector 305 connected to the flash signal connector to control the operation of the flash unit 258 or control the operation of the shutter 288 in synchronization with the operation of the flash unit 258.

The flash unit 258 is supplied with AC power through a flash unit AC connector 306 to be connected to a flash unit AC connector receiver provided for the light source unit 255. The flash unit 258 is connected to the lamp power supply circuit 283 through a flash unit connector 308 to be connected to the flash unit connector receiver so as to cause the lamp 284 to emit flash light through the lamp power supply circuit 283.

The light source unit 255 accommodates an air pump 309 so as to supply air or the like to the electronic endoscope 252 or the fiber scope 253 connected to the connector receiver 265. The air pump 309 is operated by the drive circuit 293. The system controller 295b is connected to a clock 310 to control the time and uses time information obtainable from the clock 310. Note that the color monitor 257 is connected to a commercial power source through an insulating transformer 311.

FIG. 37 illustrates the structure of the PGA 295 constituted in a case where the fiber scope 253 is connected to the light source unit 255 (in this case the RGB rotational filter 289 is retracted from the optical path). The PGA 295 has the functional structure as shown in a block diagram illustrated in FIG. 38. A combination detection means signal supplied from the combination detection formed in the communication circuit 295c is supplied to a binary-coding data selection means 322 constituting the system controller 295b.

The binary-coded data selection means 322 selectively reads binary-coded data of the corresponding functional structure from binary-coded data storage means 323a to 323f to notify a constitution instruction means 324 that the data has been selected. In accordance with the notification, the constitution instruction means 324 issues an instruction to a digital circuit constituting means 325 to constitute a circuit in accordance with the selected data. The binary-coded data storage means 323a to 323f are constituted by ROMs similarly to the ROMs 233 and 234 according to the sixth embodiment shown in FIG. 24.

Figure 38:
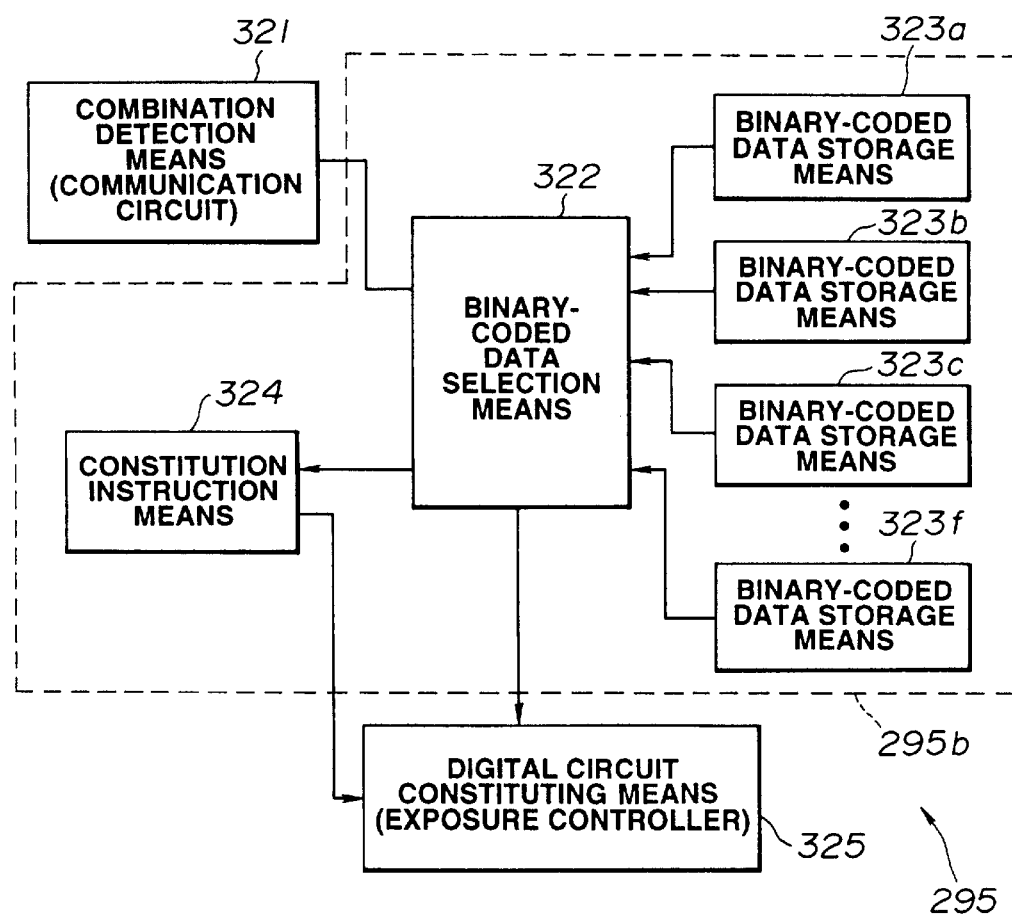

In a case where the fiber scope 253 is connected to the light source unit 255, the digital circuit constituting means 325 constitutes the exposure controller 295a as shown in FIG. 38. At this time, the RGB rotational filter 289 is removed from the optical path. In a case where the field sequential electronic endoscope 252 is connected, the digital circuit constituting means 325 constitutes a light adjustment circuit and a rotational filter control circuit as described in the sixth embodiment. At this time, the RGB rotational filter 289 is moved into the optical path.

In this embodiment, a combination with a simultaneous-type electronic endoscope (omitted from illustration) may be employed. In a case where the simultaneous-type electronic endoscope is connected, the digital circuit constituting means 325 constitute a light adjustment circuit. At this time, the RGB rotational filter 289 is removed from the optical path.

In a case where a unit except the foregoing combination is connected, the functional structure can be selectively set.

A structure similar to that according to the sixth embodiment may be employed in which the correction data of the loop gain in the connected combination is obtained at the time of the system start to perform optimum automatic light adjustment.

Since this embodiment has an arrangement in which only the required functional blocks corresponding to the functions of the connected units are constituted in the light source unit 255, required functions can be realized without a necessity of enlarging the size of the circuit. As a result, the size of the apparatus can be reduced and the electric power consumption can be decreased.

An example of a circuit structure of a portion of the endoscope apparatus in which the programmable integrated circuit is used will now be described.

The conventional programmable integrated circuit has an arrangement that the storage device, in which circuit data for determining the operation of the circuit is stored, is connected to the reloadable circuit device to constitute a circuit having desired functions. Therefore, the functional structure of the programmable integrated circuit of the foregoing type cannot be changed to another functional structure until it is rewritten by connecting, in a non-activated state, a storage device, in which another circuit data has been stored.

Accordingly, an example of the structure of an electronic circuit will now be described with reference to FIGS. 39 and 40 which is capable of changing the function of the programmable integrated circuit if necessary even if the system is being operated.

Figure 39:
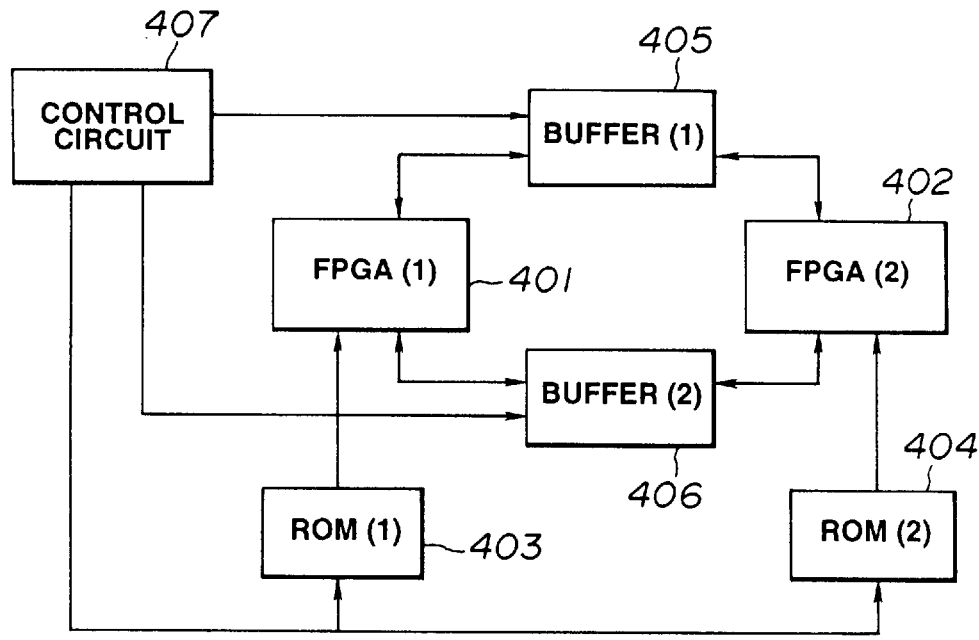
FIG. 39 is a block diagram which illustrates a structural example of an electronic circuit capable of changing the function of the programmable integrated circuit if necessary even if the apparatus is being operated.
Figure 40:
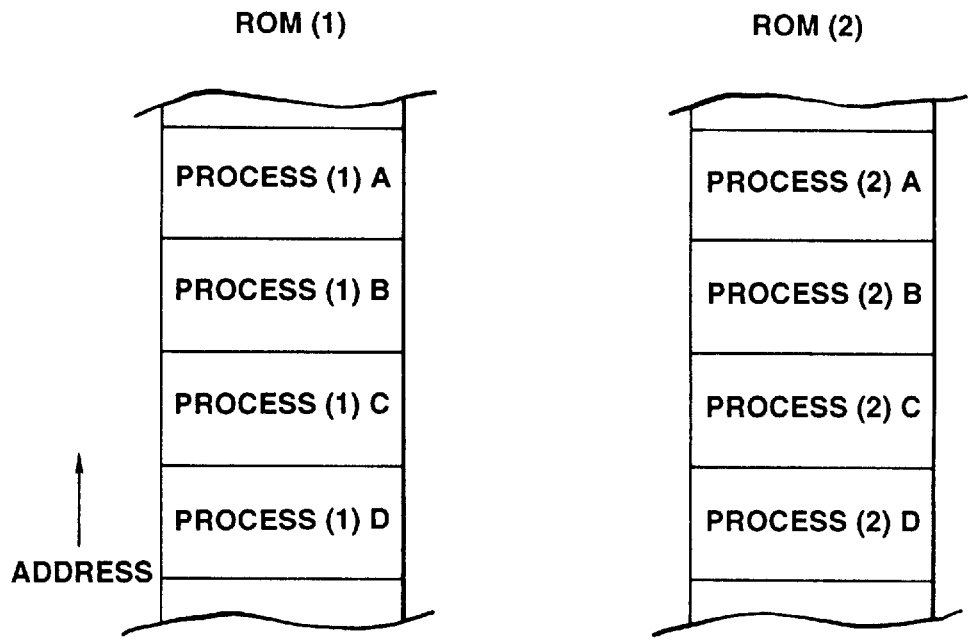
FIG. 40 is an explanatory view which illustrates an example of circuit data stored in the ROM shown in FIG. 39.

The electronic circuit shown in FIG. 39 has a programmable integrated circuit for constituting a digital circuit such as a logical circuit. For example, two FPGAs may be provided as the programmable integrated circuit.

A ROM (1) 403 and a ROM (2) 404 for defining the circuit functions such as wiring information and logic function are respectively connected to the two FPGAs, that is an FPGA (1) 401 and an FPGA (2) 402. Furthermore, a buffer (1) 405 and a buffer (2) 406 for temporarily storing processed data are respectively connected to the FPGA (1) 401 AND THE FPGA (2) 402.

Furthermore, a control circuit 407 including a CPU is provided, the control circuit 407 acting to control the FPGA (1) 401 and FPGA (2) 402, to control rewriting the operation functions of the FPGAs, and to control timing of input/output data to and from the FPGAS.

In the electronic circuit constituting the foregoing digital circuit, the data processing to be performed at the time of the operation can be divided into a plurality of time sequential processes. In this embodiment, data to be processed and processed data for each process are temporarily stored in the buffers 405 and 406 so as to perform a sequential process such that the circuit structures of the FPGAs 401 and 402 are rewritten at each processing.

An example of circuit data stored in the foregoing ROM (1) 403 and the ROM (2) 404 will now be described with reference to FIG. 40. FIG. 40 is an explanatory diagram illustrating an example of a memory space in each of the ROMs 403 and 404. As shown in FIG. 40, the ROMs 403 and 404 store, in the memory space thereof, circuit data items for defining the circuit structure for each of the plurality of time sequential processes while dividing them into blocks in the form of processes A, B, C, D and so forth corresponding to the respective processes. The control circuit 407 initially prepares, in the buffer (1) 405, data to be processed and reads circuit data for processing the foregoing data to be processed from the ROMs 403 and 404 to supply data to the FPGAs 401 and 402 to program the circuit function. As a result, the FPGAs 401 and 402 perform desired processes of the data to be processed. The FPGAs 401 and 402, for example receive data from the buffer (1) 405 to perform the processes and write the output onto the residual buffer (2) 406. For example, data stored in the buffer (1) 405 is processed by the FPGA (1) 401, and then the processed data is written on the buffer (2) 406. Then, data in the buffer (2) 406 is processed by the FPGA (2) 402, and the processed data is written on the buffer (1) 405.

Another arrangement may be employed in which the data prepared in the buffer (1) 405 is processed in parallel by the FPGAs (1) 401 and (2) 402, and the processed data is written on the buffer (2) 406. Another arrangement may be employed in which the data to be processed prepared in the buffer (1) 405 is processed by the FPGA (1) 401, and then the data is directly supplied to the FPGA (2) 402 to be processed in series in the FPGA (2) 402, and then the processed data is written on the buffer (2) 406. The processed data may be rewritten on the original buffer. In this case, one buffer can be omitted from the structure.

When the control circuit 407 recognizes that the data processed by the FPGA has been written on the buffer, the control circuit 407 reads circuit data for the next process from the ROMs 403 and 404 if necessary so as to rewrite the circuit structures of the FPGAs 401 and 402. The rewritten FPGAs 401 and 402 sequentially perform the processing.

That is, when the data to be processed is prepared in the buffers 405 and 406 connected to the FPGAs 401 and 402, before the same are prepared, or after the same have been prepared, the blocks of the circuit data for performing required processing definition are selected and read from the ROMs 403 and 404 serving as the storage devices in which the circuit data for defining the operations of the FPGAs so as to be supplied to the FPGAs 401 and 402 so that the circuit structures of the FPGAs 401 and 402 are set. After the data processing has been performed in the FPGAs 401 and 402 and the results of the processing have been written on the buffers 405 and 406, data of the results of the processing is processed as desired by another FPGA or by the same FPGA, the circuit structure of which has been changed and thus the contents of process of which have been set again.

The programmable integrated circuit for use in this embodiment is not limited to the structure consisting of the two FPGAs shown in FIG. 39. A structure having one FPGA may be employed with which the circuit is sequentially rewritten to perform the processing. A structure having three or more FPGAs may be employed in which a desired process can be performed while sequentially rewriting the circuit structure to change the function. In place of the FPGA, another programmable integrated circuit may be employed.

As a result of the foregoing structure, one or a plurality of programmable integrated circuits can be operated while changing their functions to be adaptable to the required digital signal processing. Thus, even if the apparatus is being operated, the function of the programmable integrated circuit can be changed if necessary. Therefore, a plurality of functions can be operated in series. As for the functions that cannot be operated simultaneously, circuits having a plurality of functions can be constituted in one programmable integrated circuit. Therefore, the number of ICs in the circuit having the required function can be decreased, and therefore the circuit structure can be simplified. Even if the programmable integrated circuit is used, the number of the FPGAs can be decreased and accordingly the circuit can be constituted by using a reduced number of chips. Thus, the size of the circuit can be reduced.

Figure 41:
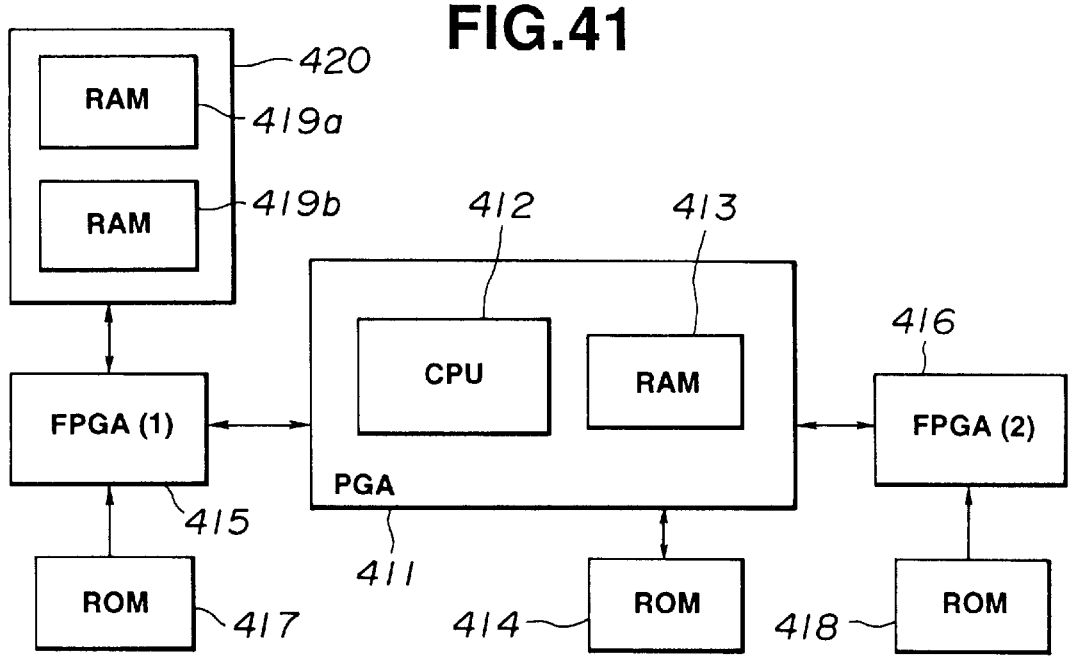
FIG. 41 is a block diagram which illustrates an example of a structure in which a digital circuit including a CPU is constituted by a programmable integrated circuit.

An example will now be described with reference to FIG. 41 which has an arrangement that a digital circuit including a CPU is, as an electronic circuit using the programmable integrated circuit, constituted by a programmable integrated circuit.

In a case where the apparatus is constituted by using the programmable integrated circuit, the functions of the CPU and the like can be constituted by the programmable integrated circuits so as to easily constitute a circuit having a desired function or to easily change the function of the circuit. The structure shown in FIG. 41 may be considered as a structure in which the portion of the control circuit 407 shown in FIG. 39 is constituted by a programmable integrated circuit. Each FPGA shown in FIG. 41 may be arranged such that its function can be changed for each process as is employed by the structure shown in FIG. 39.

A PGA 411, which is a programmable integrated circuit, comprises a CPU cell 412 having the function of a CPU, and a RAM cell 413 for storing processed data or the like. A ROM 414 for storing circuit data for defining the circuit function of the CPU cell 412 is connected to the PGA 411. The PGA 411 receives circuit data in the ROM 414 to constitute a circuit having a predetermined function corresponding to the circuit data.

FPGA (1) 415 and FPGA (2) 416 for constituting circuits having predetermined functions are connected to the PGA 411 so as to control the FPGAs and to supply/receive data between chips. ROMs 417 and 418, in which circuit data for defining the circuit functions are stored, are connected to the FPGA (1) 415 and (2) 416. Furthermore, a RAM 420 having RAM cells 419a and 419b for storing processed data or the like is provided, the RAM 420 being connected to the FPGA (1) 415.

The PGA 411 is caused to have a circuit constituted in accordance with circuit data in the ROM 414 so as to have functions as an arithmetic unit (ALU) serving as a CPU function to act as a main control portion, a command register, and a command decoder and the like. The FPGA (1) 415 and FPGA (2) 416 are caused to have circuits constituted in accordance with circuit data in the ROMS 417 and 418 so as to have functions, such as interruption control, parallel input/output, serial communication and the like for receiving external state or transmitting a control signal from the control portion to the outside. When, for example, electric power is supplied, the PGA 411, the FPGA (1) 415 and the FPGA (2) 416 read circuit data from the ROM to constitute circuits having functions corresponding to the circuit data. As an alternative to this, the circuits may be constituted by reading the circuit data when a selector signal from outside is received.

As described above, all circuits, such as the logical circuits, that use the digital signals can be constituted by programmable integrated circuits. The programmable integrated circuits are able to change the contents of the ROM, which is a storage device for defining the function, to be adaptable to the unit to be combined at the time of use. Further, the programmable integrated circuit may have a function corresponding to the circuit data stored in the ROM. Therefore, a plurality of functions can be realized by the same hardware.

In the CPU technology, the region storing a program to be executed and the peripheral circuits are accessed by using a concept of the address. A circuit having a function of an address decoder may be constituted by using the programmable integrated circuit. The address space required for the circuit to have varies considerably from several K-bytes to several G-bytes depending upon the operation required for the unit to be combined. By constituting the address decoder by the programmable integrated circuit, the address space can easily be changed in accordance with data in the storage device for defining the function. Furthermore, the capacity of each of the CPU cell 412 and the RAM cell 413 in the PGA 411 can be enlarged/reduced to satisfy the desire.

By constituting the digital circuits, such as the CPU portion, the peripheral circuits, the address controller portion and the like by the programmable integrated circuits as described above, the control circuit having a desired function can be constituted by the same hardware without a necessity of changing a board on which the programmable integrated circuit is mounted. Since the circuit function and the data storage region can easily be changed, the number of processes required to complete the design can significantly be decreased. Since each programmable integrated circuit can be defined to be operated similarly to the convention circuit using a CPU, the present software resource can be used effectively.

Figure 42:
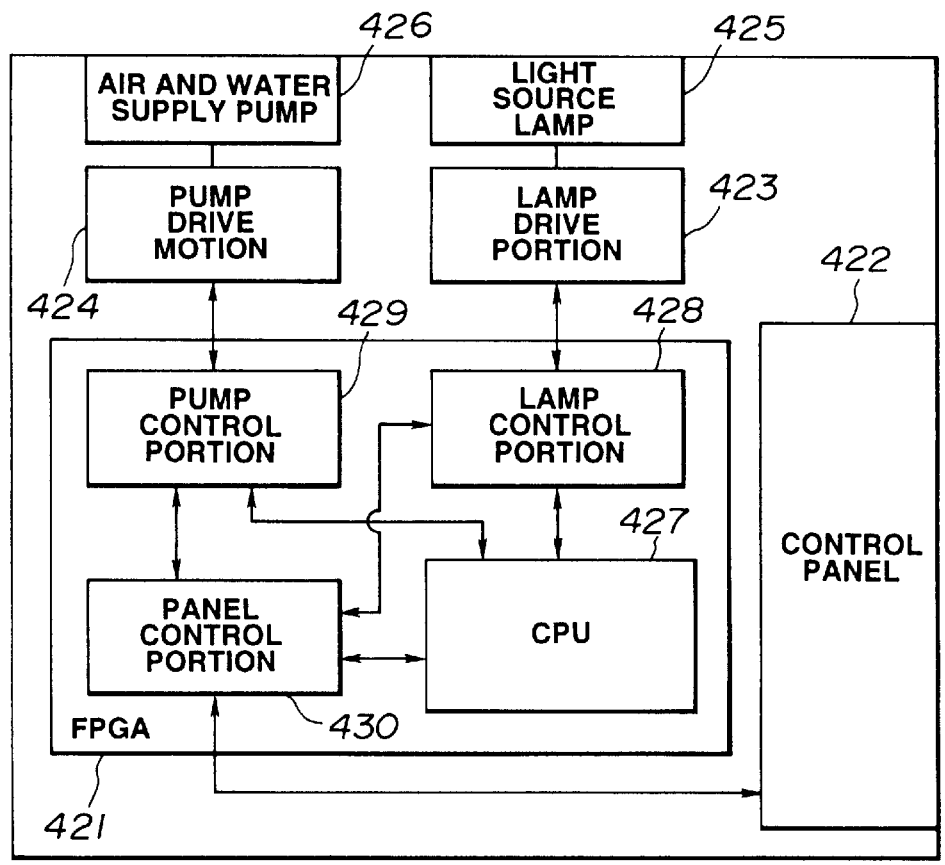
FIG. 42 is a block diagram which illustrates an example in which a light source unit of an endoscope apparatus is constituted by a programmable integrated circuit.

FIG. 42 illustrates an example in which a control circuit for a light source unit for an endoscope is constituted by a programmable integrated circuit.

A light source unit has a control portion 421 constituted by an FPGA. An operation panel 422, a lamp drive portion 423 and a pump drive portion 424 are connected to the control portion 421. A light source unit 425 for emitting irradiation light is connected to the lamp drive portion 423, while an air/water supply pump 426 for supplying air or water and performing a suction operation through a channel in the endoscope is connected to the pump drive portion 424. Respective function blocks in the control portion 421, such as the CPU 427, the lamp control portion 428, the pump control portion 429 and the panel control portion 430, are constituted by the FPGAs.

In the control portion 421, the CPU 427 controls the lamp control portion 428, the pump control portion 429 and the panel control portion 430. Furthermore, a control signal and the like are supplied/received to and from the operation panel 422, the lamp drive portion 423 and the pump drive portion 424. A signal representing the state of the operation of the apparatus and the state of setting in the same is supplied from the CPU 427, the lamp control portion 428 or the pump control portion 429 to the panel control portion 430. On the other hand, an operation instruction signal is supplied from the panel control portion 430 to the CPU 427.

By constituting the control circuit by the programmable integrated circuit as described above, change of the circuit and change of the function of the apparatus to be adaptable to the specifications can easily be realized by simply changing the ROM which stores the circuit data with the common hardware used. The circuit functions are, in the programmable integrated circuit, sequentially switched to be processed at each operation as shown in FIG. 39 so that the number of the programmable integrated circuits can be decreased and the size of the circuit can be reduced.

FIGS. 43 to 46 illustrate an example in which the structure of the electronic circuit using the programmable integrated circuit as shown in FIG. 39 is adapted to the light quantity adjustment means 171 shown in FIG. 12 of the endoscope apparatus according to the fifth embodiment.

Figure 43:
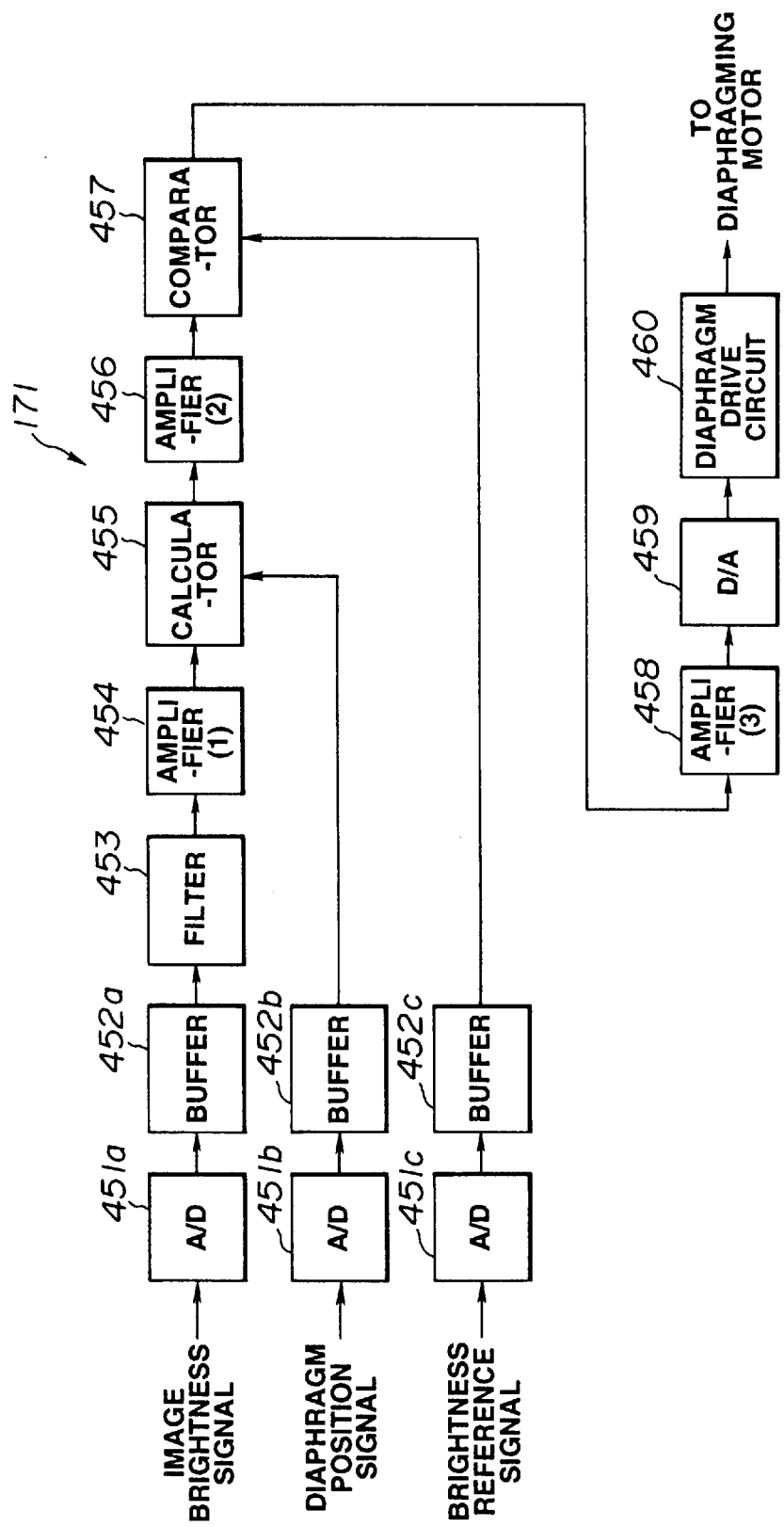
FIG. 43 is a block diagram which illustrates a specific structure of a light quantity adjustment means of a light source unit disposed in the endoscope apparatus according to the fifth embodiment shown in FIG. 12.

As shown in FIG. 43, the light quantity adjustment means 171 comprises A/D converters 451a, 451b and 451c for converting, into digital signals, an image brightness signal supplied from the CCU, a diaphragm position signal transmitted from a potentiometer or the like which detects the diaphragm position in synchronization with the rotation of the diaphragming blade, a brightness reference signal in proportion to the value of the light quantity adjustment set by the operation panel 177 or the like. The light quantity adjustment means 171 further comprises buffers 452a, 452b and 452c for latching digital signals respectively transmitted from the A/D converters 451a, 451b and 451c to arrange timing.

In a direction rearwards from the buffer 452a, the following units are disposed: a low pass filter 453 for permitting a low range to pass through, an amplifier (1) 454 for calculating the image brightness signal with a correction value corresponding to the diaphragm position signal to correct the same; an amplifier (2) 456 for amplifying at a predetermined degree of amplification to coincide the ratio of the output signal from the calculator 455 and the brightness reference signal; a comparator 457 for subjecting the output from the amplifier (2) 456 and the brightness reference signal to a comparison to transmit error data; an amplifier (3) 458 for amplifying the output from the comparator 457; a D/A converter 459 for converting the output from the amplifier (3) 458 into an analog signal; and a diaphragm drive circuit 460 for transmitting a drive signal in accordance with the output from the D/A converter 459 to rotate the diaphragming motor.

In the foregoing structure, the image brightness signal, the diaphragm position signal, and the brightness reference signal are respectively converted into digital signals by the A/D converters 451a, 451b and 451c and then latched by the buffers 452a, 452b and 452c to arrange the timing. Then, the digitized image brightness signal is subjected to a low pass process in the filter 453, amplified by the amplifier (1) 454 to coincide the ratio with respect to the diaphragm position signal, corrected by the calculator 455 with a correction value corresponding to the diaphragm position signal by calculations, amplified by the amplifier (2) 456 to coincide the ratio with respect to the brightness reference signal, and subjected to a comparison with the brightness reference signal in the comparator 457 so that error data is generated. Error data, which is the output from the comparator 457, is amplified by the amplifier (3) 458 and converted into an analog signal by the D/A converter 459. Then, it is supplied to the diaphragm drive circuit 460. The diaphragm drive circuit 460 transmits a drive signal corresponding to the error data to the diaphragming motor so that the diaphragming motor is rotated to displace the diaphragm. As a result, the light quantity is adjusted in accordance with the brightness of the image of a subject.

Figure 44:
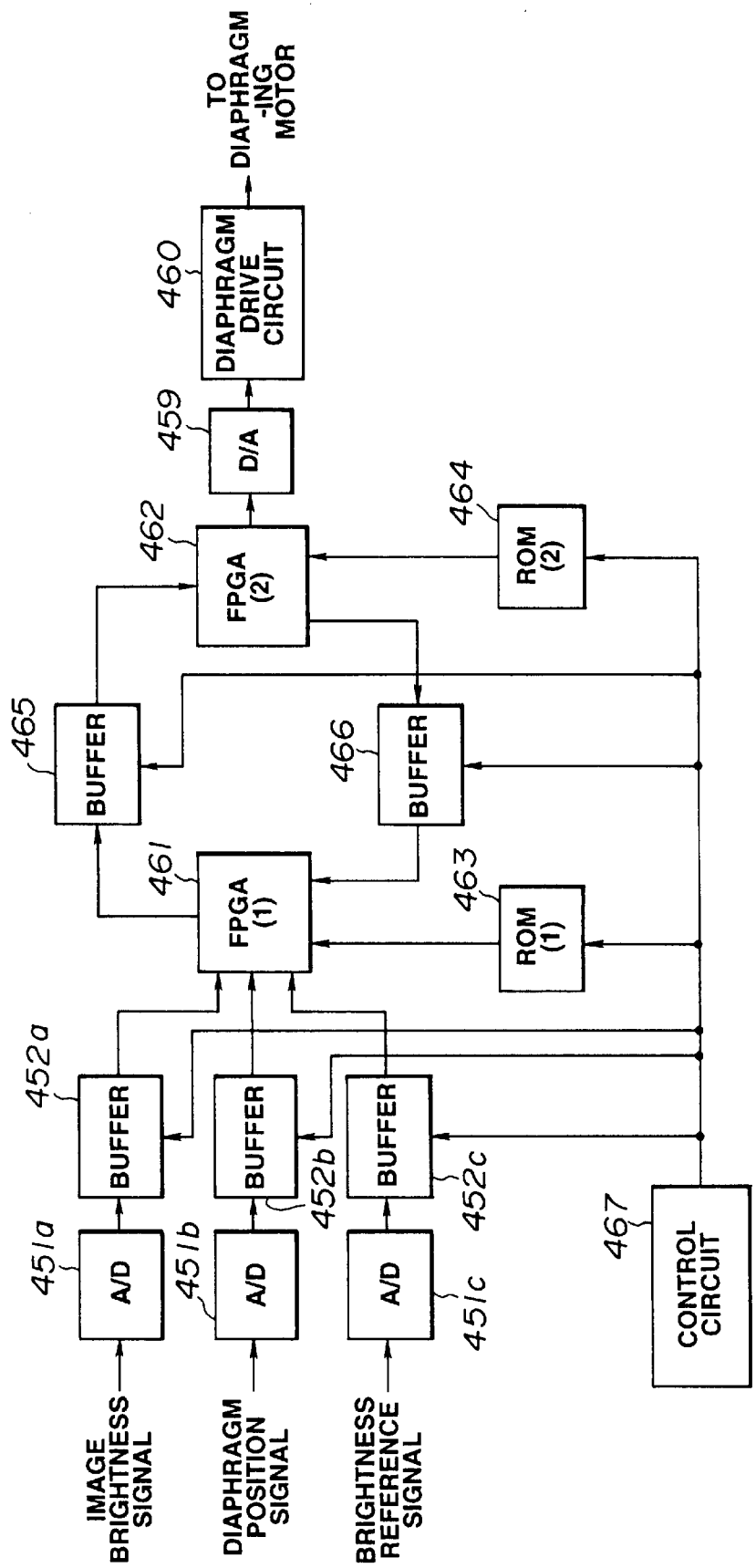
FIG. 44 is a block diagram which illustrates an example in which a structure having a function of a light quantity adjustment means is constituted by a programmable integrated circuit.

If the structure having the function of the light quantity adjustment means shown in FIG. 43 is constituted by a programmable integrated circuit, an arrangement as shown in FIG. 44 is exemplified.

That is, the portions between the buffers 452a, 452b and 452c and the D/A converter 459 are constituted by two FPGA (1) 461 and FPGA (2) 462.

A ROM (1) 463 and a ROM (2) 464, in each of which program data for constituting a circuit having a desired function is stored, are connected to the FPGA (1) 461 and the FPGA (2) 462. Buffers 465 and 466 for temporarily storing processed data or the like are disposed between the FPGA (1) 461 and the FPGA (2) 462 in such a manner that they are connected to the corresponding FPGAs. The outputs from the buffers 452a, 452b and 452c are connected to the FPGA (1) 461. The FPGA (1) 461 and the FPGA (2) 462 are connected to each other through buffers 465 and 466 The output from the FPGA (2) 462 is connected to the D/A converter 459 so that a light quantity adjustment means having a function similar to that of the light quantity adjustment shown in FIG. 43 is constituted.

Furthermore, a control circuit 467 for controlling each portion is provided. The control circuit 467 controls circuit data transmitted from the ROM (1) 463 and the ROM (2) 464 so that FPGA (1) 461 and the FPGA (2) 462 are rewritten. Furthermore, the output timing from each of the buffers 452*a*, 452*b* and 452*c* is controlled, and timing of input/output to and from each of the buffers 465 and 466 is controlled.

Figure 45:
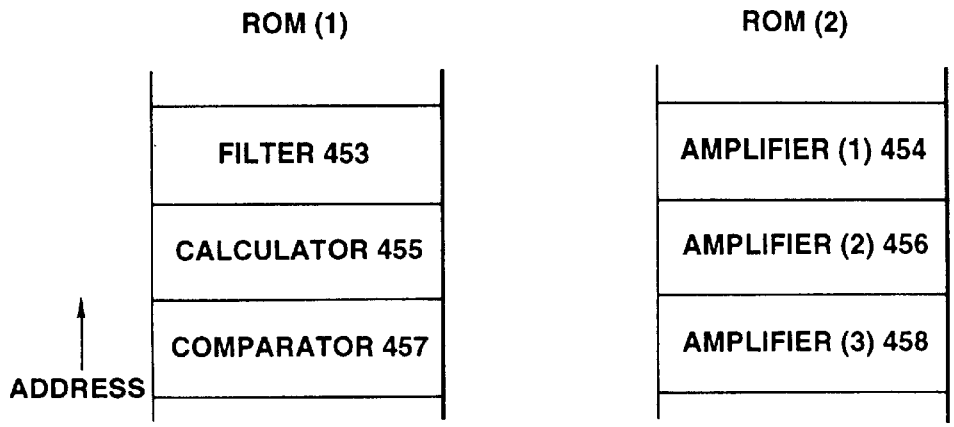
FIG. 45 is an explanatory view which illustrates circuit data stored in each ROM having the structure shown in FIG. 44.

The ROM (1) 463 and the ROM (2) 464 store program data for constituting circuits in the FPGA (1) 461 and the FPGA (2) 462. As shown in FIG. 45, the ROM (1) 463 sequentially stores, in predetermined addresses thereof, circuit data corresponding to the filter 453, the calculator 455 and the comparator 457 shown in FIG. 43. The ROM (2) 464 sequentially stores, in predetermined addresses, circuit data corresponding to the amplifier (1) 454, the amplifier (2) 456 and amplifier (3) 458 shown in FIG. 43.

Figure 46:
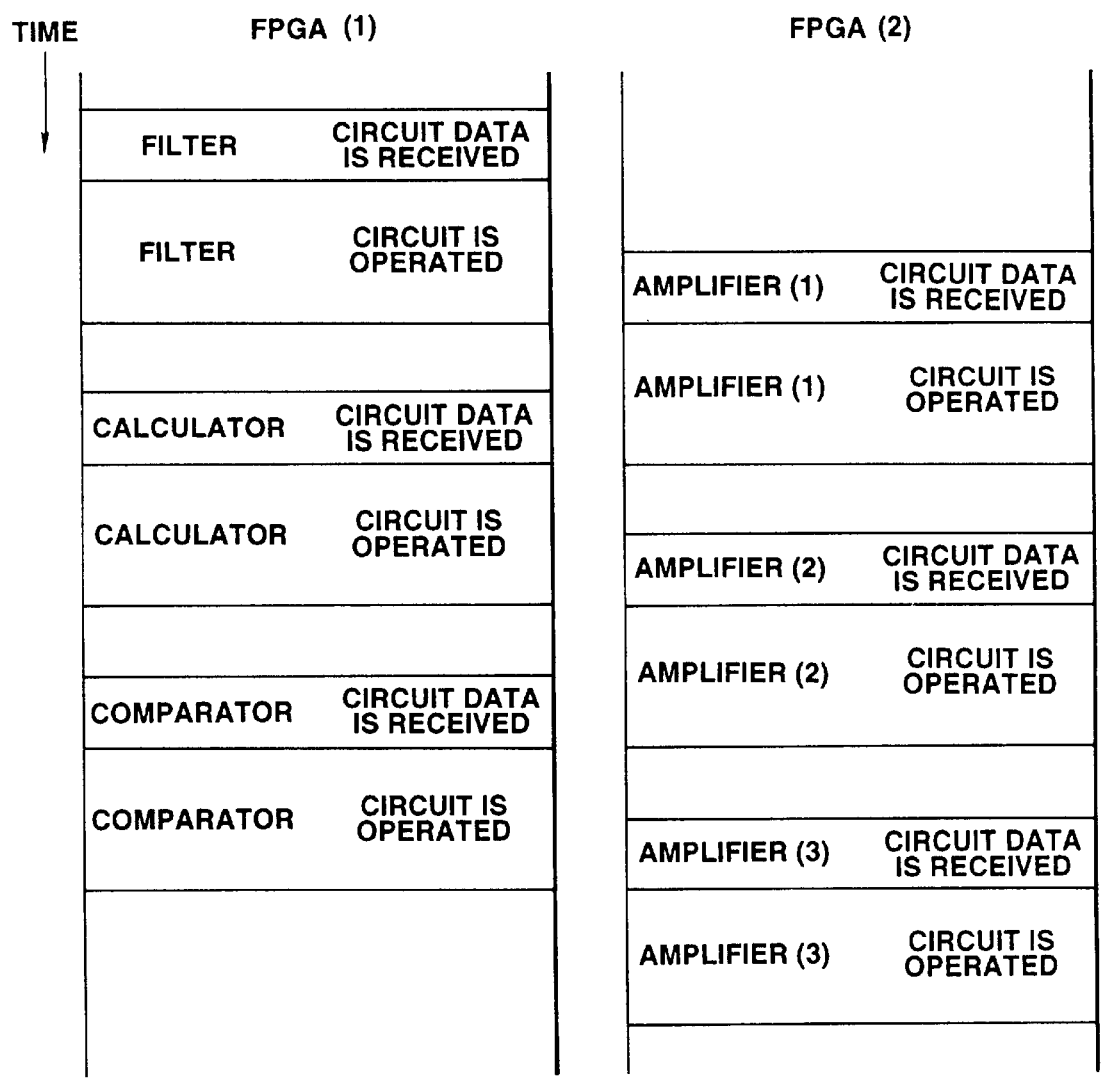
FIG. 46 is an operation explanatory view which illustrates the function structure and state of operation in each FPGA having the structure shown in FIG. 44.

The functional structure and the state of the operation of each of the FPGA (1) 461 and the FPGA (2) 462 will now be described with reference to FIG. 46. Referring to FIG. 46, time passes downwards and the states of the FPGA (1) 461 and the FPGA (2) 462 are expressed relatively.

The control to switch the states of the FPGA (1) 461 and the FPGA (2) 462 is performed by controlling circuit data transmitted from the ROM (1) 463 and the ROM (2) 464 by the control circuit 467.

Initially, circuit data of the filter 453 is transmitted from the ROM (1) 463 to the FPGA (1) 461. Then, the FPGA (1) 461 constitutes a circuit having the function of the filter 453.

The control circuit 467 latches the buffers 452*a*, 452*b* and 452*c*. The FPGA (1) 461 receives the latched image brightness signal as the filter 453 to subject it to a low-pass filter process. In this FPGA (1) 461, the circuit of the filter in the FPGA (1) 461 is connected to only an input terminal for receiving the image brightness signal connected to the buffer 452*a*. On the other hand, the circuit in the FPGA (1) 461 is not connected to the input terminals for the diaphragm position signal and the brightness reference signal to which the buffers 452*b* and 452*c* are respectively connected.

The image brightness signal subjected to the low pass process in the filter 453 is transmitted to the buffer 465. The buffer 465 latches the foregoing signal and stores the same temporarily.

On the other hand, circuit data of the amplifier (1) 454 is transmitted from the ROM (2) 464 to the FPGA (2) 462 until the FPGA (1) 461 completes the circuit operation of the filter 453. In synchronization with the completion of the circuit operation performed by the FPGA (1) 461, a circuit having the function of the amplifier (1) 454 is constituted in the FPGA (2) 462.

The FPGA (2) 462 receives the signal latched by the buffer 465 as the amplifier (1) 454 to amplify the same at a predetermined degree of amplification. The signal amplified by the amplifier (1) 454 is transmitted to the buffer 466. The buffer 466 latches the foregoing signal to temporarily store it. Latch timing signals for the buffers 465 and 466 are transmitted from the control circuit 467 so that the input/output timing to and from the buffers 465 and 466 is controlled.

Circuit data of the calculator 455 is transmitted from the ROM (1) 463 to the FPGA (1) 461 until the FPGA (1) 462 completes the circuit operation as the amplifier (1) 454. The FPGA (1) 461 receives the circuit data to constitute a circuit having the function of the calculator in synchronization with the completion of the circuit operation performed by the FPGA (2) 462. At this time, a circuit is constituted in the FPGA (1) 461 so that the input portion of the circuit serving as the calculator in the FPGA (1) 461 is connected to the input terminal for the diaphragm position signal to be connected to the buffer 452*b* and the input terminal to be connected to the buffer 466.

FPGA (1) 461, as the calculator 455, receives the signal latched by the buffer 466 and the diaphragm position signal latched by the buffer 452*b* to perform calculations to correct the image brightness signal with a correction value corresponding to the diaphragm position signal. The buffer 465 latches and temporarily stores the output from the FPGA (1) 461 as the signal calculated and processed in the calculator 455.

Circuit data of the amplifier (2) 456 is transmitted from the ROM (2) 464 to the FPGA (2) 462 until the FPGA (1) 461 completes the circuit operation as the calculator 455. The FPGA (2) 462 receives the foregoing circuit data to constitute a circuit having the function as the amplifier (2) 456 in synchronization with the completion of the circuit operation performed by the FPGA (1) 461.

The FPGA (2) 462, as the amplifier (2) 456, receives the signal latched by the buffer 465 to amplify the signal at a predetermined degree of amplification. The signal amplified by the amplifier (2) 456 is latched and temporarily stored in the buffer 466.

Circuit data of the comparator 457 is transmitted from the ROM (1) 463 to the FPGA (1) 461 until the FPGA (2) 462 completes the circuit operation as the amplifier (2) 456. The FPGA (1) 461 receives the foregoing circuit data to constitute a circuit having the function of the comparator 457 in synchronization with the completion of the circuit operation performed by the FPGA (2) 462. At this time, a circuit is constituted in the FPGA (1) 461 so that the input portion of the circuit serving as the comparator in the FPGA (1) 461 is connected to the input terminal for the brightness reference signal to be connected to the buffer 452*c* and the input terminal to be connected to the buffer 466.

The FPGA (1) 461, as the comparator 457, receives the signal latched by the buffer 466 and the brightness reference signal latched by the buffer 452*c* so as to perform a comparison process in which the corrected image brightness signal and the brightness reference signal are subjected to a comparison so as to generate error data. The buffer 465 latches the output from the FPGA (1) 461 which is error data, that is, the result of the comparison result from the comparator 457.

Circuit data of the amplifier (3) 458 is transmitted from the ROM (2) 464 to the FPGA (2) 462 until the FPGA (1) 461 completes the circuit operation as the comparator 457. The FPGA (2) 462 receives the foregoing circuit data to constitute a circuit having the function of the amplifier (3) 458 in synchronization with the circuit operation performed by the FPGA (1) 461. At this time, a circuit is constituted in the FPGA (2) 462 so that the output portion of the circuit serving as the amplifier (3) 458 is connected to the output terminal of the D/A converter 459.

The FPGA (2) 462, as the amplifier (3) 458, receives the signal latched by the buffer 465 to amplify the signal at a predetermined degree of amplification. An output signal transmitted as a signal amplified by the amplifier (3) 458 and after the circuit operation of the FPGA (2) 462 has been completed is supplied to the D/A converter 459. In the D/A converter 459, the signal is latched so as to be converted into an analog signal.

In a circuit portion that is constituted by using the programmable integrated circuit, the circuit functions among a plurality of circuit functions that are not operated simultaneously because they are operated time-sequentially and in series are realized by sequentially switching the circuits constituted in the FPGA (1) 461 and the FPGA (2) 462 and data to be processed is transmitted/received through the buffers 465 and 466 by arranging the timing. Thus, the circuits are commonly used with a small number of FPGAs so that a larger number of circuit functions are realized. As a result, the number and the size of the hardware, such as the gate array, can be reduced to constitute a circuit having the same performance. Consequently, circuits having a multiplicity of functions can be constituted by using a smaller number of FPGAs and therefore the size of the apparatus can be reduced.

Although the invention has been described in its preferred form with a certain degree of particularity, it is understood that the present disclosure of the preferred form can be changed in the details of construction and the combination and arrangement of parts may be resorted to without departing from the spirit and the scope of the invention as hereinafter claimed.

We claim:

1. An endoscope apparatus comprising:

an endoscope;

at least one peripheral unit connected to said endoscope having a function relating to an operation of said endoscope;

supply means for supplying a required signal or energy to said peripheral unit; and control means for controlling said supply means, wherein said control means includes at least one field programmable gate array, and a function required by said peripheral unit is realized by receiving circuit information from an external source, said circuit information being selectively written on said field programmable gate array to form said control circuit for controlling said supply means to supply said required signal or energy to said peripheral unit, wherein said peripheral unit includes a light guide cable of said endoscope, said supply means includes a light source portion for supplying irradiation light to said light guide cable, and said control means includes light quantity adjustment means that controls quantity of light emitted from said light source portion to adjust brightness of an image obtainable by said endoscope, wherein said light quantity adjustment means has image brightness detection means for detecting brightness of an image obtained by said endoscope, a diaphragm for adjusting quantity of light emitted from said light source, and diaphragm drive control means for controlling drive of said diaphragm in accordance with said brightness detected by said image brightness detection means, and said diaphragm drive control means includes said field programmable gate array to form an automatic light adjustment circuit by selectively setting loop gain characteristics to have response characteristics of an adequate light adjustment operation to be adaptable to a unit or an apparatus to be combined;

wherein said endoscope apparatus further comprises:

calculation circuit data storage means forming and storing a calculation circuit for calculating loop gain of an automatic light adjustment circuit corresponding to each diaphragm position of said diaphragm; and automatic light adjustment circuit data storage means forming and storing an automatic light adjustment circuit that drives said diaphragm to control a predetermined light quantity, wherein said diaphragm drive control means forms a calculating circuit and an automatic light adjustment circuit in accordance with said calculation circuit stored in said calculating circuit data storage means and said automatic light adjustment circuit stored in said automatic light adjustment circuit data storage means in said field programmable gate array, said diaphragm drive control means further including a correction value storage means for storing a correction value of a loop gain obtained by said calculating circuit when said calculating circuit is formed, and has correction means for correcting said loop gain at each diaphragm position in accordance with said correction value stored in said correction value storage means when said automatic light adjustment circuit is formed so that an automatic light adjustment circuit is formed.

2. An endoscope apparatus according to claim 1, wherein said diaphragm drive control means of said light quantity adjustment means constitutes said calculating circuit in accordance with said circuit information stored in said calculating circuit data storage means and then constitutes said automatic light adjustment circuit in accordance with said circuit information stored in said automatic light adjustment circuit data storage means in the same field programmable gate array.

3. An endoscope apparatus comprising:

an endoscope;

at least one peripheral unit connected to said endoscope having a function relating to an operation of said endoscope;

supply means for supplying a required signal or energy to said peripheral unit;

control means for controlling said supply means and including at least one field programmable gate array, and memory means for storing circuit information for constituting a control circuit for controlling said supply means, wherein said control means realizes a function required by said peripheral unit by receiving said circuit information from said memory means to selectively write said circuit information on said field programmable gate array so that said control circuit is constituted, wherein said memory means stores a plurality of circuit information items for constituting a digital circuit having a predetermined function.

wherein said control means has circuit information selection means for selecting data corresponding to setting a predetermined operation of said peripheral unit from said plurality of circuit information items in said memory means, and circuit constituting means that writes said selected data on said field programmable gate array to constitute said digital circuit, wherein said memory means stores said circuit information for a plurality of functions for constituting said digital circuit having said predetermined function, and wherein said control means further includes circuit information synthesizing means that synthesizes data selected by said circuit information selection means for each of said plurality of functions to supply said data to said circuit constituting means.

4. An endoscope apparatus comprising:

an endoscope;

at least one peripheral unit connected to said endoscope having a function relating to an operation of said endoscope;

supply means for supplying a required signal or energy to said peripheral unit; and control means for controlling said supply means, wherein said control means includes at least one field programmable gate array and a function required by said peripheral unit is realized by receiving circuit information from an external source, said circuit information being selectively written on said field programmable gate array to form said control circuit for controlling said supply means to supply said required signal or energy to said peripheral unit, wherein said control means comprises memory means for storing circuit information for defining a circuit function for determining each operation of a plurality of operations that are processed time-sequentially in a control circuit constituted by said field programmable gate array, buffer means for storing input/output data to be processed to and from said field programmable gate array for a predetermined time, and circuit constituting means for selecting circuit data for each said operation from circuit information for determining a plurality of operations stored in said memory means to sequentially supply said circuit data to said field programmable gate array to sequentially rewrite said circuit function in accordance with a time sequential process so as to constitute said control circuit.

5. An endoscope apparatus according to claim 4, wherein said control means includes a plurality of field programmable gate arrays, and wherein said control means rewrites a functional structure of said plurality of field programmable gate arrays sequentially and alternately by said circuit constituting means, thereby rewriting said circuit function of one of said plurality of field programmable gate arrays during operation of a circuit constituted by another one of said plurality of field programmable gate arrays.

6. An endoscope apparatus comprising:

an endoscope;

an electric knife connected to said endoscope for performing excision;

supply means for supplying a required signal or energy to said electric knife; and control means for controlling said supply means, wherein said control means includes at least one field programmable gate array and the function of excision provided by said electric knife is realized by receiving circuit information from an external source, said circuit information being selectively written on said field programmable gate array to form said control circuit for controlling said supply means to supply said required signal or energy to said electric knife.

\* \* \* \* \*